(12) United States Patent
Lee et al.

(10) Patent No.: US 9,328,362 B2
(45) Date of Patent: May 3, 2016

(54) RECOMBINANT ENZYME SYSTEMS FOR EFFICIENT PRODUCTION OF ITACONATE IN CELLS

(71) Applicant: Industrial Research Technology Institute, Hsinchu (TW)

(72) Inventors: Li-Feng Lee, Pingtung County (TW); Pei-Ching Chang, Hsinchu County (TW); Hsiang-Yuan Chu, New Taipei (TW)

(73) Assignee: Industrial Technology Research Institute, Hsinchu (TW)

(*) Notice: Subject to any disclaimer, the term of this patent is extended or adjusted under 35 U.S.C. 154(b) by 0 days.

(21) Appl. No.: 14/663,013

(22) Filed: Mar. 19, 2015

(65) Prior Publication Data

US 2015/0267230 A1    Sep. 24, 2015

Related U.S. Application Data

(60) Provisional application No. 61/955,468, filed on Mar. 19, 2014.

(51) Int. Cl.
*C12N 9/88* (2006.01)
*C12P 7/44* (2006.01)

(52) U.S. Cl.
CPC ...... *C12P 7/44* (2013.01); *C12N 9/88* (2013.01); *C12Y 401/01006* (2013.01); *C12Y 402/01003* (2013.01); *Y02P 20/52* (2015.11)

(58) Field of Classification Search
CPC .......................................................... C12N 9/88
USPC ....................................................... 530/350
See application file for complete search history.

(56) References Cited

U.S. PATENT DOCUMENTS

| 8,143,036 | B2 | 3/2012 | Liao et al. |
| 8,192,965 | B2 | 6/2012 | Wang et al. |
| 8,273,903 | B2 | 9/2012 | Hsu et al. |
| 8,338,158 | B2 | 12/2012 | Hsieh et al. |
| 8,440,436 | B2 | 5/2013 | Van Der Werf et al. |
| 2011/0070616 | A1 | 3/2011 | Van Der Werf et al. |
| 2011/0124066 | A1 | 5/2011 | Jore et al. |
| 2013/0171737 | A1 | 7/2013 | Way et al. |
| 2013/0172490 | A1 | 7/2013 | Way et al. |
| 2013/0274092 | A1 | 10/2013 | Lin et al. |

FOREIGN PATENT DOCUMENTS

| CN | 102464638 A | 5/2012 |
| CN | 103183764 A | 7/2013 |
| CN | 103183776 A | 7/2013 |
| JP | 2009027999 A | 2/2009 |
| JP | 2013051900 A | 3/2013 |
| TW | I374937 B | 10/2012 |
| TW | 201328735 A1 | 7/2013 |

OTHER PUBLICATIONS

Jensen et al. "Artificial Promoters for Metabolic Optimization" Biotechnology and Bioengineering vol. 58, pp. 191-195. 1997.
Jensen et al. "The Sequence of Spacers Between the Consensus Sequences Modulates the Strength of Prokaryotic Promoters" Applied and Environmental Microbiology vol. 64, pp. 82-87. 1998.
Jordan et al. "Biochemical and Spectroscopic Characterization of *Escherichia coli* Aconitases (AcnA and AcnB)" Biochemical Journal vol. 344, pp. 739-746. 1999.
Dwiarti et al. "Purification and Characterization of *cis*-Aconitic Acid Decarboxylase from *Aspergillus terreus* TN484-M1" Journal of Bioscience and Bioengineering vol. 94, pp. 29-33. 2002.
Williams et al. "*E. Coli* Aconitase B Structure Reveals a HEAT-Like Domain with Implications for Protein-Protein Recognition" Nature Structural Biology vol. 9, pp. 447-452. 2002.
Varghese et al. "Contrasting Sensitivities of *Escherichia coli* Aconitases A and B to Oxidation and Iron Depletion" Journal of Bacteriology vol. 185, pp. 221-230. 2003.
Tsuchiya et al. "Versatile Architecture of a Bacterial Aconitase B and its Catalytic Performance in the Sequential Reaction Coupled with Isocitrate Dehydrogenase" Biochimica et Biophysica Acta vol. 1784, pp. 1847-1856. 2008.
Steiger et al. "Biochemistry of Microbial Itaconic Acid Production" Frontiers in Microbiology vol. 4, pp. 1-5. 2013.
Blumhoff et al. "Targeting Enzymes to the Right Compartment: Metabolic Engineering for Itaconic Acid Production by *Aspergillus niger*" Metabolic Engineering vol. 19, pp. 26-32. 2013.

*Primary Examiner* — Maryam Monshipouri
(74) *Attorney, Agent, or Firm* — Cesari and McKenna LLP

(57) ABSTRACT

Described herein is a fusion polypeptide containing an aconitase and a cis-aconitate decarboxylase. Also described are a genetically modified cell expressing the fusion polypeptide and a method of using the cell to produce itaconate.

8 Claims, 8 Drawing Sheets

(A)

(B)

(A)

(B)

SEQUENCE LISTING

```
<160> NUMBER OF SEQ ID NOS: 43

<210> SEQ ID NO 1
<211> LENGTH: 1473
<212> TYPE: DNA
<213> ORGANISM: Aspergillus terreus
<220> FEATURE:
<221> NAME/KEY: CDS
<222> LOCATION: (1)..(1473)
<223> OTHER INFORMATION: cis-aconitateic acid decarboxylase

<400> SEQUENCE: 1 atg acc aag cag tct gct gat tcc aac gcg aag tct ggt gtg acc tct      48
Met Thr Lys Gln Ser Ala Asp Ser Asn Ala Lys Ser Gly Val Thr Ser
1               5                   10                  15 gag atc tgt cac tgg gcg tct aat ctc gcc act gat gat atc ccg agc      96
Glu Ile Cys His Trp Ala Ser Asn Leu Ala Thr Asp Asp Ile Pro Ser
            20                  25                  30
```

```
gac gtt ctg gag cgt gca aaa tac ctg atc ctg gat ggt atc gcg tgc      144
Asp Val Leu Glu Arg Ala Lys Tyr Leu Ile Leu Asp Gly Ile Ala Cys
        35                  40                  45 gcg tgg gta ggt gct cgt gtc cca tgg tct gaa aaa tac gtt caa gcg      192
Ala Trp Val Gly Ala Arg Val Pro Trp Ser Glu Lys Tyr Val Gln Ala
 50                  55                  60 acc atg tct ttc gaa cct ccg ggt gcg tgt cgt gtc atc ggt tac ggc      240
Thr Met Ser Phe Glu Pro Pro Gly Ala Cys Arg Val Ile Gly Tyr Gly
 65                  70                  75                  80 cag aaa ctg ggt ccg gta gcg gct gcc atg acg aac tct gca ttt att      288
Gln Lys Leu Gly Pro Val Ala Ala Ala Met Thr Asn Ser Ala Phe Ile
                 85                  90                  95 cag gcg acc gaa ctc gat gac tat cac tct gaa gcg ccg ctg cat tcc      336
Gln Ala Thr Glu Leu Asp Asp Tyr His Ser Glu Ala Pro Leu His Ser
            100                 105                 110 gcg tct atc gtt ctc ccg gca gtt ttc gcg gcg agc gaa gta ctg gcc      384
Ala Ser Ile Val Leu Pro Ala Val Phe Ala Ala Ser Glu Val Leu Ala
        115                 120                 125 gaa cag ggt aaa acc atc tct ggt att gac gtg att ctg gct gcg atc      432
Glu Gln Gly Lys Thr Ile Ser Gly Ile Asp Val Ile Leu Ala Ala Ile
130                 135                 140 gtt ggt ttc gag agc ggt cct cgc atc ggc aaa gcg atc tac ggt tct      480
Val Gly Phe Glu Ser Gly Pro Arg Ile Gly Lys Ala Ile Tyr Gly Ser
145                 150                 155                 160 gac ctc ctg aac aac ggc tgg cac tgc ggt gcg gta tat ggc gca ccg      528
Asp Leu Leu Asn Asn Gly Trp His Cys Gly Ala Val Tyr Gly Ala Pro
                165                 170                 175 gct ggt gcg ctc gca act ggt aag ctg ctg ggc ctc acg ccg gac agc      576
Ala Gly Ala Leu Ala Thr Gly Lys Leu Leu Gly Leu Thr Pro Asp Ser
            180                 185                 190 atg gaa gat gca ctg ggt att gcc tgc acg caa gca tgc ggc ctc atg      624
Met Glu Asp Ala Leu Gly Ile Ala Cys Thr Gln Ala Cys Gly Leu Met
        195                 200                 205 tcc gcg cag tat ggt ggc atg gtt aaa cgt gtt cag cac ggt ttc gca      672
Ser Ala Gln Tyr Gly Gly Met Val Lys Arg Val Gln His Gly Phe Ala
    210                 215                 220 gcg cgt aat ggt ctc ctc ggt ggc ctg ctg gct cac ggc ggc tac gag      720
Ala Arg Asn Gly Leu Leu Gly Gly Leu Leu Ala His Gly Gly Tyr Glu
225                 230                 235                 240 gcg atg aaa ggt gtt ctc gag cgt tct tac ggt ggc ttc ctg aag atg      768
Ala Met Lys Gly Val Leu Glu Arg Ser Tyr Gly Gly Phe Leu Lys Met
                245                 250                 255 ttc acc aag ggc aac ggt cgt gaa ccg ccg tac aaa gaa gag gtt      816
Phe Thr Lys Gly Asn Gly Arg Glu Pro Pro Tyr Lys Glu Glu Glu Val
            260                 265                 270 gtg gct ggt ctg ggt agc ttc tgg cac acc ttc acc att cgt atc aaa      864
Val Ala Gly Leu Gly Ser Phe Trp His Thr Phe Thr Ile Arg Ile Lys
        275                 280                 285 ctg tac gcg tgc tgc ggt ctc gta cac ggt cct gtt gaa gcc att gaa      912
Leu Tyr Ala Cys Cys Gly Leu Val His Gly Pro Val Glu Ala Ile Glu
    290                 295                 300 aac ctc cag ggt cgt tac ccg gaa ctg ctc aat cgt gct aac ctg tct      960
Asn Leu Gln Gly Arg Tyr Pro Glu Leu Leu Asn Arg Ala Asn Leu Ser
305                 310                 315                 320 aac atc cgc cac gtt cac gta caa ctc tct acc gcg agc aac tcc cac     1008
Asn Ile Arg His Val His Val Gln Leu Ser Thr Ala Ser Asn Ser His
                325                 330                 335 tgt ggt tgg atc cca gaa gag cgc cca atc tct tct atc gcg ggt caa     1056
Cys Gly Trp Ile Pro Glu Glu Arg Pro Ile Ser Ser Ile Ala Gly Gln
            340                 345                 350
```

```
atg tct gtc gca tat atc ctc gcc gtt cag ctc gtt gac caa cag tgt    1104
Met Ser Val Ala Tyr Ile Leu Ala Val Gln Leu Val Asp Gln Gln Cys
        355                 360                 365 ctg ctc agc cag ttc tcc gag ttt gac gat aat ctg gaa cgc ccg gaa    1152
Leu Leu Ser Gln Phe Ser Glu Phe Asp Asp Asn Leu Glu Arg Pro Glu
370                 375                 380 gtg tgg gac ctg gca cgt aag gtt acc agc tct caa tct gag gag ttc    1200
Val Trp Asp Leu Ala Arg Lys Val Thr Ser Ser Gln Ser Glu Glu Phe
385                 390                 395                 400 gac cag gac ggt aac tgt ctc tct gcc ggt cgc gtc cgt att gag ttc    1248
Asp Gln Asp Gly Asn Cys Leu Ser Ala Gly Arg Val Arg Ile Glu Phe
            405                 410                 415 aac gac ggc tcc tcc atc acc gaa tcc gtt gag aag ccg ctc ggt gta    1296
Asn Asp Gly Ser Ser Ile Thr Glu Ser Val Glu Lys Pro Leu Gly Val
        420                 425                 430 aag gaa cca atg cca aat gaa cgc atc ctg cac aaa tac cgt acc ctg    1344
Lys Glu Pro Met Pro Asn Glu Arg Ile Leu His Lys Tyr Arg Thr Leu
435                 440                 445 gcg ggt tct gta acg gac gaa agc cgt gtt aag gag atc gag gat ctc    1392
Ala Gly Ser Val Thr Asp Glu Ser Arg Val Lys Glu Ile Glu Asp Leu
    450                 455                 460 gtg ctc ggc ctg gac cgt ctg acc gat att agc ccg ctc ctc gag ctg    1440
Val Leu Gly Leu Asp Arg Leu Thr Asp Ile Ser Pro Leu Leu Glu Leu
465                 470                 475                 480 ctg aat tgt ccg gtt aaa tcc cca ctg gtt taa                        1473
Leu Asn Cys Pro Val Lys Ser Pro Leu Val
            485                 490

<210> SEQ ID NO 2
<211> LENGTH: 490
<212> TYPE: PRT
<213> ORGANISM: Aspergillus terreus

<400> SEQUENCE: 2

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
```

```
                180             185             190
Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
        290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ile Ala Gly Gln
                340                 345                 350

Met Ser Val Ala Tyr Ile Leu Ala Val Gln Leu Val Asp Gln Gln Cys
                355                 360                 365

Leu Leu Ser Gln Phe Ser Glu Phe Asp Asp Asn Leu Glu Arg Pro Glu
        370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Ile Thr Glu Ser Val Glu Lys Pro Leu Gly Val
            420                 425                 430

Lys Glu Pro Met Pro Asn Glu Arg Ile Leu His Lys Tyr Arg Thr Leu
        435                 440                 445

Ala Gly Ser Val Thr Asp Glu Ser Arg Val Lys Glu Ile Glu Asp Leu
    450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Val
                485                 490
```

<210> SEQ ID NO 3
<211> LENGTH: 2676
<212> TYPE: DNA
<213> ORGANISM: Escherichia coli
<220> FEATURE:
<221> NAME/KEY: CDS
<222> LOCATION: (1)..(2676)
<223> OTHER INFORMATION: aconitase A

<400> SEQUENCE: 3

```
atg tcg tca acc cta cga gaa gcc agt aag gac acg ttg cag gcc aaa    48
Met Ser Ser Thr Leu Arg Glu Ala Ser Lys Asp Thr Leu Gln Ala Lys
1               5                   10                  15 gat aaa act tac cac tac tac agc ctg ccg ctt gct gct aaa tca ctg    96
Asp Lys Thr Tyr His Tyr Tyr Ser Leu Pro Leu Ala Ala Lys Ser Leu
                20                  25                  30
```

-continued

| | | |
|---|---|---|
| ggc gat atc acc cgt cta ccc aag tca ctc aaa gtt ttg ctc gaa aac<br>Gly Asp Ile Thr Arg Leu Pro Lys Ser Leu Lys Val Leu Leu Glu Asn<br>35 40 45 | | 144 |
| ctg ctg cgc tgg cag gat ggt aac tcg gtt acc gaa gag gat atc cac<br>Leu Leu Arg Trp Gln Asp Gly Asn Ser Val Thr Glu Glu Asp Ile His<br>50 55 60 | | 192 |
| gcg ctg gca gga tgg ctg aaa aat gcc cat gct gac cgt gaa att gcc<br>Ala Leu Ala Gly Trp Leu Lys Asn Ala His Ala Asp Arg Glu Ile Ala<br>65 70 75 80 | | 240 |
| tac cgc ccg gca agg gtg ctg atg cag gac ttt acc ggc gta cct gcc<br>Tyr Arg Pro Ala Arg Val Leu Met Gln Asp Phe Thr Gly Val Pro Ala<br>85 90 95 | | 288 |
| gtt gtt gat ctg gcg gca atg cgc gaa gcg gtt aaa cgc ctc ggc ggc<br>Val Val Asp Leu Ala Ala Met Arg Glu Ala Val Lys Arg Leu Gly Gly<br>100 105 110 | | 336 |
| gat act gca aag gtt aac ccg ctc tca ccg gtc gac ctg gtc att gac<br>Asp Thr Ala Lys Val Asn Pro Leu Ser Pro Val Asp Leu Val Ile Asp<br>115 120 125 | | 384 |
| cac tcg gtg acc gtc gat cgt ttt ggt gat gat gag gca ttt gaa gaa<br>His Ser Val Thr Val Asp Arg Phe Gly Asp Asp Glu Ala Phe Glu Glu<br>130 135 140 | | 432 |
| aac gta cgc ctg gaa atg gag cgc aac cac gaa cgt tat gtg ttc ctg<br>Asn Val Arg Leu Glu Met Glu Arg Asn His Glu Arg Tyr Val Phe Leu<br>145 150 155 160 | | 480 |
| aaa tgg gga aag caa gcg ttc agt cgg ttt agc gtc gtg cca cca ggc<br>Lys Trp Gly Lys Gln Ala Phe Ser Arg Phe Ser Val Val Pro Pro Gly<br>165 170 175 | | 528 |
| aca ggc att tgc cat cag gtt aac ctc gaa tat ctc ggc aaa gca gtg<br>Thr Gly Ile Cys His Gln Val Asn Leu Glu Tyr Leu Gly Lys Ala Val<br>180 185 190 | | 576 |
| tgg agt gaa ttg cag gac ggt gaa tgg att gct tat ccg gat aca ctc<br>Trp Ser Glu Leu Gln Asp Gly Glu Trp Ile Ala Tyr Pro Asp Thr Leu<br>195 200 205 | | 624 |
| gtt ggt act gac tcg cac acc acc atg atc aac ggc ctt ggc gtg ctg<br>Val Gly Thr Asp Ser His Thr Thr Met Ile Asn Gly Leu Gly Val Leu<br>210 215 220 | | 672 |
| ggg tgg ggc gtt ggt ggg atc gaa gca gaa gcc gca atg tta ggc cag<br>Gly Trp Gly Val Gly Gly Ile Glu Ala Glu Ala Ala Met Leu Gly Gln<br>225 230 235 240 | | 720 |
| ccg gtt tcc atg ctt atc ccg gat gta gtg ggc ttc aaa ctt acc gga<br>Pro Val Ser Met Leu Ile Pro Asp Val Val Gly Phe Lys Leu Thr Gly<br>245 250 255 | | 768 |
| aaa tta cgt gaa ggt att acc gcc aca gac ctg gtt ctc act gtt acc<br>Lys Leu Arg Glu Gly Ile Thr Ala Thr Asp Leu Val Leu Thr Val Thr<br>260 265 270 | | 816 |
| caa atg ctg cgc aaa cat ggc gtg gtg ggg aaa ttc gtc gaa ttt tat<br>Gln Met Leu Arg Lys His Gly Val Val Gly Lys Phe Val Glu Phe Tyr<br>275 280 285 | | 864 |
| ggt gat ggt ctg gat tca cta ccg ttg gcg gat cgc gcc acc att gcc<br>Gly Asp Gly Leu Asp Ser Leu Pro Leu Ala Asp Arg Ala Thr Ile Ala<br>290 295 300 | | 912 |
| aat atg tcg cca gaa tat ggt gcc acc tgt ggc ttc ttc cca atc gat<br>Asn Met Ser Pro Glu Tyr Gly Ala Thr Cys Gly Phe Phe Pro Ile Asp<br>305 310 315 320 | | 960 |
| gct gta acc ctc gat tac atg cgt tta agc ggg cgc agc gaa gat cag<br>Ala Val Thr Leu Asp Tyr Met Arg Leu Ser Gly Arg Ser Glu Asp Gln<br>325 330 335 | | 1008 |
| gtc gag ttg gtc gaa aaa tat gcc aaa gcg cag ggc atg tgg cgt aac<br>Val Glu Leu Val Glu Lys Tyr Ala Lys Ala Gln Gly Met Trp Arg Asn<br>340 345 350 | | 1056 |

```
                                                           -continued ccg ggc gat gaa cca att ttt acc agt acg tta gaa ctg gat atg aat      1104
Pro Gly Asp Glu Pro Ile Phe Thr Ser Thr Leu Glu Leu Asp Met Asn
        355                 360                 365 gac gtt gaa gcg agc ctg gca ggg cct aaa cgc cca cag gat cgc gtt      1152
Asp Val Glu Ala Ser Leu Ala Gly Pro Lys Arg Pro Gln Asp Arg Val
370                 375                 380 gca ctg ccc gat gta cca aaa gca ttt gcc gcc agt aac gaa ctg gaa      1200
Ala Leu Pro Asp Val Pro Lys Ala Phe Ala Ala Ser Asn Glu Leu Glu
385                 390                 395                 400 gtg aat gcc acg cat aaa gat cgc cag ccg gtc gat tat gtt atg aac      1248
Val Asn Ala Thr His Lys Asp Arg Gln Pro Val Asp Tyr Val Met Asn
                405                 410                 415 gga cat cag tat cag tta cct gat ggc gct gtg gtc att gct gcg ata      1296
Gly His Gln Tyr Gln Leu Pro Asp Gly Ala Val Val Ile Ala Ala Ile
            420                 425                 430 acc tcg tgc acc aac acc tct aac cca agt gtg ctg atg gcc gca ggc      1344
Thr Ser Cys Thr Asn Thr Ser Asn Pro Ser Val Leu Met Ala Ala Gly
                435                 440                 445 ttg ctg gcg aaa aaa gcc gta act ctg ggc ctc aag cgg caa cca tgg      1392
Leu Leu Ala Lys Lys Ala Val Thr Leu Gly Leu Lys Arg Gln Pro Trp
        450                 455                 460 gtc aaa gcg tcg ctg gca ccg ggt tcg aaa gtc gtt tct gat tat ctg      1440
Val Lys Ala Ser Leu Ala Pro Gly Ser Lys Val Val Ser Asp Tyr Leu
465                 470                 475                 480 gca aaa gcg aaa ctg aca ccg tat ctc gac gaa ctg ggt ttt aac ctt      1488
Ala Lys Ala Lys Leu Thr Pro Tyr Leu Asp Glu Leu Gly Phe Asn Leu
                485                 490                 495 gtg gga tac ggt tgt acc acc tgt att ggt aac tct ggg ccg ctg ccc      1536
Val Gly Tyr Gly Cys Thr Thr Cys Ile Gly Asn Ser Gly Pro Leu Pro
            500                 505                 510 gat cct atc gaa acg gca atc aaa aaa agc gat tta acc gtc ggt gcg      1584
Asp Pro Ile Glu Thr Ala Ile Lys Lys Ser Asp Leu Thr Val Gly Ala
                515                 520                 525 gtg ctg tcc ggc aac cgt aac ttt gaa ggc cgt atc cat ccg ctg gtt      1632
Val Leu Ser Gly Asn Arg Asn Phe Glu Gly Arg Ile His Pro Leu Val
        530                 535                 540 aaa act aac tgg ctg gcc tcg ccg ccg ctg gtg gtt gcc tat gcg ctg      1680
Lys Thr Asn Trp Leu Ala Ser Pro Pro Leu Val Val Ala Tyr Ala Leu
545                 550                 555                 560 gcg gga aat atg aat atc aac ctg gct tct gag cct atc ggc cat gat      1728
Ala Gly Asn Met Asn Ile Asn Leu Ala Ser Glu Pro Ile Gly His Asp
                565                 570                 575 cgc aaa ggc gat ccg gtt tat ctg aaa gat atc tgg cca tcg gca caa      1776
Arg Lys Gly Asp Pro Val Tyr Leu Lys Asp Ile Trp Pro Ser Ala Gln
            580                 585                 590 gaa att gcc cgt gcg gta gaa caa gtc tcc aca gaa atg ttc cgc aaa      1824
Glu Ile Ala Arg Ala Val Glu Gln Val Ser Thr Glu Met Phe Arg Lys
                595                 600                 605 gag tac gca gaa gtt ttt gaa ggc aca gca gag tgg aag gga att aac      1872
Glu Tyr Ala Glu Val Phe Glu Gly Thr Ala Glu Trp Lys Gly Ile Asn
        610                 615                 620 gtc aca cga tcc gat acc tac ggt tgg cag gag gac tca acc tat att      1920
Val Thr Arg Ser Asp Thr Tyr Gly Trp Gln Glu Asp Ser Thr Tyr Ile
625                 630                 635                 640 cgc tta tcg cct ttc ttt gat gaa atg cag gca aca cca gca cca gtg      1968
Arg Leu Ser Pro Phe Phe Asp Glu Met Gln Ala Thr Pro Ala Pro Val
                645                 650                 655 gaa gat att cac ggt gcg cgg atc ctc gca atg ctg ggg gat tca gtc      2016
Glu Asp Ile His Gly Ala Arg Ile Leu Ala Met Leu Gly Asp Ser Val
```

```
                    660                 665                 670
acc act gac cat atc tct ccg gcg ggc agt att aag ccc gac agc cca       2064
Thr Thr Asp His Ile Ser Pro Ala Gly Ser Ile Lys Pro Asp Ser Pro
            675                 680                 685 gcg ggt cga tat cta caa ggt cgg ggt gtt gag cga aaa gac ttt aac       2112
Ala Gly Arg Tyr Leu Gln Gly Arg Gly Val Glu Arg Lys Asp Phe Asn
        690                 695                 700 tcc tac ggt tcg cgg cgt ggt aac cat gaa gtg atg atg cgc ggc acc       2160
Ser Tyr Gly Ser Arg Arg Gly Asn His Glu Val Met Met Arg Gly Thr
705                 710                 715                 720 ttc gcc aat att cgc atc cgt aat gaa atg gtg cct ggc gtt gaa ggg       2208
Phe Ala Asn Ile Arg Ile Arg Asn Glu Met Val Pro Gly Val Glu Gly
                725                 730                 735 ggg atg acg cgg cat tta cct gac agc gac gta gtc tct att tat gat       2256
Gly Met Thr Arg His Leu Pro Asp Ser Asp Val Val Ser Ile Tyr Asp
            740                 745                 750 gct gcg atg cgc tat aag cag gag caa acg ccg ctg gcg gtg att gcc       2304
Ala Ala Met Arg Tyr Lys Gln Glu Gln Thr Pro Leu Ala Val Ile Ala
        755                 760                 765 ggg aaa gag tat gga tca ggc tcc agt cgt gac tgg gcg gca aaa ggt       2352
Gly Lys Glu Tyr Gly Ser Gly Ser Ser Arg Asp Trp Ala Ala Lys Gly
770                 775                 780 ccg cgt ctg ctt ggt att cgt gtg gtg att gcc gaa tcg ttt gaa cga       2400
Pro Arg Leu Leu Gly Ile Arg Val Val Ile Ala Glu Ser Phe Glu Arg
785                 790                 795                 800 att cac cgt tcg aat tta att ggc atg ggc atc ctg ccg ctg gaa ttt       2448
Ile His Arg Ser Asn Leu Ile Gly Met Gly Ile Leu Pro Leu Glu Phe
                805                 810                 815 ccg caa ggc gta acg cgt aaa acg tta ggg cta acc ggg gaa gag aag       2496
Pro Gln Gly Val Thr Arg Lys Thr Leu Gly Leu Thr Gly Glu Glu Lys
            820                 825                 830 att gat att ggc gat ctg caa aac cta caa ccc ggc gcg acg gtt ccg       2544
Ile Asp Ile Gly Asp Leu Gln Asn Leu Gln Pro Gly Ala Thr Val Pro
        835                 840                 845 gtg acg ctt acg cgc gcg gat ggt agc cag gaa gtc gta ccc tgc cgt       2592
Val Thr Leu Thr Arg Ala Asp Gly Ser Gln Glu Val Val Pro Cys Arg
850                 855                 860 tgt cgt atc gac acc gcg acg gag ttg acc tac tac cag aac gac ggc       2640
Cys Arg Ile Asp Thr Ala Thr Glu Leu Thr Tyr Tyr Gln Asn Asp Gly
865                 870                 875                 880 att ttg cat tat gtc att cgt aat atg ttg aag taa                       2676
Ile Leu His Tyr Val Ile Arg Asn Met Leu Lys
                885                 890

<210> SEQ ID NO 4
<211> LENGTH: 891
<212> TYPE: PRT
<213> ORGANISM: Escherichia coli

<400> SEQUENCE: 4

Met Ser Ser Thr Leu Arg Glu Ala Ser Lys Asp Thr Leu Gln Ala Lys
1               5                   10                  15

Asp Lys Thr Tyr His Tyr Tyr Ser Leu Pro Leu Ala Ala Lys Ser Leu
            20                  25                  30

Gly Asp Ile Thr Arg Leu Pro Lys Ser Leu Lys Val Leu Leu Glu Asn
        35                  40                  45

Leu Leu Arg Trp Gln Asp Gly Asn Ser Val Thr Glu Glu Asp Ile His
    50                  55                  60

Ala Leu Ala Gly Trp Leu Lys Asn Ala His Ala Asp Arg Glu Ile Ala
```

```
                65                  70                  75                  80

Tyr Arg Pro Ala Arg Val Leu Met Gln Asp Phe Thr Gly Val Pro Ala
                85                  90                  95

Val Val Asp Leu Ala Ala Met Arg Glu Ala Val Lys Arg Leu Gly Gly
                100                 105                 110

Asp Thr Ala Lys Val Asn Pro Leu Ser Pro Val Asp Leu Val Ile Asp
                115                 120                 125

His Ser Val Thr Val Asp Arg Phe Gly Asp Asp Glu Ala Phe Glu Glu
                130                 135                 140

Asn Val Arg Leu Glu Met Glu Arg Asn His Glu Arg Tyr Val Phe Leu
145                 150                 155                 160

Lys Trp Gly Lys Gln Ala Phe Ser Arg Phe Ser Val Val Pro Pro Gly
                165                 170                 175

Thr Gly Ile Cys His Gln Val Asn Leu Glu Tyr Leu Gly Lys Ala Val
                180                 185                 190

Trp Ser Glu Leu Gln Asp Gly Glu Trp Ile Ala Tyr Pro Asp Thr Leu
                195                 200                 205

Val Gly Thr Asp Ser His Thr Thr Met Ile Asn Gly Leu Gly Val Leu
                210                 215                 220

Gly Trp Gly Val Gly Gly Ile Glu Ala Glu Ala Met Leu Gly Gln
225                 230                 235                 240

Pro Val Ser Met Leu Ile Pro Asp Val Val Gly Phe Lys Leu Thr Gly
                245                 250                 255

Lys Leu Arg Glu Gly Ile Thr Ala Thr Asp Leu Val Leu Thr Val Thr
                260                 265                 270

Gln Met Leu Arg Lys His Gly Val Val Gly Lys Phe Val Glu Phe Tyr
                275                 280                 285

Gly Asp Gly Leu Asp Ser Leu Pro Leu Ala Asp Arg Ala Thr Ile Ala
                290                 295                 300

Asn Met Ser Pro Glu Tyr Gly Ala Thr Cys Gly Phe Phe Pro Ile Asp
305                 310                 315                 320

Ala Val Thr Leu Asp Tyr Met Arg Leu Ser Gly Arg Ser Glu Asp Gln
                325                 330                 335

Val Glu Leu Val Glu Lys Tyr Ala Lys Ala Gln Gly Met Trp Arg Asn
                340                 345                 350

Pro Gly Asp Glu Pro Ile Phe Thr Ser Thr Leu Glu Leu Asp Met Asn
                355                 360                 365

Asp Val Glu Ala Ser Leu Ala Gly Pro Lys Arg Pro Gln Asp Arg Val
                370                 375                 380

Ala Leu Pro Asp Val Pro Lys Ala Phe Ala Ala Ser Asn Glu Leu Glu
385                 390                 395                 400

Val Asn Ala Thr His Lys Asp Arg Gln Pro Val Asp Tyr Val Met Asn
                405                 410                 415

Gly His Gln Tyr Gln Leu Pro Asp Gly Ala Val Ile Ala Ala Ile
                420                 425                 430

Thr Ser Cys Thr Asn Thr Ser Asn Pro Ser Val Leu Met Ala Ala Gly
                435                 440                 445

Leu Leu Ala Lys Lys Ala Val Thr Leu Gly Leu Lys Arg Gln Pro Trp
                450                 455                 460

Val Lys Ala Ser Leu Ala Pro Gly Ser Lys Val Val Ser Asp Tyr Leu
465                 470                 475                 480

Ala Lys Ala Lys Leu Thr Pro Tyr Leu Asp Glu Leu Gly Phe Asn Leu
                485                 490                 495
```

```
Val Gly Tyr Gly Cys Thr Thr Cys Ile Gly Asn Ser Gly Pro Leu Pro
            500                 505                 510

Asp Pro Ile Glu Thr Ala Ile Lys Lys Ser Asp Leu Thr Val Gly Ala
            515                 520                 525

Val Leu Ser Gly Asn Arg Asn Phe Glu Gly Arg Ile His Pro Leu Val
    530                 535                 540

Lys Thr Asn Trp Leu Ala Ser Pro Leu Val Val Ala Tyr Ala Leu
545                 550                 555                 560

Ala Gly Asn Met Asn Ile Asn Leu Ala Ser Glu Pro Ile Gly His Asp
                565                 570                 575

Arg Lys Gly Asp Pro Val Tyr Leu Lys Asp Ile Trp Pro Ser Ala Gln
            580                 585                 590

Glu Ile Ala Arg Ala Val Glu Gln Val Ser Thr Glu Met Phe Arg Lys
        595                 600                 605

Glu Tyr Ala Glu Val Phe Glu Gly Thr Ala Glu Trp Lys Gly Ile Asn
    610                 615                 620

Val Thr Arg Ser Asp Thr Tyr Gly Trp Gln Glu Asp Ser Thr Tyr Ile
625                 630                 635                 640

Arg Leu Ser Pro Phe Phe Asp Glu Met Gln Ala Thr Pro Ala Pro Val
                645                 650                 655

Glu Asp Ile His Gly Ala Arg Ile Leu Ala Met Leu Gly Asp Ser Val
            660                 665                 670

Thr Thr Asp His Ile Ser Pro Ala Gly Ser Ile Lys Pro Asp Ser Pro
        675                 680                 685

Ala Gly Arg Tyr Leu Gln Gly Arg Gly Val Glu Arg Lys Asp Phe Asn
    690                 695                 700

Ser Tyr Gly Ser Arg Arg Gly Asn His Glu Val Met Met Arg Gly Thr
705                 710                 715                 720

Phe Ala Asn Ile Arg Ile Arg Asn Glu Met Val Pro Gly Val Glu Gly
                725                 730                 735

Gly Met Thr Arg His Leu Pro Asp Ser Asp Val Val Ser Ile Tyr Asp
            740                 745                 750

Ala Ala Met Arg Tyr Lys Gln Glu Gln Thr Pro Leu Ala Val Ile Ala
        755                 760                 765

Gly Lys Glu Tyr Gly Ser Gly Ser Ser Arg Asp Trp Ala Ala Lys Gly
    770                 775                 780

Pro Arg Leu Leu Gly Ile Arg Val Val Ile Ala Glu Ser Phe Glu Arg
785                 790                 795                 800

Ile His Arg Ser Asn Leu Ile Gly Met Gly Ile Leu Pro Leu Glu Phe
                805                 810                 815

Pro Gln Gly Val Thr Arg Lys Thr Leu Gly Leu Thr Gly Glu Glu Lys
            820                 825                 830

Ile Asp Ile Gly Asp Leu Gln Asn Leu Gln Pro Gly Ala Thr Val Pro
        835                 840                 845

Val Thr Leu Thr Arg Ala Asp Gly Ser Gln Glu Val Val Pro Cys Arg
    850                 855                 860

Cys Arg Ile Asp Thr Ala Thr Glu Leu Thr Tyr Tyr Gln Asn Asp Gly
865                 870                 875                 880

Ile Leu His Tyr Val Ile Arg Asn Met Leu Lys
                885                 890

<210> SEQ ID NO 5
<211> LENGTH: 2598
```

```
<212> TYPE: DNA
<213> ORGANISM: Escherichia coli
<220> FEATURE:
<221> NAME/KEY: CDS
<222> LOCATION: (1)..(2598)
<223> OTHER INFORMATION: aconitase B

<400> SEQUENCE: 5 atg cta gaa gaa tac cgt aag cac gta gct gag cgt gcc gct gag ggg      48
Met Leu Glu Glu Tyr Arg Lys His Val Ala Glu Arg Ala Ala Glu Gly
1               5                   10                  15 att gcg ccc aaa ccc ctg gat gca aac caa atg gcc gca ctt gta gag      96
Ile Ala Pro Lys Pro Leu Asp Ala Asn Gln Met Ala Ala Leu Val Glu
                20                  25                  30 ctg ctg aaa aac ccg ccc gcg ggc gaa gaa gaa ttc ctg tta gat ctg     144
Leu Leu Lys Asn Pro Pro Ala Gly Glu Glu Glu Phe Leu Leu Asp Leu
            35                  40                  45 tta acc aac cgt gtt ccc cca ggc gtc gat gaa gcc gcc tat gtc aaa     192
Leu Thr Asn Arg Val Pro Pro Gly Val Asp Glu Ala Ala Tyr Val Lys
50                  55                  60 gca ggc ttc ctg gct gct atc gcg aaa ggc gaa gcc aaa tcc cct ctg     240
Ala Gly Phe Leu Ala Ala Ile Ala Lys Gly Glu Ala Lys Ser Pro Leu
65                  70                  75                  80 ctg act ccg gaa aaa gcc atc gaa ctg ctg ggc acc atg cag ggt ggt     288
Leu Thr Pro Glu Lys Ala Ile Glu Leu Leu Gly Thr Met Gln Gly Gly
                85                  90                  95 tac aac att cat ccg ctg atc gac gcg ctg gat gat gcc aaa ctg gca     336
Tyr Asn Ile His Pro Leu Ile Asp Ala Leu Asp Asp Ala Lys Leu Ala
                100                 105                 110 cct att gct gcc aaa gca ctt tct cac acg ctg ctg atg ttc gat aac     384
Pro Ile Ala Ala Lys Ala Leu Ser His Thr Leu Leu Met Phe Asp Asn
            115                 120                 125 ttc tat gac gta gaa gag aaa gcg aaa gca ggc aac gaa tat gcg aag     432
Phe Tyr Asp Val Glu Glu Lys Ala Lys Ala Gly Asn Glu Tyr Ala Lys
        130                 135                 140 cag gtt atg cag tcc tgg gcg gat gcc gaa tgg ttc ctg aat cgc ccg     480
Gln Val Met Gln Ser Trp Ala Asp Ala Glu Trp Phe Leu Asn Arg Pro
145                 150                 155                 160 gcg ctg gct gaa aaa ctg acc gtt act gtc ttc aaa gtc act ggc gaa     528
Ala Leu Ala Glu Lys Leu Thr Val Thr Val Phe Lys Val Thr Gly Glu
                165                 170                 175 act aac acc gat gac ctt tct ccg gca ccg gat gcg tgg tca cgc ccg     576
Thr Asn Thr Asp Asp Leu Ser Pro Ala Pro Asp Ala Trp Ser Arg Pro
                180                 185                 190 gat atc cca ctg cac gcg ctg gcg atg ctg aaa aac gcc cgt gaa ggt     624
Asp Ile Pro Leu His Ala Leu Ala Met Leu Lys Asn Ala Arg Glu Gly
            195                 200                 205 att gag cca gac cag cct ggt gtt gtt ggt ccg atc aag caa atc gaa     672
Ile Glu Pro Asp Gln Pro Gly Val Val Gly Pro Ile Lys Gln Ile Glu
        210                 215                 220 gct ctg caa cag aaa ggt ttc ccg ctg gcg tac gtc ggt gac gtt gtg     720
Ala Leu Gln Gln Lys Gly Phe Pro Leu Ala Tyr Val Gly Asp Val Val
225                 230                 235                 240 ggt acg ggt tct tcg cgt aaa tcc gcc act aac tcc gtt ctg tgg ttt     768
Gly Thr Gly Ser Ser Arg Lys Ser Ala Thr Asn Ser Val Leu Trp Phe
                245                 250                 255 atg ggc gat gat att cca cat gtg ccg aac aaa cgc ggc ggt ggt ttg     816
Met Gly Asp Asp Ile Pro His Val Pro Asn Lys Arg Gly Gly Gly Leu
                260                 265                 270 tgc ctc ggc ggt aaa att gca ccc atc ttc ttt aac acg atg gaa gac     864
Cys Leu Gly Gly Lys Ile Ala Pro Ile Phe Phe Asn Thr Met Glu Asp
```

```
                275                 280                 285
gcg ggt gca ctg cca atc gaa gtc gac gtc tct aac ctg aac atg ggc    912
Ala Gly Ala Leu Pro Ile Glu Val Asp Val Ser Asn Leu Asn Met Gly
290                 295                 300 gac gtg att gac gtt tac ccg tac aaa ggt gaa gtg cgt aac cac gaa    960
Asp Val Ile Asp Val Tyr Pro Tyr Lys Gly Glu Val Arg Asn His Glu
305                 310                 315                 320 acc ggc gaa ctg ctg gcg acc ttc gaa ctg aaa acc gac gtg ctg att   1008
Thr Gly Glu Leu Leu Ala Thr Phe Glu Leu Lys Thr Asp Val Leu Ile
                325                 330                 335 gat gaa gtg cgt gct ggt ggc cgt att ccg ctg att atc ggg cgt ggc   1056
Asp Glu Val Arg Ala Gly Gly Arg Ile Pro Leu Ile Ile Gly Arg Gly
340                 345                 350 ctg acc acc aaa gcg cgt gaa gca ctt ggt ctg ccg cac agt gat gtg   1104
Leu Thr Thr Lys Ala Arg Glu Ala Leu Gly Leu Pro His Ser Asp Val
        355                 360                 365 ttc cgt cag gcg aaa gat gtc gct gag agc gat cgc ggc ttc tcg ctg   1152
Phe Arg Gln Ala Lys Asp Val Ala Glu Ser Asp Arg Gly Phe Ser Leu
370                 375                 380 gcg caa aaa atg gta ggc cgt gcc tgt ggc gtg aaa ggc att cgt ccg   1200
Ala Gln Lys Met Val Gly Arg Ala Cys Gly Val Lys Gly Ile Arg Pro
385                 390                 395                 400 ggc gcg tac tgt gaa ccg aaa atg act tct gta ggt tcc cag gac acc   1248
Gly Ala Tyr Cys Glu Pro Lys Met Thr Ser Val Gly Ser Gln Asp Thr
                405                 410                 415 acc ggc ccg atg acc cgt gat gaa ctg aaa gac ctg gcg tgc ctg ggc   1296
Thr Gly Pro Met Thr Arg Asp Glu Leu Lys Asp Leu Ala Cys Leu Gly
            420                 425                 430 ttc tcg gct gac ctg gtg atg cag tct ttc tgc cac acc gcg gcg tat   1344
Phe Ser Ala Asp Leu Val Met Gln Ser Phe Cys His Thr Ala Ala Tyr
            435                 440                 445 ccg aag cca gtt gac gtg aac acg cac cac acg ctg ccg gac ttc att   1392
Pro Lys Pro Val Asp Val Asn Thr His His Thr Leu Pro Asp Phe Ile
450                 455                 460 atg aac cgt ggc ggt gtg tcg ctg cgt ccg ggt gac ggc gtc att cac   1440
Met Asn Arg Gly Gly Val Ser Leu Arg Pro Gly Asp Gly Val Ile His
465                 470                 475                 480 tcc tgg ctg aac cgt atg ctg ctg ccg gat acc gtc ggt acc ggt ggt   1488
Ser Trp Leu Asn Arg Met Leu Leu Pro Asp Thr Val Gly Thr Gly Gly
                485                 490                 495 gac tcc cat acc cgt ttc ccg atc ggt atc tct ttc ccg gcg ggt tct   1536
Asp Ser His Thr Arg Phe Pro Ile Gly Ile Ser Phe Pro Ala Gly Ser
            500                 505                 510 ggt ctg gtg gcg ttt gct gcc gca act ggc gta atg ccg ctt gat atg   1584
Gly Leu Val Ala Phe Ala Ala Ala Thr Gly Val Met Pro Leu Asp Met
        515                 520                 525 ccg gaa tcc gtt ctg gtg cgc ttc aaa ggc aaa atg cag ccg ggc atc   1632
Pro Glu Ser Val Leu Val Arg Phe Lys Gly Lys Met Gln Pro Gly Ile
530                 535                 540 acc ctg cgc gat ctg gta cac gct att ccg ctg tat gcg atc aaa caa   1680
Thr Leu Arg Asp Leu Val His Ala Ile Pro Leu Tyr Ala Ile Lys Gln
545                 550                 555                 560 ggt ctg ctg acc gtt gag aag aaa ggc aag aaa aac atc ttc tct ggc   1728
Gly Leu Leu Thr Val Glu Lys Lys Gly Lys Lys Asn Ile Phe Ser Gly
                565                 570                 575 cgc atc ctg gaa att gaa ggt ctg ccg gat ctg aaa gtt gag cag gcc   1776
Arg Ile Leu Glu Ile Glu Gly Leu Pro Asp Leu Lys Val Glu Gln Ala
            580                 585                 590 ttt gag cta acc gat gcg tcc gcc gag cgt tct gcc gct ggt tgt acc   1824
Phe Glu Leu Thr Asp Ala Ser Ala Glu Arg Ser Ala Ala Gly Cys Thr
```

```
                Phe Glu Leu Thr Asp Ala Ser Ala Glu Arg Ser Ala Ala Gly Cys Thr
                            595                 600                 605 atc aag ctg aac aaa gaa ccg atc atc gaa tac ctg aac tct aac atc       1872
Ile Lys Leu Asn Lys Glu Pro Ile Ile Glu Tyr Leu Asn Ser Asn Ile
610                 615                 620 gtc ctg ctg aag tgg atg atc gcg gaa ggt tac ggc gat cgt cgt acc       1920
Val Leu Leu Lys Trp Met Ile Ala Glu Gly Tyr Gly Asp Arg Arg Thr
625                 630                 635                 640 ctg gaa cgt cgt att cag ggc atg gaa aaa tgg ctg gcg aat cct gag       1968
Leu Glu Arg Arg Ile Gln Gly Met Glu Lys Trp Leu Ala Asn Pro Glu
                645                 650                 655 ctg ctg gaa gcc gat gca gat gcg gaa tac gcg gca gtg atc gac atc       2016
Leu Leu Glu Ala Asp Ala Asp Ala Glu Tyr Ala Ala Val Ile Asp Ile
                660                 665                 670 gat ctg gcg gat att aaa gag cca atc ctg tgt gct ccg aac gac ccg       2064
Asp Leu Ala Asp Ile Lys Glu Pro Ile Leu Cys Ala Pro Asn Asp Pro
            675                 680                 685 gat gac gcg cgt ccg ctg tct gcg gta cag ggt gag aag atc gac gaa       2112
Asp Asp Ala Arg Pro Leu Ser Ala Val Gln Gly Glu Lys Ile Asp Glu
690                 695                 700 gtg ttt atc ggt tcc tgc atg acc aac atc ggt cac ttc cgt gct gcg       2160
Val Phe Ile Gly Ser Cys Met Thr Asn Ile Gly His Phe Arg Ala Ala
705                 710                 715                 720 ggt aaa ctg ctg gat gcg cat aaa ggt cag ttg ccg acc cgc ctg tgg       2208
Gly Lys Leu Leu Asp Ala His Lys Gly Gln Leu Pro Thr Arg Leu Trp
                725                 730                 735 gtg gca ccg cca acc cgt atg gac gcc gca cag ttg acc gaa gaa ggc       2256
Val Ala Pro Pro Thr Arg Met Asp Ala Ala Gln Leu Thr Glu Glu Gly
                740                 745                 750 tac tac agc gtc ttc ggt aag agt ggt gcg cgt atc gag atc cct ggc       2304
Tyr Tyr Ser Val Phe Gly Lys Ser Gly Ala Arg Ile Glu Ile Pro Gly
            755                 760                 765 tgt tcc ctg tgt atg ggt aac cag gcg cgt gtg gcg gac ggt gca acg       2352
Cys Ser Leu Cys Met Gly Asn Gln Ala Arg Val Ala Asp Gly Ala Thr
770                 775                 780 gtg gtt tcc acc tct acc cgt aac ttc ccg aac cgt ctg ggt act ggc       2400
Val Val Ser Thr Ser Thr Arg Asn Phe Pro Asn Arg Leu Gly Thr Gly
785                 790                 795                 800 gcg aat gtc ttc ctg gct tct gcg gaa ctg gcg gct gtt gcg gcg ctg       2448
Ala Asn Val Phe Leu Ala Ser Ala Glu Leu Ala Ala Val Ala Ala Leu
                805                 810                 815 att ggc aaa ctg ccg acg ccg gaa gag tac cag acc tac gtg gcg cag       2496
Ile Gly Lys Leu Pro Thr Pro Glu Glu Tyr Gln Thr Tyr Val Ala Gln
                820                 825                 830 gta gat aaa aca gcc gtt gat act tac cgt tat ctg aac ttc aac cag       2544
Val Asp Lys Thr Ala Val Asp Thr Tyr Arg Tyr Leu Asn Phe Asn Gln
            835                 840                 845 ctt tct cag tac acc gag aaa gcc gat ggg gtg att ttc cag act gcg       2592
Leu Ser Gln Tyr Thr Glu Lys Ala Asp Gly Val Ile Phe Gln Thr Ala
850                 855                 860 gtt taa                                                               2598
Val
865

<210> SEQ ID NO 6
<211> LENGTH: 865
<212> TYPE: PRT
<213> ORGANISM: Escherichia coli

<400> SEQUENCE: 6
```

```
Met Leu Glu Glu Tyr Arg Lys His Val Ala Glu Arg Ala Ala Glu Gly
1               5                   10                  15
Ile Ala Pro Lys Pro Leu Asp Ala Asn Gln Met Ala Ala Leu Val Glu
            20                  25                  30
Leu Leu Lys Asn Pro Pro Ala Gly Glu Glu Phe Leu Leu Asp Leu
        35                  40                  45
Leu Thr Asn Arg Val Pro Pro Gly Val Asp Glu Ala Ala Tyr Val Lys
    50                  55                  60
Ala Gly Phe Leu Ala Ala Ile Ala Lys Gly Glu Ala Lys Ser Pro Leu
65                  70                  75                  80
Leu Thr Pro Glu Lys Ala Ile Glu Leu Leu Gly Thr Met Gln Gly Gly
                85                  90                  95
Tyr Asn Ile His Pro Leu Ile Asp Ala Leu Asp Asp Ala Lys Leu Ala
                100                 105                 110
Pro Ile Ala Ala Lys Ala Leu Ser His Thr Leu Leu Met Phe Asp Asn
            115                 120                 125
Phe Tyr Asp Val Glu Glu Lys Ala Lys Ala Gly Asn Glu Tyr Ala Lys
    130                 135                 140
Gln Val Met Gln Ser Trp Ala Asp Ala Glu Trp Phe Leu Asn Arg Pro
145                 150                 155                 160
Ala Leu Ala Glu Lys Leu Thr Val Thr Val Phe Lys Val Thr Gly Glu
                165                 170                 175
Thr Asn Thr Asp Asp Leu Ser Pro Ala Pro Asp Ala Trp Ser Arg Pro
            180                 185                 190
Asp Ile Pro Leu His Ala Leu Ala Met Leu Lys Asn Ala Arg Glu Gly
            195                 200                 205
Ile Glu Pro Asp Gln Pro Gly Val Val Gly Pro Ile Lys Gln Ile Glu
    210                 215                 220
Ala Leu Gln Gln Lys Gly Phe Pro Leu Ala Tyr Val Gly Asp Val Val
225                 230                 235                 240
Gly Thr Gly Ser Ser Arg Lys Ser Ala Thr Asn Ser Val Leu Trp Phe
                245                 250                 255
Met Gly Asp Asp Ile Pro His Val Pro Asn Lys Arg Gly Gly Gly Leu
            260                 265                 270
Cys Leu Gly Gly Lys Ile Ala Pro Ile Phe Phe Asn Thr Met Glu Asp
        275                 280                 285
Ala Gly Ala Leu Pro Ile Glu Val Asp Val Ser Asn Leu Asn Met Gly
        290                 295                 300
Asp Val Ile Asp Val Tyr Pro Tyr Lys Gly Glu Val Arg Asn His Glu
305                 310                 315                 320
Thr Gly Glu Leu Leu Ala Thr Phe Glu Leu Lys Thr Asp Val Leu Ile
                325                 330                 335
Asp Glu Val Arg Ala Gly Gly Arg Ile Pro Leu Ile Ile Gly Arg Gly
            340                 345                 350
Leu Thr Thr Lys Ala Arg Glu Ala Leu Gly Leu Pro His Ser Asp Val
        355                 360                 365
Phe Arg Gln Ala Lys Asp Val Ala Glu Ser Arg Gly Phe Ser Leu
    370                 375                 380
Ala Gln Lys Met Val Gly Arg Ala Cys Gly Val Lys Gly Ile Arg Pro
385                 390                 395                 400
Gly Ala Tyr Cys Glu Pro Lys Met Thr Ser Val Gly Ser Gln Asp Thr
                405                 410                 415
Thr Gly Pro Met Thr Arg Asp Glu Leu Lys Asp Leu Ala Cys Leu Gly
```

```
                420                 425                 430
Phe Ser Ala Asp Leu Val Met Gln Ser Phe Cys His Thr Ala Ala Tyr
        435                 440                 445

Pro Lys Pro Val Asp Val Asn Thr His His Thr Leu Pro Asp Phe Ile
        450                 455                 460

Met Asn Arg Gly Gly Val Ser Leu Arg Pro Asp Gly Val Ile His
465                 470                 475                 480

Ser Trp Leu Asn Arg Met Leu Leu Pro Asp Thr Val Gly Thr Gly Gly
                485                 490                 495

Asp Ser His Thr Arg Phe Pro Ile Gly Ile Ser Phe Pro Ala Gly Ser
                500                 505                 510

Gly Leu Val Ala Phe Ala Ala Thr Gly Val Met Pro Leu Asp Met
            515                 520                 525

Pro Glu Ser Val Leu Val Arg Phe Lys Gly Lys Met Gln Pro Gly Ile
        530                 535                 540

Thr Leu Arg Asp Leu Val His Ala Ile Pro Leu Tyr Ala Ile Lys Gln
545                 550                 555                 560

Gly Leu Leu Thr Val Glu Lys Lys Gly Lys Lys Asn Ile Phe Ser Gly
                565                 570                 575

Arg Ile Leu Glu Ile Glu Gly Leu Pro Asp Leu Lys Val Glu Gln Ala
                580                 585                 590

Phe Glu Leu Thr Asp Ala Ser Ala Glu Arg Ser Ala Ala Gly Cys Thr
                595                 600                 605

Ile Lys Leu Asn Lys Glu Pro Ile Ile Glu Tyr Leu Asn Ser Asn Ile
            610                 615                 620

Val Leu Leu Lys Trp Met Ile Ala Glu Gly Tyr Gly Asp Arg Arg Thr
625                 630                 635                 640

Leu Glu Arg Arg Ile Gln Gly Met Glu Lys Trp Leu Ala Asn Pro Glu
                645                 650                 655

Leu Leu Glu Ala Asp Ala Asp Ala Glu Tyr Ala Ala Val Ile Asp Ile
                660                 665                 670

Asp Leu Ala Asp Ile Lys Glu Pro Ile Leu Cys Ala Pro Asn Asp Pro
            675                 680                 685

Asp Asp Ala Arg Pro Leu Ser Ala Val Gln Gly Glu Lys Ile Asp Glu
        690                 695                 700

Val Phe Ile Gly Ser Cys Met Thr Asn Ile Gly His Phe Arg Ala Ala
705                 710                 715                 720

Gly Lys Leu Leu Asp Ala His Lys Gly Gln Leu Pro Thr Arg Leu Trp
                725                 730                 735

Val Ala Pro Pro Thr Arg Met Asp Ala Ala Gln Leu Thr Glu Glu Gly
                740                 745                 750

Tyr Tyr Ser Val Phe Gly Lys Ser Gly Ala Arg Ile Glu Ile Pro Gly
            755                 760                 765

Cys Ser Leu Cys Met Gly Asn Gln Ala Arg Val Ala Asp Gly Ala Thr
        770                 775                 780

Val Val Ser Thr Ser Thr Arg Asn Phe Pro Asn Arg Leu Gly Thr Gly
785                 790                 795                 800

Ala Asn Val Phe Leu Ala Ser Ala Glu Leu Ala Val Ala Ala Leu
                805                 810                 815

Ile Gly Lys Leu Pro Thr Pro Glu Glu Tyr Gln Thr Tyr Val Ala Gln
                820                 825                 830

Val Asp Lys Thr Ala Val Asp Thr Tyr Arg Tyr Leu Asn Phe Asn Gln
                835                 840                 845
```

<210> SEQ ID NO 7
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 7

Glu Phe Gly Pro Gly Pro Gly Pro Gly Pro Leu Glu Val Leu
1               5                   10                  15

Phe Gln Gly Pro Gly Arg Ala Lys Leu
            20                  25

<210> SEQ ID NO 8
<211> LENGTH: 4224
<212> TYPE: DNA
<213> ORGANISM: Artificial sequence
<220> FEATURE:
<223> OTHER INFORMATION: fusion polypeptide
<220> FEATURE:
<221> NAME/KEY: CDS
<222> LOCATION: (1)..(4224)

<400> SEQUENCE: 8

```
atg acc aag cag tct gct gat tcc aac gcg aag tct ggt gtg acc tct      48
Met Thr Lys Gln Ser Ala Asp Ser Asn Ala Lys Ser Gly Val Thr Ser
1               5                   10                  15 gag atc tgt cac tgg gcg tct aat ctc gcc act gat gat atc ccg agc      96
Glu Ile Cys His Trp Ala Ser Asn Leu Ala Thr Asp Asp Ile Pro Ser
                20                  25                  30 gac gtt ctg gag cgt gca aaa tac ctg atc ctg gat ggt atc gcg tgc     144
Asp Val Leu Glu Arg Ala Lys Tyr Leu Ile Leu Asp Gly Ile Ala Cys
        35                  40                  45 gcg tgg gta ggt gct cgt gtc cca tgg tct gaa aaa tac gtt caa gcg     192
Ala Trp Val Gly Ala Arg Val Pro Trp Ser Glu Lys Tyr Val Gln Ala
    50                  55                  60 acc atg tct ttc gaa cct ccg ggt gcg tgt cgt gtc atc ggt tac ggc     240
Thr Met Ser Phe Glu Pro Pro Gly Ala Cys Arg Val Ile Gly Tyr Gly
65              70                  75                  80 cag aaa ctg ggt ccg gta gcg gct gcc atg acg aac tct gca ttt att     288
Gln Lys Leu Gly Pro Val Ala Ala Ala Met Thr Asn Ser Ala Phe Ile
                85                  90                  95 cag gcg acc gaa ctc gat gac tat cac tct gaa gcg ccg ctg cat tcc     336
Gln Ala Thr Glu Leu Asp Asp Tyr His Ser Glu Ala Pro Leu His Ser
            100                 105                 110 gcg tct atc gtt ctc ccg gca gtt ttc gcg gcg agc gaa gta ctg gcc     384
Ala Ser Ile Val Leu Pro Ala Val Phe Ala Ala Ser Glu Val Leu Ala
        115                 120                 125 gaa cag ggt aaa acc atc tct ggt att gac gtg att ctg gct gcg atc     432
Glu Gln Gly Lys Thr Ile Ser Gly Ile Asp Val Ile Leu Ala Ala Ile
    130                 135                 140 gtt ggt ttc gag agc ggt cct cgc atc ggc aaa gcg atc tac ggt tct     480
Val Gly Phe Glu Ser Gly Pro Arg Ile Gly Lys Ala Ile Tyr Gly Ser
145             150                 155                 160 gac ctc ctg aac aac ggc tgg cac tgc ggt gcg gta tat ggc gca ccg     528
Asp Leu Leu Asn Asn Gly Trp His Cys Gly Ala Val Tyr Gly Ala Pro
                165                 170                 175
```

```
gct ggt gcg ctc gca act ggt aag ctc ctg ggc ctc acg ccg gac agc    576
Ala Gly Ala Leu Ala Thr Gly Lys Leu Leu Gly Leu Thr Pro Asp Ser
            180                 185                 190 atg gaa gat gca ctg ggt att gcc tgc acg caa gca tgc ggc ctc atg    624
Met Glu Asp Ala Leu Gly Ile Ala Cys Thr Gln Ala Cys Gly Leu Met
        195                 200                 205 tcc gcg cag tat ggt ggc atg gtt aaa cgt gtt cag cac ggt ttc gca    672
Ser Ala Gln Tyr Gly Gly Met Val Lys Arg Val Gln His Gly Phe Ala
    210                 215                 220 gcg cgt aat ggt ctc ctc ggt ggc ctc ctg gct cac ggc ggc tac gag    720
Ala Arg Asn Gly Leu Leu Gly Gly Leu Leu Ala His Gly Gly Tyr Glu
225                 230                 235                 240 gcg atg aaa ggt gtt ctc gag cgt tct tac ggt ggc ttc ctg aag atg    768
Ala Met Lys Gly Val Leu Glu Arg Ser Tyr Gly Gly Phe Leu Lys Met
                245                 250                 255 ttc acc aag ggc aac ggt cgt gaa ccg ccg tac aaa gaa gaa gag gtt    816
Phe Thr Lys Gly Asn Gly Arg Glu Pro Pro Tyr Lys Glu Glu Glu Val
            260                 265                 270 gtg gct ggt ctg ggt agc ttc tgg cac acc ttc acc att cgt atc aaa    864
Val Ala Gly Leu Gly Ser Phe Trp His Thr Phe Thr Ile Arg Ile Lys
        275                 280                 285 ctg tac gcg tgc tgc ggt ctc gta cac ggt cct gtt gaa gcc att gaa    912
Leu Tyr Ala Cys Cys Gly Leu Val His Gly Pro Val Glu Ala Ile Glu
    290                 295                 300 aac ctc cag ggt cgt tac ccg gaa ctg ctc aat cgt gct aac ctg tct    960
Asn Leu Gln Gly Arg Tyr Pro Glu Leu Leu Asn Arg Ala Asn Leu Ser
305                 310                 315                 320 aac atc cgc cac gtt cac gta caa ctc tct acc gcg agc aac tcc cac   1008
Asn Ile Arg His Val His Val Gln Leu Ser Thr Ala Ser Asn Ser His
                325                 330                 335 tgt ggt tgg atc cca gaa gag cgc cca atc tct tct atc gcg ggt caa   1056
Cys Gly Trp Ile Pro Glu Glu Arg Pro Ile Ser Ser Ile Ala Gly Gln
            340                 345                 350 atg tct gtc gca tat atc ctc gcc gtt cag ctc gtt gac caa cag tgt   1104
Met Ser Val Ala Tyr Ile Leu Ala Val Gln Leu Val Asp Gln Gln Cys
        355                 360                 365 ctg ctc agc cag ttc tcc gag ttt gac gat aat ctg gaa cgc ccg gaa   1152
Leu Leu Ser Gln Phe Ser Glu Phe Asp Asp Asn Leu Glu Arg Pro Glu
    370                 375                 380 gtg tgg gac ctg gca cgt aag gtt acc agc tct caa tct gag gag ttc   1200
Val Trp Asp Leu Ala Arg Lys Val Thr Ser Ser Gln Ser Glu Glu Phe
385                 390                 395                 400 gac cag gac ggt aac tgt ctc tct gcc ggt cgc gtc cgt att gag ttc   1248
Asp Gln Asp Gly Asn Cys Leu Ser Ala Gly Arg Val Arg Ile Glu Phe
                405                 410                 415 aac gac ggc tcc tcc atc acc gaa tcc gtt gag aag ccg ctc ggt gta   1296
Asn Asp Gly Ser Ser Ile Thr Glu Ser Val Glu Lys Pro Leu Gly Val
            420                 425                 430 aag gaa cca atg cca aat gaa cgc atc ctg cac aaa tac cgt acc ctg   1344
Lys Glu Pro Met Pro Asn Glu Arg Ile Leu His Lys Tyr Arg Thr Leu
        435                 440                 445 gcg ggt tct gta acg gac gaa agc cgt gtt aag gag atc gag gat ctc   1392
Ala Gly Ser Val Thr Asp Glu Ser Arg Val Lys Glu Ile Glu Asp Leu
    450                 455                 460 gtg ctc ggc ctg gac cgt ctg acc gat att agc ccg ctc ctc gag ctg   1440
Val Leu Gly Leu Asp Arg Leu Thr Asp Ile Ser Pro Leu Leu Glu Leu
465                 470                 475                 480 ctg aat tgt ccg gtt aaa tcc cca ctg ggt att gaa ttt ggt ccg ggt   1488
Leu Asn Cys Pro Val Lys Ser Pro Leu Gly Ile Glu Phe Gly Pro Gly
```

```
                     485                 490                 495
cca ggt cct ggt cct ggc cct cta gaa gtg ttg ttc caa ggt cct ggt    1536
Pro Gly Pro Gly Pro Gly Pro Leu Glu Val Leu Phe Gln Gly Pro Gly
            500                 505                 510 cgt gcg aaa ctc atg tcg tca acc cta cga gaa gcc agt aag gac acg    1584
Arg Ala Lys Leu Met Ser Ser Thr Leu Arg Glu Ala Ser Lys Asp Thr
            515                 520                 525 ttg cag gcc aaa gat aaa act tac cac tac tac agc ctg ccg ctt gct    1632
Leu Gln Ala Lys Asp Lys Thr Tyr His Tyr Tyr Ser Leu Pro Leu Ala
        530                 535                 540 gct aaa tca ctg ggc gat atc acc cgt cta ccc aag tca ctc aaa gtt    1680
Ala Lys Ser Leu Gly Asp Ile Thr Arg Leu Pro Lys Ser Leu Lys Val
545                 550                 555                 560 ttg ctc gaa aac ctg ctg cgc tgg cag gat ggt aac tcg gtt acc gaa    1728
Leu Leu Glu Asn Leu Leu Arg Trp Gln Asp Gly Asn Ser Val Thr Glu
                565                 570                 575 gag gat atc cac gcg ctg gca gga tgg ctg aaa aat gcc cat gct gac    1776
Glu Asp Ile His Ala Leu Ala Gly Trp Leu Lys Asn Ala His Ala Asp
            580                 585                 590 cgt gaa att gcc tac cgc ccg gca agg gtg ctg atg cag gac ttt acc    1824
Arg Glu Ile Ala Tyr Arg Pro Ala Arg Val Leu Met Gln Asp Phe Thr
            595                 600                 605 ggc gta cct gcc gtt gtt gat ctg gcg gca atg cgc gaa gcg gtt aaa    1872
Gly Val Pro Ala Val Val Asp Leu Ala Ala Met Arg Glu Ala Val Lys
        610                 615                 620 cgc ctc ggc ggc gat act gca aag gtt aac ccg ctc tca ccg gtc gac    1920
Arg Leu Gly Gly Asp Thr Ala Lys Val Asn Pro Leu Ser Pro Val Asp
625                 630                 635                 640 ctg gtc att gac cac tcg gtg acc gtc gat cgt ttt ggt gat gat gag    1968
Leu Val Ile Asp His Ser Val Thr Val Asp Arg Phe Gly Asp Asp Glu
                645                 650                 655 gca ttt gaa gaa aac gta cgc ctg gaa atg gag cgc aac cac gaa cgt    2016
Ala Phe Glu Glu Asn Val Arg Leu Glu Met Glu Arg Asn His Glu Arg
            660                 665                 670 tat gtg ttc ctg aaa tgg gga aag caa gcg ttc agt cgg ttt agc gtc    2064
Tyr Val Phe Leu Lys Trp Gly Lys Gln Ala Phe Ser Arg Phe Ser Val
            675                 680                 685 gtg ccg cca ggc aca ggc att tgc cat cag gtt aac ctc gaa tat ctc    2112
Val Pro Pro Gly Thr Gly Ile Cys His Gln Val Asn Leu Glu Tyr Leu
        690                 695                 700 ggc aaa gca gtg tgg agt gaa ttg cag gac ggt gaa tgg att gct tat    2160
Gly Lys Ala Val Trp Ser Glu Leu Gln Asp Gly Glu Trp Ile Ala Tyr
705                 710                 715                 720 ccg gat aca ctc gtt ggt act gac tcg cac acc acc atg atc aac ggc    2208
Pro Asp Thr Leu Val Gly Thr Asp Ser His Thr Thr Met Ile Asn Gly
                725                 730                 735 ctt ggc gtg ctg ggg tgg ggc gtt ggt ggg atc gaa gca gaa gcc gca    2256
Leu Gly Val Leu Gly Trp Gly Val Gly Gly Ile Glu Ala Glu Ala Ala
            740                 745                 750 atg tta ggc cag ccg gtt tcc atg ctt atc ccg gat gta gtg ggc ttc    2304
Met Leu Gly Gln Pro Val Ser Met Leu Ile Pro Asp Val Val Gly Phe
            755                 760                 765 aaa ctt acc gga aaa tta cgt gaa ggt att acc gcc aca gac ctg gtt    2352
Lys Leu Thr Gly Lys Leu Arg Glu Gly Ile Thr Ala Thr Asp Leu Val
        770                 775                 780 ctc act gtt acc caa atg ctg cgc aaa cat ggc gtg gtg ggg aaa ttc    2400
Leu Thr Val Thr Gln Met Leu Arg Lys His Gly Val Val Gly Lys Phe
785                 790                 795                 800 gtc gaa ttt tat ggt gat ggt ctg gat tca cta ccg ttg gcg gat cgc    2448
Val Glu Phe Tyr Gly Asp Gly Leu Asp Ser Leu Pro Leu Ala Asp Arg
```

```
Val Glu Phe Tyr Gly Asp Gly Leu Asp Ser Leu Pro Leu Ala Asp Arg
            805                 810                 815 gcc acc att gcc aat atg tcg cca gaa tat ggt gcc acc tgt ggc ttc       2496
Ala Thr Ile Ala Asn Met Ser Pro Glu Tyr Gly Ala Thr Cys Gly Phe
820                 825                 830 ttc cca atc gat gct gta acc ctc gat tac atg cgt tta agc ggg cgc       2544
Phe Pro Ile Asp Ala Val Thr Leu Asp Tyr Met Arg Leu Ser Gly Arg
        835                 840                 845 agc gaa gat cag gtc gag ttg gtc gaa aaa tat gcc aaa gcg cag ggc       2592
Ser Glu Asp Gln Val Glu Leu Val Glu Lys Tyr Ala Lys Ala Gln Gly
850                 855                 860 atg tgg cgt aac ccg ggc gat gaa cca att ttt acc agt acg tta gaa       2640
Met Trp Arg Asn Pro Gly Asp Glu Pro Ile Phe Thr Ser Thr Leu Glu
865                 870                 875                 880 ctg gat atg aat gac gtt gaa gcg agc ctg gca ggg cct aaa cgc cca       2688
Leu Asp Met Asn Asp Val Glu Ala Ser Leu Ala Gly Pro Lys Arg Pro
            885                 890                 895 cag gat cgc gtt gca ctg ccc gat gta cca aaa gca ttt gcc gcc agt       2736
Gln Asp Arg Val Ala Leu Pro Asp Val Pro Lys Ala Phe Ala Ala Ser
        900                 905                 910 aac gaa ctg gaa gtg aat gcc acg cat aaa gat cgc cag ccg gtc gat       2784
Asn Glu Leu Glu Val Asn Ala Thr His Lys Asp Arg Gln Pro Val Asp
915                 920                 925 tat gtt atg aac gga cat cag tat cag tta cct gat ggc gct gtg gtc       2832
Tyr Val Met Asn Gly His Gln Tyr Gln Leu Pro Asp Gly Ala Val Val
930                 935                 940 att gct gcg ata acc tcg tgc acc aac acc tct aac cca agt gtg ctg       2880
Ile Ala Ala Ile Thr Ser Cys Thr Asn Thr Ser Asn Pro Ser Val Leu
945                 950                 955                 960 atg gcc gca ggc ttg ctg gcg aaa aaa gcc gta act ctg ggc ctc aag       2928
Met Ala Ala Gly Leu Leu Ala Lys Lys Ala Val Thr Leu Gly Leu Lys
            965                 970                 975 cgg caa cca tgg gtc aaa gcg tcg ctg gca ccg ggt tcg aaa gtc gtt       2976
Arg Gln Pro Trp Val Lys Ala Ser Leu Ala Pro Gly Ser Lys Val Val
        980                 985                 990 tct gat tat ctg gca aaa gcg aaa ctg aca ccg tat ctc gac gaa ctg       3024
Ser Asp Tyr Leu Ala Lys Ala Lys Leu Thr Pro Tyr Leu Asp Glu Leu
            995                 1000                1005 ggg ttt aac ctt gtg gga tac ggt tgt acc acc tgt att ggt aac          3069
Gly Phe Asn Leu Val Gly Tyr Gly Cys Thr Thr Cys Ile Gly Asn
    1010                1015                1020 tct ggg ccg ctg ccc gat cct atc gaa acg gca atc aaa aaa agc          3114
Ser Gly Pro Leu Pro Asp Pro Ile Glu Thr Ala Ile Lys Lys Ser
    1025                1030                1035 gat tta acc gtc ggt gcg gtg ctg tcc ggc aac cgt aac ttt gaa          3159
Asp Leu Thr Val Gly Ala Val Leu Ser Gly Asn Arg Asn Phe Glu
    1040                1045                1050 ggc cgt atc cat ccg ctg gtt aaa act aac tgg ctg gcc tcg ccg          3204
Gly Arg Ile His Pro Leu Val Lys Thr Asn Trp Leu Ala Ser Pro
    1055                1060                1065 ccg ctg gtg gtt gcc tat gcg ctg gcg gga aat atg aat atc aac          3249
Pro Leu Val Val Ala Tyr Ala Leu Ala Gly Asn Met Asn Ile Asn
    1070                1075                1080 ctg gct tct gag cct atc ggc cat gat cgc aaa ggc gat ccg gtt          3294
Leu Ala Ser Glu Pro Ile Gly His Asp Arg Lys Gly Asp Pro Val
    1085                1090                1095 tat ctg aaa gat atc tgg cca tcg gca caa gaa att gcc cgt gcg          3339
Tyr Leu Lys Asp Ile Trp Pro Ser Ala Gln Glu Ile Ala Arg Ala
    1100                1105                1110
```

| | | | | | | | | | | | | |
|---|---|---|---|---|---|---|---|---|---|---|---|---|
| gta | gaa | caa | gtc | tcc | aca | gaa | atg | ttc | cgc | aaa | gag | tac gca gaa | 3384 |
| Val | Glu | Gln | Val | Ser | Thr | Glu | Met | Phe | Arg | Lys | Glu | Tyr Ala Glu |
| 1115 | | | | 1120 | | | | | 1125 | | | |
| gtt | ttt | gaa | ggc | aca | gca | gag | tgg | aag | gga | att | aac | gtc aca cga | 3429 |
| Val | Phe | Glu | Gly | Thr | Ala | Glu | Trp | Lys | Gly | Ile | Asn | Val Thr Arg |
| 1130 | | | | 1135 | | | | | 1140 | | | |
| tcc | gat | acc | tac | ggt | tgg | cag | gag | gac | tca | acc | tat | att cgc tta | 3474 |
| Ser | Asp | Thr | Tyr | Gly | Trp | Gln | Glu | Asp | Ser | Thr | Tyr | Ile Arg Leu |
| 1145 | | | | 1150 | | | | | 1155 | | | |
| tcg | cct | ttc | ttt | gat | gaa | atg | cag | gca | aca | cca | gca | cca gtg gaa | 3519 |
| Ser | Pro | Phe | Phe | Asp | Glu | Met | Gln | Ala | Thr | Pro | Ala | Pro Val Glu |
| 1160 | | | | 1165 | | | | | 1170 | | | |
| gat | att | cac | ggt | gcg | cgg | atc | ctc | gca | atg | ctg | ggg | gat tca gtc | 3564 |
| Asp | Ile | His | Gly | Ala | Arg | Ile | Leu | Ala | Met | Leu | Gly | Asp Ser Val |
| 1175 | | | | 1180 | | | | | 1185 | | | |
| acc | act | gac | cat | atc | tct | ccg | gcg | ggc | agt | att | aag | ccc gac agc | 3609 |
| Thr | Thr | Asp | His | Ile | Ser | Pro | Ala | Gly | Ser | Ile | Lys | Pro Asp Ser |
| 1190 | | | | 1195 | | | | | 1200 | | | |
| cca | gcg | ggt | cga | tat | cta | caa | ggt | cgg | ggt | gtt | gag | cga aaa gac | 3654 |
| Pro | Ala | Gly | Arg | Tyr | Leu | Gln | Gly | Arg | Gly | Val | Glu | Arg Lys Asp |
| 1205 | | | | 1210 | | | | | 1215 | | | |
| ttt | aac | tcc | tac | ggt | tcg | cgg | cgt | ggt | aac | cat | gaa | gtg atg atg | 3699 |
| Phe | Asn | Ser | Tyr | Gly | Ser | Arg | Arg | Gly | Asn | His | Glu | Val Met Met |
| 1220 | | | | 1225 | | | | | 1230 | | | |
| cgc | ggc | acc | ttc | gcc | aat | att | cgc | atc | cgt | aat | gaa | atg gtg cct | 3744 |
| Arg | Gly | Thr | Phe | Ala | Asn | Ile | Arg | Ile | Arg | Asn | Glu | Met Val Pro |
| 1235 | | | | 1240 | | | | | 1245 | | | |
| ggc | gtt | gaa | ggg | ggg | atg | acg | cgg | cat | tta | cct | gac | agc gac gta | 3789 |
| Gly | Val | Glu | Gly | Gly | Met | Thr | Arg | His | Leu | Pro | Asp | Ser Asp Val |
| 1250 | | | | 1255 | | | | | 1260 | | | |
| gtc | tct | att | tat | gat | gct | gcg | atg | cgc | tat | aag | cag | gag caa acg | 3834 |
| Val | Ser | Ile | Tyr | Asp | Ala | Ala | Met | Arg | Tyr | Lys | Gln | Glu Gln Thr |
| 1265 | | | | 1270 | | | | | 1275 | | | |
| ccg | ctg | gcg | gtg | att | gcc | ggg | aaa | gag | tat | gga | tca | ggc tcc agt | 3879 |
| Pro | Leu | Ala | Val | Ile | Ala | Gly | Lys | Glu | Tyr | Gly | Ser | Gly Ser Ser |
| 1280 | | | | 1285 | | | | | 1290 | | | |
| cgt | gac | tgg | gcg | gca | aaa | ggt | ccg | cgt | ctg | ctt | ggt | att cgt gtg | 3924 |
| Arg | Asp | Trp | Ala | Ala | Lys | Gly | Pro | Arg | Leu | Leu | Gly | Ile Arg Val |
| 1295 | | | | 1300 | | | | | 1305 | | | |
| gtg | att | gcc | gaa | tcg | ttt | gaa | cga | att | cac | cgt | tcg | aat tta att | 3969 |
| Val | Ile | Ala | Glu | Ser | Phe | Glu | Arg | Ile | His | Arg | Ser | Asn Leu Ile |
| 1310 | | | | 1315 | | | | | 1320 | | | |
| ggc | atg | ggc | atc | ctg | ccg | ctg | gaa | ttt | ccg | caa | ggc | gta acg cgt | 4014 |
| Gly | Met | Gly | Ile | Leu | Pro | Leu | Glu | Phe | Pro | Gln | Gly | Val Thr Arg |
| 1325 | | | | 1330 | | | | | 1335 | | | |
| aaa | acg | tta | ggg | cta | acc | ggg | gaa | gag | aag | att | gat | att ggc gat | 4059 |
| Lys | Thr | Leu | Gly | Leu | Thr | Gly | Glu | Glu | Lys | Ile | Asp | Ile Gly Asp |
| 1340 | | | | 1345 | | | | | 1350 | | | |
| ctg | caa | aac | cta | caa | ccc | ggc | gcg | acg | gtt | ccg | gtg | acg ctt acg | 4104 |
| Leu | Gln | Asn | Leu | Gln | Pro | Gly | Ala | Thr | Val | Pro | Val | Thr Leu Thr |
| 1355 | | | | 1360 | | | | | 1365 | | | |
| cgc | gcg | gat | ggt | agc | cag | gaa | gtc | gta | ccc | tgc | cgt | tgt cgt atc | 4149 |
| Arg | Ala | Asp | Gly | Ser | Gln | Glu | Val | Val | Pro | Cys | Arg | Cys Arg Ile |
| 1370 | | | | 1375 | | | | | 1380 | | | |
| gac | acc | gcg | acg | gag | ttg | acc | tac | tac | cag | aac | gac | ggc att ttg | 4194 |
| Asp | Thr | Ala | Thr | Glu | Leu | Thr | Tyr | Tyr | Gln | Asn | Asp | Gly Ile Leu |
| 1385 | | | | 1390 | | | | | 1395 | | | |
| cat | tat | gtc | att | cgt | aat | atg | ttg | aag | taa | | | | 4224 |
| His | Tyr | Val | Ile | Arg | Asn | Met | Leu | Lys | | | | |
| 1400 | | | | 1405 | | | | | | | | |

<210> SEQ ID NO 9
<211> LENGTH: 1407
<212> TYPE: PRT
<213> ORGANISM: Artificial sequence
<220> FEATURE:
<223> OTHER INFORMATION: Synthetic Construct

<400> SEQUENCE: 9

```
Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Met Thr Asn Ser Ala Phe Ile
            85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
    290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
        355                 360                 365
```

```
Leu Leu Ser Gln Phe Ser Glu Phe Asp Asp Asn Leu Glu Arg Pro Glu
    370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Ile Thr Glu Ser Val Glu Lys Pro Leu Gly Val
                420                 425                 430

Lys Glu Pro Met Pro Asn Glu Arg Ile Leu His Lys Tyr Arg Thr Leu
            435                 440                 445

Ala Gly Ser Val Thr Asp Glu Ser Arg Val Lys Glu Ile Glu Asp Leu
    450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Gly Ile Glu Phe Gly Pro Gly
                485                 490                 495

Pro Gly Pro Gly Pro Gly Pro Leu Glu Val Leu Phe Gln Gly Pro Gly
                500                 505                 510

Arg Ala Lys Leu Met Ser Ser Thr Leu Arg Glu Ala Ser Lys Asp Thr
            515                 520                 525

Leu Gln Ala Lys Asp Lys Thr Tyr His Tyr Tyr Ser Leu Pro Leu Ala
    530                 535                 540

Ala Lys Ser Leu Gly Asp Ile Thr Arg Leu Pro Lys Ser Leu Lys Val
545                 550                 555                 560

Leu Leu Glu Asn Leu Leu Arg Trp Gln Asp Gly Asn Ser Val Thr Glu
                565                 570                 575

Glu Asp Ile His Ala Leu Ala Gly Trp Leu Lys Asn Ala His Ala Asp
            580                 585                 590

Arg Glu Ile Ala Tyr Arg Pro Ala Arg Val Leu Met Gln Asp Phe Thr
    595                 600                 605

Gly Val Pro Ala Val Val Asp Leu Ala Ala Met Arg Glu Ala Val Lys
610                 615                 620

Arg Leu Gly Gly Asp Thr Ala Lys Val Asn Pro Leu Ser Pro Val Asp
625                 630                 635                 640

Leu Val Ile Asp His Ser Val Thr Val Asp Arg Phe Gly Asp Asp Glu
                645                 650                 655

Ala Phe Glu Glu Asn Val Arg Leu Glu Met Glu Arg Asn His Glu Arg
            660                 665                 670

Tyr Val Phe Leu Lys Trp Gly Lys Gln Ala Phe Ser Arg Phe Ser Val
    675                 680                 685

Val Pro Pro Gly Thr Gly Ile Cys His Gln Val Asn Leu Glu Tyr Leu
690                 695                 700

Gly Lys Ala Val Trp Ser Glu Leu Gln Asp Gly Glu Trp Ile Ala Tyr
705                 710                 715                 720

Pro Asp Thr Leu Val Gly Thr Asp Ser His Thr Thr Met Ile Asn Gly
                725                 730                 735

Leu Gly Val Leu Gly Trp Gly Val Gly Gly Ile Glu Ala Glu Ala Ala
            740                 745                 750

Met Leu Gly Gln Pro Val Ser Met Leu Ile Pro Asp Val Val Gly Phe
    755                 760                 765

Lys Leu Thr Gly Lys Leu Arg Glu Gly Ile Thr Ala Thr Asp Leu Val
770                 775                 780
```

```
Leu Thr Val Thr Gln Met Leu Arg Lys His Gly Val Val Gly Lys Phe
785                 790                 795                 800

Val Glu Phe Tyr Gly Asp Gly Leu Asp Ser Leu Pro Leu Ala Asp Arg
                805                 810                 815

Ala Thr Ile Ala Asn Met Ser Pro Glu Tyr Gly Ala Thr Cys Gly Phe
            820                 825                 830

Phe Pro Ile Asp Ala Val Thr Leu Asp Tyr Met Arg Leu Ser Gly Arg
        835                 840                 845

Ser Glu Asp Gln Val Glu Leu Val Glu Lys Tyr Ala Lys Ala Gln Gly
    850                 855                 860

Met Trp Arg Asn Pro Gly Asp Glu Pro Ile Phe Thr Ser Thr Leu Glu
865                 870                 875                 880

Leu Asp Met Asn Asp Val Glu Ala Ser Leu Ala Gly Pro Lys Arg Pro
                885                 890                 895

Gln Asp Arg Val Ala Leu Pro Asp Val Pro Lys Ala Phe Ala Ala Ser
            900                 905                 910

Asn Glu Leu Glu Val Asn Ala Thr His Lys Asp Arg Gln Pro Val Asp
        915                 920                 925

Tyr Val Met Asn Gly His Gln Tyr Gln Leu Pro Asp Gly Ala Val Val
    930                 935                 940

Ile Ala Ala Ile Thr Ser Cys Thr Asn Thr Ser Asn Pro Ser Val Leu
945                 950                 955                 960

Met Ala Ala Gly Leu Leu Ala Lys Lys Ala Val Thr Leu Gly Leu Lys
                965                 970                 975

Arg Gln Pro Trp Val Lys Ala Ser Leu Ala Pro Gly Ser Lys Val Val
            980                 985                 990

Ser Asp Tyr Leu Ala Lys Ala Lys  Leu Thr Pro Tyr Leu  Asp Glu Leu
        995                 1000                1005

Gly Phe  Asn Leu Val Gly Tyr  Gly Cys Thr Thr Cys  Ile Gly Asn
    1010                1015                1020

Ser Gly  Pro Leu Pro Asp Pro  Ile Glu Thr Ala Ile  Lys Lys Ser
    1025                1030                1035

Asp Leu  Thr Val Gly Ala Val  Leu Ser Gly Asn Arg  Asn Phe Glu
    1040                1045                1050

Gly Arg  Ile His Pro Leu Val  Lys Thr Asn Trp Leu  Ala Ser Pro
    1055                1060                1065

Pro Leu  Val Val Ala Tyr Ala  Leu Ala Gly Asn Met  Asn Ile Asn
    1070                1075                1080

Leu Ala  Ser Glu Pro Ile Gly  His Asp Arg Lys Gly  Asp Pro Val
    1085                1090                1095

Tyr Leu  Lys Asp Ile Trp Pro  Ser Ala Gln Glu Ile  Ala Arg Ala
    1100                1105                1110

Val Glu  Gln Val Ser Thr Glu  Met Phe Arg Lys Glu  Tyr Ala Glu
    1115                1120                1125

Val Phe  Glu Gly Thr Ala Glu  Trp Lys Gly Ile Asn  Val Thr Arg
    1130                1135                1140

Ser Asp  Thr Tyr Gly Trp Gln  Glu Asp Ser Thr Tyr  Ile Arg Leu
    1145                1150                1155

Ser Pro  Phe Phe Asp Glu Met  Gln Ala Thr Pro Ala  Pro Val Glu
    1160                1165                1170

Asp Ile  His Gly Ala Arg Ile  Leu Ala Met Leu Gly  Asp Ser Val
    1175                1180                1185

Thr Thr  Asp His Ile Ser Pro  Ala Gly Ser Ile Lys  Pro Asp Ser
```

```
                    1190               1195               1200

Pro Ala Gly Arg Tyr Leu Gln Gly Arg Gly Val Glu Arg Lys Asp
        1205                1210                1215

Phe Asn Ser Tyr Gly Ser Arg Arg Gly Asn His Glu Val Met Met
        1220                1225                1230

Arg Gly Thr Phe Ala Asn Ile Arg Ile Arg Asn Glu Met Val Pro
        1235                1240                1245

Gly Val Glu Gly Gly Met Thr Arg His Leu Pro Asp Ser Asp Val
        1250                1255                1260

Val Ser Ile Tyr Asp Ala Ala Met Arg Tyr Lys Gln Glu Gln Thr
        1265                1270                1275

Pro Leu Ala Val Ile Ala Gly Lys Glu Tyr Gly Ser Gly Ser Ser
        1280                1285                1290

Arg Asp Trp Ala Ala Lys Gly Pro Arg Leu Leu Gly Ile Arg Val
        1295                1300                1305

Val Ile Ala Glu Ser Phe Glu Arg Ile His Arg Ser Asn Leu Ile
        1310                1315                1320

Gly Met Gly Ile Leu Pro Leu Glu Phe Pro Gln Gly Val Thr Arg
        1325                1330                1335

Lys Thr Leu Gly Leu Thr Gly Glu Glu Lys Ile Asp Ile Gly Asp
        1340                1345                1350

Leu Gln Asn Leu Gln Pro Gly Ala Thr Val Pro Val Thr Leu Thr
        1355                1360                1365

Arg Ala Asp Gly Ser Gln Glu Val Val Pro Cys Arg Cys Arg Ile
        1370                1375                1380

Asp Thr Ala Thr Glu Leu Thr Tyr Tyr Gln Asn Asp Gly Ile Leu
        1385                1390                1395

His Tyr Val Ile Arg Asn Met Leu Lys
        1400                1405

<210> SEQ ID NO 10
<211> LENGTH: 4146
<212> TYPE: DNA
<213> ORGANISM: Artificial sequence
<220> FEATURE:
<223> OTHER INFORMATION: fusion polypeptide
<220> FEATURE:
<221> NAME/KEY: CDS
<222> LOCATION: (1)..(4146)

<400> SEQUENCE: 10 atg acc aag cag tct gct gat tcc aac gcg aag tct ggt gtg acc tct      48
Met Thr Lys Gln Ser Ala Asp Ser Asn Ala Lys Ser Gly Val Thr Ser
1               5                   10                  15 gag atc tgt cac tgg gcg tct aat ctc gcc act gat gat atc ccg agc      96
Glu Ile Cys His Trp Ala Ser Asn Leu Ala Thr Asp Asp Ile Pro Ser
            20                  25                  30 gac gtt ctg gag cgt gca aaa tac ctg atc ctg gat ggt atc gcg tgc     144
Asp Val Leu Glu Arg Ala Lys Tyr Leu Ile Leu Asp Gly Ile Ala Cys
        35                  40                  45 gcg tgg gta ggt gct cgt gtc cca tgg tct gaa aaa tac gtt caa gcg     192
Ala Trp Val Gly Ala Arg Val Pro Trp Ser Glu Lys Tyr Val Gln Ala
    50                  55                  60 acc atg tct ttc gaa cct ccg ggt gcg tgt cgt gtc atc ggt tac ggc     240
Thr Met Ser Phe Glu Pro Pro Gly Ala Cys Arg Val Ile Gly Tyr Gly
65                  70                  75                  80 cag aaa ctg ggt ccg gta gcg gct gcc atg acg aac tct gca ttt att     288
Gln Lys Leu Gly Pro Val Ala Ala Ala Met Thr Asn Ser Ala Phe Ile
```

-continued

| | | | | 85 | | | 90 | | | 95 | | | | |
|---|---|---|---|---|---|---|---|---|---|---|---|---|---|---|
| cag | gcg | acc | gaa | ctc | gat | gac | tat | cac | tct | gaa | gcg | ccg | ctg | cat | tcc | 336 |
| Gln | Ala | Thr | Glu | Leu | Asp | Asp | Tyr | His | Ser | Glu | Ala | Pro | Leu | His | Ser |
| | | | 100 | | | | | 105 | | | | | 110 | | |

```
cag gcg acc gaa ctc gat gac tat cac tct gaa gcg ccg ctg cat tcc      336
Gln Ala Thr Glu Leu Asp Asp Tyr His Ser Glu Ala Pro Leu His Ser
            100                 105                 110 gcg tct atc gtt ctc ccg gca gtt ttc gcg gcg agc gaa gta ctg gcc      384
Ala Ser Ile Val Leu Pro Ala Val Phe Ala Ala Ser Glu Val Leu Ala
            115                 120                 125 gaa cag ggt aaa acc atc tct ggt att gac gtg att ctg gct gcg atc      432
Glu Gln Gly Lys Thr Ile Ser Gly Ile Asp Val Ile Leu Ala Ala Ile
        130                 135                 140 gtt ggt ttc gag agc ggt cct cgc atc ggc aaa gcg atc tac ggt tct      480
Val Gly Phe Glu Ser Gly Pro Arg Ile Gly Lys Ala Ile Tyr Gly Ser
145                 150                 155                 160 gac ctc ctg aac aac ggc tgg cac tgc ggt gcg gta tat ggc gca ccg      528
Asp Leu Leu Asn Asn Gly Trp His Cys Gly Ala Val Tyr Gly Ala Pro
                    165                 170                 175 gct ggt gcg ctc gca act ggt aag ctg ctg ggc ctc acg ccg gac agc      576
Ala Gly Ala Leu Ala Thr Gly Lys Leu Leu Gly Leu Thr Pro Asp Ser
            180                 185                 190 atg gaa gat gca ctg ggt att gcc tgc acg caa gca tgc ggc ctc atg      624
Met Glu Asp Ala Leu Gly Ile Ala Cys Thr Gln Ala Cys Gly Leu Met
        195                 200                 205 tcc gcg cag tat ggt ggc atg gtt aaa cgt gtt cag cac ggt ttc gca      672
Ser Ala Gln Tyr Gly Gly Met Val Lys Arg Val Gln His Gly Phe Ala
    210                 215                 220 gcg cgt aat ggt ctc ctc ggt ggc ctg ctg gct cac ggc ggc tac gag      720
Ala Arg Asn Gly Leu Leu Gly Gly Leu Leu Ala His Gly Gly Tyr Glu
225                 230                 235                 240 gcg atg aaa ggt gtt ctc gag cgt tct tac ggt ggc ttc ctg aag atg      768
Ala Met Lys Gly Val Leu Glu Arg Ser Tyr Gly Gly Phe Leu Lys Met
                245                 250                 255 ttc acc aag ggc aac ggt cgt gaa ccg ccg tac aaa gaa gaa gag gtt      816
Phe Thr Lys Gly Asn Gly Arg Glu Pro Pro Tyr Lys Glu Glu Glu Val
            260                 265                 270 gtg gct ggt ctg ggt agc ttc tgg cac acc ttc acc att cgt atc aaa      864
Val Ala Gly Leu Gly Ser Phe Trp His Thr Phe Thr Ile Arg Ile Lys
        275                 280                 285 ctg tac gcg tgc tgc ggt ctc gta cac ggt cct gtt gaa gcc att gaa      912
Leu Tyr Ala Cys Cys Gly Leu Val His Gly Pro Val Glu Ala Ile Glu
    290                 295                 300 aac ctc cag ggt cgt tac ccg gaa ctg ctc aat cgt gct aac ctg tct      960
Asn Leu Gln Gly Arg Tyr Pro Glu Leu Leu Asn Arg Ala Asn Leu Ser
305                 310                 315                 320 aac atc cgc cac gtt cac gta caa ctc tct acc gcg agc aac tcc cac     1008
Asn Ile Arg His Val His Val Gln Leu Ser Thr Ala Ser Asn Ser His
                325                 330                 335 tgt ggt tgg atc cca gaa gag cgc cca atc tct tct atc gcg ggt caa     1056
Cys Gly Trp Ile Pro Glu Glu Arg Pro Ile Ser Ser Ile Ala Gly Gln
            340                 345                 350 atg tct gtc gca tat atc ctc gcc gtt cag ctc gtt gac caa cag tgt     1104
Met Ser Val Ala Tyr Ile Leu Ala Val Gln Leu Val Asp Gln Gln Cys
        355                 360                 365 ctg ctc agc cag ttc tcc gag ttt gac gat aat ctg gaa cgc ccg gaa     1152
Leu Leu Ser Gln Phe Ser Glu Phe Asp Asp Asn Leu Glu Arg Pro Glu
    370                 375                 380 gtg tgg gac ctg gca cgt aag gtt acc agc tct caa tct gag gag ttc     1200
Val Trp Asp Leu Ala Arg Lys Val Thr Ser Ser Gln Ser Glu Glu Phe
385                 390                 395                 400 gac cag gac ggt aac tgt ctc tct gcc ggt cgc gtc cgt att gag ttc     1248
```

|     |     |     |     |     |     |     |     |     |     |     |     |      |
|-----|-----|-----|-----|-----|-----|-----|-----|-----|-----|-----|-----|------|
| Asp | Gln | Asp | Gly | Asn | Cys | Leu | Ser | Ala | Gly | Arg | Val | Arg Ile Glu Phe |
|     |     |     |     | 405 |     |     |     | 410 |     |     |     | 415 |

```
aac gac ggc tcc tcc atc acc gaa tcc gtt gag aag ccg ctc ggt gta   1296
Asn Asp Gly Ser Ser Ile Thr Glu Ser Val Glu Lys Pro Leu Gly Val
            420                 425                 430 aag gaa cca atg cca aat gaa cgc atc ctg cac aaa tac cgt acc ctg   1344
Lys Glu Pro Met Pro Asn Glu Arg Ile Leu His Lys Tyr Arg Thr Leu
        435                 440                 445 gcg ggt tct gta acg gac gaa agc cgt gtt aag gag atc gag gat ctc   1392
Ala Gly Ser Val Thr Asp Glu Ser Arg Val Lys Glu Ile Glu Asp Leu
    450                 455                 460 gtg ctc ggc ctg gac cgt ctg acc gat att agc ccg ctc ctc gag ctg   1440
Val Leu Gly Leu Asp Arg Leu Thr Asp Ile Ser Pro Leu Leu Glu Leu
465                 470                 475                 480 ctg aat tgt ccg gtt aaa tcc cca ctg ggt att gaa ttt ggt ccg ggt   1488
Leu Asn Cys Pro Val Lys Ser Pro Leu Gly Ile Glu Phe Gly Pro Gly
                485                 490                 495 cca ggt cct ggt cct ggc cct cta gaa gtg ttg ttc caa ggt cct ggt   1536
Pro Gly Pro Gly Pro Gly Pro Leu Glu Val Leu Phe Gln Gly Pro Gly
            500                 505                 510 cgt gcg aaa ctc gtg cta gaa gaa tac cgt aag cac gta gct gag cgt   1584
Arg Ala Lys Leu Val Leu Glu Glu Tyr Arg Lys His Val Ala Glu Arg
        515                 520                 525 gcc gct gag ggg att gcg ccc aaa ccc ctg gat gca aac caa atg gcc   1632
Ala Ala Glu Gly Ile Ala Pro Lys Pro Leu Asp Ala Asn Gln Met Ala
    530                 535                 540 gca ctt gta gag ctg ctg aaa aac ccg ccc gcg ggc gaa gaa gaa ttc   1680
Ala Leu Val Glu Leu Leu Lys Asn Pro Pro Ala Gly Glu Glu Glu Phe
545                 550                 555                 560 ctg tta gat ctg tta acc aac cgt gtt ccc cca ggc gtc gat gaa gcc   1728
Leu Leu Asp Leu Leu Thr Asn Arg Val Pro Pro Gly Val Asp Glu Ala
                565                 570                 575 gcc tat gtc aaa gca ggc ttc ctg gct gct atc gcg aaa ggc gaa gcc   1776
Ala Tyr Val Lys Ala Gly Phe Leu Ala Ala Ile Ala Lys Gly Glu Ala
            580                 585                 590 aaa tcc cct ctg ctg act ccg gaa aaa gcc atc gaa ctg ctg ggc acc   1824
Lys Ser Pro Leu Leu Thr Pro Glu Lys Ala Ile Glu Leu Leu Gly Thr
        595                 600                 605 atg cag ggt ggt tac aac att cat ccg ctg atc gac gcg ctg gat gat   1872
Met Gln Gly Gly Tyr Asn Ile His Pro Leu Ile Asp Ala Leu Asp Asp
    610                 615                 620 gcc aaa ctg gca cct att gct gcc aaa gca ctt tct cac acg ctg ctg   1920
Ala Lys Leu Ala Pro Ile Ala Ala Lys Ala Leu Ser His Thr Leu Leu
625                 630                 635                 640 atg ttc gat aac ttc tat gac gta gaa gag aaa gcg aaa gca ggc aac   1968
Met Phe Asp Asn Phe Tyr Asp Val Glu Glu Lys Ala Lys Ala Gly Asn
                645                 650                 655 gaa tat gcg aag cag gtt atg cag tcc tgg gcg gat gcc gaa tgg ttc   2016
Glu Tyr Ala Lys Gln Val Met Gln Ser Trp Ala Asp Ala Glu Trp Phe
            660                 665                 670 ctg aat cgc ccg gcg ctg gct gaa aaa ctg acc gtt act gtc ttc aaa   2064
Leu Asn Arg Pro Ala Leu Ala Glu Lys Leu Thr Val Thr Val Phe Lys
        675                 680                 685 gtc act ggc gaa act aac acc gat gac ctt tct ccg gca ccg gat gcg   2112
Val Thr Gly Glu Thr Asn Thr Asp Asp Leu Ser Pro Ala Pro Asp Ala
    690                 695                 700 tgg tca cgc ccg gat atc cca ctg cac gcg ctg gcg atg ctg aaa aac   2160
Trp Ser Arg Pro Asp Ile Pro Leu His Ala Leu Ala Met Leu Lys Asn
705                 710                 715                 720
```

-continued

```
gcc cgt gaa ggt att gag cca gac cag cct ggt gtt gtt ggt ccg atc       2208
Ala Arg Glu Gly Ile Glu Pro Asp Gln Pro Gly Val Val Gly Pro Ile
            725                 730                 735 aag caa atc gaa gct ctg caa cag aaa ggt ttc ccg ctg gcg tac gtc       2256
Lys Gln Ile Glu Ala Leu Gln Gln Lys Gly Phe Pro Leu Ala Tyr Val
        740                 745                 750 ggt gac gtt gtg ggt acg ggt tct tcg cgt aaa tcc gcc act aac tcc       2304
Gly Asp Val Val Gly Thr Gly Ser Ser Arg Lys Ser Ala Thr Asn Ser
                755                 760                 765 gtt ctg tgg ttt atg ggc gat gat att cca cat gtg ccg aac aaa cgc       2352
Val Leu Trp Phe Met Gly Asp Asp Ile Pro His Val Pro Asn Lys Arg
            770                 775                 780 ggc ggt ggt ttg tgc ctc ggc ggt aaa att gca ccc atc ttc ttt aac       2400
Gly Gly Gly Leu Cys Leu Gly Gly Lys Ile Ala Pro Ile Phe Phe Asn
785                 790                 795                 800 acg atg gaa gac gcg ggt gca ctg cca atc gaa gtc gac gtc tct aac       2448
Thr Met Glu Asp Ala Gly Ala Leu Pro Ile Glu Val Asp Val Ser Asn
                        805                 810                 815 ctg aac atg ggc gac gtg att gac gtt tac ccg tac aaa ggt gaa gtg       2496
Leu Asn Met Gly Asp Val Ile Asp Val Tyr Pro Tyr Lys Gly Glu Val
                820                 825                 830 cgt aac cac gaa acc ggc gaa ctg ctg gcg acc ttc gaa ctg aaa acc       2544
Arg Asn His Glu Thr Gly Glu Leu Leu Ala Thr Phe Glu Leu Lys Thr
            835                 840                 845 gac gtg ctg att gat gaa gtg cgt gct ggt ggc cgt att ccg ctg att       2592
Asp Val Leu Ile Asp Glu Val Arg Ala Gly Gly Arg Ile Pro Leu Ile
850                 855                 860 atc ggg cgt ggc ctg acc acc aaa gcg cgt gaa gca ctt ggt ctg ccg       2640
Ile Gly Arg Gly Leu Thr Thr Lys Ala Arg Glu Ala Leu Gly Leu Pro
865                 870                 875                 880 cac agt gat gtg ttc cgt cag gcg aaa gat gtc gct gag agc gat cgc       2688
His Ser Asp Val Phe Arg Gln Ala Lys Asp Val Ala Glu Ser Asp Arg
                885                 890                 895 ggc ttc tcg ctg gcg caa aaa atg gta ggc cgt gcc tgt ggc gtg aaa       2736
Gly Phe Ser Leu Ala Gln Lys Met Val Gly Arg Ala Cys Gly Val Lys
                900                 905                 910 ggc att cgt ccg ggc gcg tac tgt gaa ccg aaa atg act tct gta ggt       2784
Gly Ile Arg Pro Gly Ala Tyr Cys Glu Pro Lys Met Thr Ser Val Gly
            915                 920                 925 tcc cag gac acc acc ggc ccg atg acc cgt gat gaa ctg aaa gac ctg       2832
Ser Gln Asp Thr Thr Gly Pro Met Thr Arg Asp Glu Leu Lys Asp Leu
        930                 935                 940 gcg tgc ctg ggc ttc tcg gct gac ctg gtg atg cag tct ttc tgc cac       2880
Ala Cys Leu Gly Phe Ser Ala Asp Leu Val Met Gln Ser Phe Cys His
945                 950                 955                 960 acc gcg gcg tat ccg aag cca gtt gac gtg aac acg cac cac acg ctg       2928
Thr Ala Ala Tyr Pro Lys Pro Val Asp Val Asn Thr His His Thr Leu
                965                 970                 975 ccg gac ttc att atg aac cgt ggc ggt gtg tcg ctg cgt ccg ggt gac       2976
Pro Asp Phe Ile Met Asn Arg Gly Gly Val Ser Leu Arg Pro Gly Asp
            980                 985                 990 ggc gtc att cac tcc tgg ctg aac  cgt atg ctg ctg ccg  gat acc gtc     3024
Gly Val Ile His Ser Trp Leu Asn  Arg Met Leu Leu Pro  Asp Thr Val
                995                 1000                1005 ggt acc ggt ggt gac tcc cat  acc cgt ttc ccg atc  ggt atc tct          3069
Gly Thr Gly Gly Asp Ser His  Thr Arg Phe Pro Ile  Gly Ile Ser
        1010                1015                1020 ttc ccg gcg ggt tct ggt ctg  gtg gcg ttt gct gcc  gca act ggc          3114
Phe Pro Ala Gly Ser Gly Leu  Val Ala Phe Ala Ala  Ala Thr Gly
1025                1030                1035
```

-continued

```
gta atg ccg ctt gat atg ccg gaa tcc gtt ctg gtg cgc ttc aaa      3159
Val Met Pro Leu Asp Met Pro Glu Ser Val Leu Val Arg Phe Lys
    1040            1045                1050 ggc aaa atg cag ccg ggc atc acc ctg cgc gat ctg gta cac gct      3204
Gly Lys Met Gln Pro Gly Ile Thr Leu Arg Asp Leu Val His Ala
1055                1060                1065 att ccg ctg tat gcg atc aaa caa ggt ctg ctg acc gtt gag aag      3249
Ile Pro Leu Tyr Ala Ile Lys Gln Gly Leu Leu Thr Val Glu Lys
    1070            1075                1080 aaa ggc aag aaa aac atc ttc tct ggc cgc atc ctg gaa att gaa      3294
Lys Gly Lys Lys Asn Ile Phe Ser Gly Arg Ile Leu Glu Ile Glu
1085                1090                1095 ggt ctg ccg gat ctg aaa gtt gag cag gcc ttt gag cta acc gat      3339
Gly Leu Pro Asp Leu Lys Val Glu Gln Ala Phe Glu Leu Thr Asp
    1100            1105                1110 gcg tcc gcc gag cgt tct gcc gct ggt tgt acc atc aag ctg aac      3384
Ala Ser Ala Glu Arg Ser Ala Ala Gly Cys Thr Ile Lys Leu Asn
1115                1120                1125 aaa gaa ccg atc atc gaa tac ctg aac tct aac atc gtc ctg ctg      3429
Lys Glu Pro Ile Ile Glu Tyr Leu Asn Ser Asn Ile Val Leu Leu
    1130            1135                1140 aag tgg atg atc gcg gaa ggt tac ggc gat cgt cgt acc ctg gaa      3474
Lys Trp Met Ile Ala Glu Gly Tyr Gly Asp Arg Arg Thr Leu Glu
1145                1150                1155 cgt cgt att cag ggc atg gaa aaa tgg ctg gcg aat cct gag ctg      3519
Arg Arg Ile Gln Gly Met Glu Lys Trp Leu Ala Asn Pro Glu Leu
    1160            1165                1170 ctg gaa gcc gat gca gat gcg gaa tac gcg gca gtg atc gac atc      3564
Leu Glu Ala Asp Ala Asp Ala Glu Tyr Ala Ala Val Ile Asp Ile
1175                1180                1185 gat ctg gcg gat att aaa gag cca atc ctg tgt gct ccg aac gac      3609
Asp Leu Ala Asp Ile Lys Glu Pro Ile Leu Cys Ala Pro Asn Asp
    1190            1195                1200 ccg gat gac gcg cgt ccg ctg tct gcg gta cag ggt gag aag atc      3654
Pro Asp Asp Ala Arg Pro Leu Ser Ala Val Gln Gly Glu Lys Ile
1205                1210                1215 gac gaa gtg ttt atc ggt tcc tgc atg acc aac atc ggt cac ttc      3699
Asp Glu Val Phe Ile Gly Ser Cys Met Thr Asn Ile Gly His Phe
    1220            1225                1230 cgt gct gcg ggt aaa ctg ctg gat gcg cat aaa ggt cag ttg ccg      3744
Arg Ala Ala Gly Lys Leu Leu Asp Ala His Lys Gly Gln Leu Pro
1235                1240                1245 acc cgc ctg tgg gtg gca cca cca acc cgt atg gac gcc gca cag      3789
Thr Arg Leu Trp Val Ala Pro Pro Thr Arg Met Asp Ala Ala Gln
    1250            1255                1260 ttg acc gaa gaa ggc tac tac agc gtc ttc ggt aag agt ggt gcg      3834
Leu Thr Glu Glu Gly Tyr Tyr Ser Val Phe Gly Lys Ser Gly Ala
1265                1270                1275 cgt atc gag atc cct ggc tgt tcc ctg tgt atg ggt aac cag gcg      3879
Arg Ile Glu Ile Pro Gly Cys Ser Leu Cys Met Gly Asn Gln Ala
    1280            1285                1290 cgt gtg gcg gac ggt gca acg gtg gtt tcc acc tct acc cgt aac      3924
Arg Val Ala Asp Gly Ala Thr Val Val Ser Thr Ser Thr Arg Asn
1295                1300                1305 ttc ccg aac cgt ctg ggt act ggc gcg aat gtc ttc ctg gct tct      3969
Phe Pro Asn Arg Leu Gly Thr Gly Ala Asn Val Phe Leu Ala Ser
    1310            1315                1320 gcg gaa ctg gcg gct gtt gcg gcg ctg att ggc aaa ctg ccg acg      4014
Ala Glu Leu Ala Ala Val Ala Ala Leu Ile Gly Lys Leu Pro Thr
```

```
                    1325                1330                1335
ccg gaa gag tac cag acc tac gtg gcg cag gta gat aaa aca gcc      4059
Pro Glu Glu Tyr Gln Thr Tyr Val Ala Gln Val Asp Lys Thr Ala
    1340                1345                1350 gtt gat act tac cgt tat ctg aac ttc aac cag ctt tct cag tac      4104
Val Asp Thr Tyr Arg Tyr Leu Asn Phe Asn Gln Leu Ser Gln Tyr
1355                1360                1365 acc gag aaa gcc gat ggg gtg att ttc cag act gcg gtt taa          4146
Thr Glu Lys Ala Asp Gly Val Ile Phe Gln Thr Ala Val
1370                1375                1380
```

<210> SEQ ID NO 11
<211> LENGTH: 1381
<212> TYPE: PRT
<213> ORGANISM: Artificial sequence
<220> FEATURE:
<223> OTHER INFORMATION: Synthetic Construct

<400> SEQUENCE: 11

```
Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
```

```
              290                 295                 300
Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ile Ala Gly Gln
                340                 345                 350

Met Ser Val Ala Tyr Ile Leu Ala Val Gln Leu Val Asp Gln Gln Cys
                355                 360                 365

Leu Leu Ser Gln Phe Ser Glu Phe Asp Asp Asn Leu Glu Arg Pro Glu
        370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Ile Thr Glu Ser Val Glu Lys Pro Leu Gly Val
                420                 425                 430

Lys Glu Pro Met Pro Asn Glu Arg Ile Leu His Lys Tyr Arg Thr Leu
        435                 440                 445

Ala Gly Ser Val Thr Asp Glu Ser Arg Val Lys Glu Ile Glu Asp Leu
        450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Gly Ile Glu Phe Gly Pro Gly
                485                 490                 495

Pro Gly Pro Gly Pro Gly Pro Leu Glu Val Leu Phe Gln Gly Pro Gly
                500                 505                 510

Arg Ala Lys Leu Val Leu Glu Glu Tyr Arg Lys His Val Ala Glu Arg
                515                 520                 525

Ala Ala Glu Gly Ile Ala Pro Lys Pro Leu Asp Ala Asn Gln Met Ala
        530                 535                 540

Ala Leu Val Glu Leu Leu Lys Asn Pro Pro Ala Gly Glu Glu Glu Phe
545                 550                 555                 560

Leu Leu Asp Leu Leu Thr Asn Arg Val Pro Pro Gly Val Asp Glu Ala
                565                 570                 575

Ala Tyr Val Lys Ala Gly Phe Leu Ala Ala Ile Ala Lys Gly Glu Ala
                580                 585                 590

Lys Ser Pro Leu Leu Thr Pro Glu Lys Ala Ile Glu Leu Leu Gly Thr
        595                 600                 605

Met Gln Gly Gly Tyr Asn Ile His Pro Leu Ile Asp Ala Leu Asp Asp
        610                 615                 620

Ala Lys Leu Ala Pro Ile Ala Ala Lys Ala Leu Ser His Thr Leu Leu
625                 630                 635                 640

Met Phe Asp Asn Phe Tyr Asp Val Glu Glu Lys Ala Lys Ala Gly Asn
                645                 650                 655

Glu Tyr Ala Lys Gln Val Met Gln Ser Trp Ala Asp Ala Glu Trp Phe
                660                 665                 670

Leu Asn Arg Pro Ala Leu Ala Glu Lys Leu Thr Val Thr Val Phe Lys
        675                 680                 685

Val Thr Gly Glu Thr Asn Thr Asp Asp Leu Ser Pro Ala Pro Asp Ala
        690                 695                 700

Trp Ser Arg Pro Asp Ile Pro Leu His Ala Leu Ala Met Leu Lys Asn
705                 710                 715                 720
```

```
Ala Arg Glu Gly Ile Glu Pro Asp Gln Pro Gly Val Gly Pro Ile
            725                 730                 735

Lys Gln Ile Glu Ala Leu Gln Gln Lys Gly Phe Pro Leu Ala Tyr Val
            740                 745                 750

Gly Asp Val Val Gly Thr Gly Ser Ser Arg Lys Ser Ala Thr Asn Ser
            755                 760                 765

Val Leu Trp Phe Met Gly Asp Asp Ile Pro His Val Pro Asn Lys Arg
        770                 775                 780

Gly Gly Gly Leu Cys Leu Gly Gly Lys Ile Ala Pro Ile Phe Phe Asn
785                 790                 795                 800

Thr Met Glu Asp Ala Gly Ala Leu Pro Ile Glu Val Asp Val Ser Asn
            805                 810                 815

Leu Asn Met Gly Asp Val Ile Asp Val Tyr Pro Tyr Lys Gly Glu Val
            820                 825                 830

Arg Asn His Glu Thr Gly Glu Leu Leu Ala Thr Phe Glu Leu Lys Thr
            835                 840                 845

Asp Val Leu Ile Asp Glu Val Arg Ala Gly Gly Arg Ile Pro Leu Ile
            850                 855                 860

Ile Gly Arg Gly Leu Thr Thr Lys Ala Arg Glu Ala Leu Gly Leu Pro
865                 870                 875                 880

His Ser Asp Val Phe Arg Gln Ala Lys Asp Val Ala Glu Ser Asp Arg
            885                 890                 895

Gly Phe Ser Leu Ala Gln Lys Met Val Gly Arg Ala Cys Gly Val Lys
            900                 905                 910

Gly Ile Arg Pro Gly Ala Tyr Cys Glu Pro Lys Met Thr Ser Val Gly
            915                 920                 925

Ser Gln Asp Thr Thr Gly Pro Met Thr Arg Asp Glu Leu Lys Asp Leu
            930                 935                 940

Ala Cys Leu Gly Phe Ser Ala Asp Leu Val Met Gln Ser Phe Cys His
945                 950                 955                 960

Thr Ala Ala Tyr Pro Lys Pro Val Asp Val Asn Thr His His Thr Leu
                965                 970                 975

Pro Asp Phe Ile Met Asn Arg Gly Gly Val Ser Leu Arg Pro Gly Asp
            980                 985                 990

Gly Val Ile His Ser Trp Leu Asn Arg Met Leu Leu Pro Asp Thr Val
            995                 1000                1005

Gly Thr Gly Gly Asp Ser His Thr Arg Phe Pro Ile Gly Ile Ser
        1010                1015                1020

Phe Pro Ala Gly Ser Gly Leu Val Ala Phe Ala Ala Ala Thr Gly
        1025                1030                1035

Val Met Pro Leu Asp Met Pro Glu Ser Val Leu Val Arg Phe Lys
        1040                1045                1050

Gly Lys Met Gln Pro Gly Ile Thr Leu Arg Asp Leu Val His Ala
        1055                1060                1065

Ile Pro Leu Tyr Ala Ile Lys Gln Gly Leu Leu Thr Val Glu Lys
        1070                1075                1080

Lys Gly Lys Lys Asn Ile Phe Ser Gly Arg Ile Leu Glu Ile Glu
        1085                1090                1095

Gly Leu Pro Asp Leu Lys Val Glu Gln Ala Phe Glu Leu Thr Asp
        1100                1105                1110

Ala Ser Ala Glu Arg Ser Ala Ala Gly Cys Thr Ile Lys Leu Asn
        1115                1120                1125
```

```
Lys Glu Pro Ile Ile Glu Tyr Leu Asn Ser Asn Ile Val Leu Leu
    1130                1135                1140

Lys Trp Met Ile Ala Glu Gly Tyr Gly Asp Arg Arg Thr Leu Glu
    1145                1150                1155

Arg Arg Ile Gln Gly Met Glu Lys Trp Leu Ala Asn Pro Glu Leu
    1160                1165                1170

Leu Glu Ala Asp Ala Asp Ala Glu Tyr Ala Ala Val Ile Asp Ile
    1175                1180                1185

Asp Leu Ala Asp Ile Lys Glu Pro Ile Leu Cys Ala Pro Asn Asp
    1190                1195                1200

Pro Asp Asp Ala Arg Pro Leu Ser Ala Val Gln Gly Glu Lys Ile
    1205                1210                1215

Asp Glu Val Phe Ile Gly Ser Cys Met Thr Asn Ile Gly His Phe
    1220                1225                1230

Arg Ala Ala Gly Lys Leu Leu Asp Ala His Lys Gly Gln Leu Pro
    1235                1240                1245

Thr Arg Leu Trp Val Ala Pro Pro Thr Arg Met Asp Ala Ala Gln
    1250                1255                1260

Leu Thr Glu Glu Gly Tyr Tyr Ser Val Phe Gly Lys Ser Gly Ala
    1265                1270                1275

Arg Ile Glu Ile Pro Gly Cys Ser Leu Cys Met Gly Asn Gln Ala
    1280                1285                1290

Arg Val Ala Asp Gly Ala Thr Val Val Ser Thr Ser Thr Arg Asn
    1295                1300                1305

Phe Pro Asn Arg Leu Gly Thr Gly Ala Asn Val Phe Leu Ala Ser
    1310                1315                1320

Ala Glu Leu Ala Ala Val Ala Ala Leu Ile Gly Lys Leu Pro Thr
    1325                1330                1335

Pro Glu Glu Tyr Gln Thr Tyr Val Ala Gln Val Asp Lys Thr Ala
    1340                1345                1350

Val Asp Thr Tyr Arg Tyr Leu Asn Phe Asn Gln Leu Ser Gln Tyr
    1355                1360                1365

Thr Glu Lys Ala Asp Gly Val Ile Phe Gln Thr Ala Val
    1370                1375                1380

<210> SEQ ID NO 12
<211> LENGTH: 4146
<212> TYPE: DNA
<213> ORGANISM: Artificial sequence
<220> FEATURE:
<223> OTHER INFORMATION: fusion polypeptide
<220> FEATURE:
<221> NAME/KEY: CDS
<222> LOCATION: (1)..(4146)

<400> SEQUENCE: 12 atg acc aag cag tct gct gat tcc aac gcg aag tct ggt gtg acc tct      48
Met Thr Lys Gln Ser Ala Asp Ser Asn Ala Lys Ser Gly Val Thr Ser
1               5                   10                  15 gag atc tgt cac tgg gcg tct aat ctc gcc act gat gat atc ccg agc      96
Glu Ile Cys His Trp Ala Ser Asn Leu Ala Thr Asp Asp Ile Pro Ser
            20                  25                  30 gac gtt ctg gag cgt gca aaa tac ctg atc ctg gat ggt atc gcg tgc     144
Asp Val Leu Glu Arg Ala Lys Tyr Leu Ile Leu Asp Gly Ile Ala Cys
        35                  40                  45 gcg tgg gta ggt gct cgt gtc cca tgg tct gaa aaa tac gtt caa gcg     192
Ala Trp Val Gly Ala Arg Val Pro Trp Ser Glu Lys Tyr Val Gln Ala
    50                  55                  60
```

```
acc atg tct ttc gaa cct ccg ggt gcg tgt cgt gtc atc ggt tac ggc      240
Thr Met Ser Phe Glu Pro Pro Gly Ala Cys Arg Val Ile Gly Tyr Gly
 65              70                  75                  80 cag aaa ctg ggt ccg gta gcg gcc atg acg aac tct gca ttt att          288
Gln Lys Leu Gly Pro Val Ala Ala Ala Met Thr Asn Ser Ala Phe Ile
                 85                  90                  95 cag gcg acc gaa ctc gat gac tat cac tct gaa gcg ccg ctg cat tcc      336
Gln Ala Thr Glu Leu Asp Asp Tyr His Ser Glu Ala Pro Leu His Ser
            100                 105                 110 gcg tct atc gtt ctc ccg gca gtt ttc gcg gcg agc gaa gta ctg gcc      384
Ala Ser Ile Val Leu Pro Ala Val Phe Ala Ala Ser Glu Val Leu Ala
        115                 120                 125 gaa cag ggt aaa acc atc tct ggt att gac gtg att ctg gct gcg atc      432
Glu Gln Gly Lys Thr Ile Ser Gly Ile Asp Val Ile Leu Ala Ala Ile
130                 135                 140 gtt ggt ttc gag agc ggt cct cgc atc ggc aaa gcg atc tac ggt tct      480
Val Gly Phe Glu Ser Gly Pro Arg Ile Gly Lys Ala Ile Tyr Gly Ser
145                 150                 155                 160 gac ctc ctg aac aac ggc tgg cac tgc ggt gcg gta tat ggc gca ccg      528
Asp Leu Leu Asn Asn Gly Trp His Cys Gly Ala Val Tyr Gly Ala Pro
                165                 170                 175 gct ggt gcg ctc gca act ggt aag ctc ctg ggc ctc acg ccg gac agc      576
Ala Gly Ala Leu Ala Thr Gly Lys Leu Leu Gly Leu Thr Pro Asp Ser
            180                 185                 190 atg gaa gat gca ctg ggt att gcc tgc acg caa gca tgc ggc ctc atg      624
Met Glu Asp Ala Leu Gly Ile Ala Cys Thr Gln Ala Cys Gly Leu Met
        195                 200                 205 tcc gcg cag tat ggt ggc atg gtt aaa cgt gtt cag cac ggt ttc gca      672
Ser Ala Gln Tyr Gly Gly Met Val Lys Arg Val Gln His Gly Phe Ala
210                 215                 220 gcg cgt aat ggt ctc ctc ggt ggc ctc ctg gct cac ggc ggc tac gag      720
Ala Arg Asn Gly Leu Leu Gly Gly Leu Leu Ala His Gly Gly Tyr Glu
225                 230                 235                 240 gcg atg aaa ggt gtt ctc gag cgt tct tac ggt ggc ttc ctg aag atg      768
Ala Met Lys Gly Val Leu Glu Arg Ser Tyr Gly Gly Phe Leu Lys Met
                245                 250                 255 ttc acc aag ggc aac ggt cgt gaa ccg ccg tac aaa gaa gaa gag gtt      816
Phe Thr Lys Gly Asn Gly Arg Glu Pro Pro Tyr Lys Glu Glu Glu Val
            260                 265                 270 gtg gct ggt ctg ggt agc ttc tgg cac acc ttc acc att cgt atc aaa      864
Val Ala Gly Leu Gly Ser Phe Trp His Thr Phe Thr Ile Arg Ile Lys
        275                 280                 285 ctg tac gcg tgc tgc ggt ctc gta cac ggt cct gtt gaa gcc att gaa      912
Leu Tyr Ala Cys Cys Gly Leu Val His Gly Pro Val Glu Ala Ile Glu
290                 295                 300 aac ctc cag ggt cgt tac ccg gaa ctg ctc aat cgt gct aac ctg tct      960
Asn Leu Gln Gly Arg Tyr Pro Glu Leu Leu Asn Arg Ala Asn Leu Ser
305                 310                 315                 320 aac atc cgc cac gtt cac gta caa ctc tct acc gcg agc aac tcc cac     1008
Asn Ile Arg His Val His Val Gln Leu Ser Thr Ala Ser Asn Ser His
                325                 330                 335 tgt ggt tgg atc cca gaa gag cgc cca atc tct tct atc gcg ggt caa     1056
Cys Gly Trp Ile Pro Glu Glu Arg Pro Ile Ser Ser Ile Ala Gly Gln
            340                 345                 350 atg tct gtc gca tat atc ctc gcc gtt cag ctc gtt gac caa cag tgt     1104
Met Ser Val Ala Tyr Ile Leu Ala Val Gln Leu Val Asp Gln Gln Cys
        355                 360                 365 ctg ctc agc cag ttc tcc gag ttt gac gat aat ctg gaa cgc ccg gaa     1152
Leu Leu Ser Gln Phe Ser Glu Phe Asp Asp Asn Leu Glu Arg Pro Glu
```

-continued

```
                    370                 375                 380
gtg tgg gac ctg gca cgt aag gtt acc agc tct caa tct gag gag ttc    1200
Val Trp Asp Leu Ala Arg Lys Val Thr Ser Ser Gln Ser Glu Glu Phe
385                 390                 395                 400 gac cag gac ggt aac tgt ctc tct gcc ggt cgc gtc cgt att gag ttc    1248
Asp Gln Asp Gly Asn Cys Leu Ser Ala Gly Arg Val Arg Ile Glu Phe
                405                 410                 415 aac gac ggc tcc tcc atc acc gaa tcc gtt gag aag ccg ctc ggt gta    1296
Asn Asp Gly Ser Ser Ile Thr Glu Ser Val Glu Lys Pro Leu Gly Val
            420                 425                 430 aag gaa cca atg cca aat gaa cgc atc ctg cac aaa tac cgt acc ctg    1344
Lys Glu Pro Met Pro Asn Glu Arg Ile Leu His Lys Tyr Arg Thr Leu
        435                 440                 445 gcg ggt tct gta acg gac gaa agc cgt gtt aag gag atc gag gat ctc    1392
Ala Gly Ser Val Thr Asp Glu Ser Arg Val Lys Glu Ile Glu Asp Leu
    450                 455                 460 gtg ctc ggc ctg gac cgt ctg acc gat att agc ccg ctc ctc gag ctg    1440
Val Leu Gly Leu Asp Arg Leu Thr Asp Ile Ser Pro Leu Leu Glu Leu
465                 470                 475                 480 ctg aat tgt ccg gtt aaa tcc cca ctg ggt att gaa ttt ggt ccg ggt    1488
Leu Asn Cys Pro Val Lys Ser Pro Leu Gly Ile Glu Phe Gly Pro Gly
                485                 490                 495 cca ggt cct ggt cct ggc cct cta gaa gtg ttg ttc caa ggt cct ggt    1536
Pro Gly Pro Gly Pro Gly Pro Leu Glu Val Leu Phe Gln Gly Pro Gly
            500                 505                 510 cgt gcg aaa ctc gtg cta gaa gaa tac cgt aag cac gta gct gag cgt    1584
Arg Ala Lys Leu Val Leu Glu Glu Tyr Arg Lys His Val Ala Glu Arg
        515                 520                 525 gcc gct gag ggg att gcg ccc aaa ccc ctg gat gca aac caa atg gcc    1632
Ala Ala Glu Gly Ile Ala Pro Lys Pro Leu Asp Ala Asn Gln Met Ala
    530                 535                 540 gca ctt gta gag ctg ctg aaa aac ccg ccg gcg ggc gaa gaa gaa ttc    1680
Ala Leu Val Glu Leu Leu Lys Asn Pro Pro Ala Gly Glu Glu Glu Phe
545                 550                 555                 560 ctg tta gat ctg tta acc aac cgt gtt ccc cca ggc gtc gat gaa gcc    1728
Leu Leu Asp Leu Leu Thr Asn Arg Val Pro Pro Gly Val Asp Glu Ala
                565                 570                 575 gcc tat gtc aaa gca ggc ttc ctg gct gct atc gcg aaa ggc gaa gcc    1776
Ala Tyr Val Lys Ala Gly Phe Leu Ala Ala Ile Ala Lys Gly Glu Ala
            580                 585                 590 aaa tcc cct ctg ctg act ccg gaa aaa gcc atc gaa ctg ctg ggc acc    1824
Lys Ser Pro Leu Leu Thr Pro Glu Lys Ala Ile Glu Leu Leu Gly Thr
        595                 600                 605 atg cag ggt ggt tac aac att cat ccg ctg atc gac gcg ctg gat gat    1872
Met Gln Gly Gly Tyr Asn Ile His Pro Leu Ile Asp Ala Leu Asp Asp
    610                 615                 620 gcc aaa ctg gca cct att gct gcc aaa gca ctt tct cac acg ctg ctg    1920
Ala Lys Leu Ala Pro Ile Ala Ala Lys Ala Leu Ser His Thr Leu Leu
625                 630                 635                 640 atg ttc gat aac ttc tat gac gta gaa gag aaa gcg aaa gca ggc aac    1968
Met Phe Asp Asn Phe Tyr Asp Val Glu Glu Lys Ala Lys Ala Gly Asn
                645                 650                 655 gaa tat gcg aag cag gtt atg cag tcc tgg gcg gat gcc gaa tgg ttc    2016
Glu Tyr Ala Lys Gln Val Met Gln Ser Trp Ala Asp Ala Glu Trp Phe
            660                 665                 670 ctg aat cgc ccg gcg ctg gct gaa aaa ctg acc gtt act gtc ttc aaa    2064
Leu Asn Arg Pro Ala Leu Ala Glu Lys Leu Thr Val Thr Val Phe Lys
        675                 680                 685 gtc act ggc gaa act aac acc gat gac ctt tct ccg gca ccg gat gcg    2112
```

```
Val Thr Gly Glu Thr Asn Thr Asp Asp Leu Ser Pro Ala Pro Asp Ala
    690             695                 700 tgg tca cgc ccg gat atc cca ctg cac gcg ctg gcg atg ctg aaa aac    2160
Trp Ser Arg Pro Asp Ile Pro Leu His Ala Leu Ala Met Leu Lys Asn
705             710                 715                 720 gcc cgt gaa ggt att gag cca gac cag cct ggt gtt gtt ggt ccg atc    2208
Ala Arg Glu Gly Ile Glu Pro Asp Gln Pro Gly Val Val Gly Pro Ile
                725                 730                 735 aag caa atc gaa gct ctg caa cag aaa ggt ttc ccg ctg gcg tac gtc    2256
Lys Gln Ile Glu Ala Leu Gln Gln Lys Gly Phe Pro Leu Ala Tyr Val
            740                 745                 750 ggt gac gtt gtg ggt acg ggt tct tcg cgt aaa tcc gcc act aac tcc    2304
Gly Asp Val Val Gly Thr Gly Ser Ser Arg Lys Ser Ala Thr Asn Ser
        755                 760                 765 gtt ctg tgg ttt atg ggc gat gat att cca cat gtg ccg aac aaa cgc    2352
Val Leu Trp Phe Met Gly Asp Asp Ile Pro His Val Pro Asn Lys Arg
770             775                 780 ggc ggt ggt ttg tgc ctc ggc ggt aaa att gca ccc atc ttc ttt aac    2400
Gly Gly Gly Leu Cys Leu Gly Gly Lys Ile Ala Pro Ile Phe Phe Asn
785             790                 795                 800 acg atg gaa gac gcg ggt gca ctg cca atc gaa gtc gac gtc tct aac    2448
Thr Met Glu Asp Ala Gly Ala Leu Pro Ile Glu Val Asp Val Ser Asn
                805                 810                 815 ctg aac atg ggc gac gtg att gac gtt tac ccg tac aaa ggt gaa gtg    2496
Leu Asn Met Gly Asp Val Ile Asp Val Tyr Pro Tyr Lys Gly Glu Val
            820                 825                 830 cgt aac cac gaa acc ggc gaa ctg ctg gcg acc ttc gaa ctg aaa acc    2544
Arg Asn His Glu Thr Gly Glu Leu Leu Ala Thr Phe Glu Leu Lys Thr
        835                 840                 845 gac gtg ctg att gat gaa gtg cgt gct ggt ggc cgt att ccg ctg att    2592
Asp Val Leu Ile Asp Glu Val Arg Ala Gly Gly Arg Ile Pro Leu Ile
850                 855                 860 atc ggg cgt ggc ctg acc acc aaa gcg cgt gaa gca ctt ggt ctg ccg    2640
Ile Gly Arg Gly Leu Thr Thr Lys Ala Arg Glu Ala Leu Gly Leu Pro
865             870                 875                 880 cac agt gat gtg ttc cgt cag gcg aaa gat gtc gct gag agc gat cgc    2688
His Ser Asp Val Phe Arg Gln Ala Lys Asp Val Ala Glu Ser Asp Arg
                885                 890                 895 ggc ttc tcg ctg gcg caa aaa atg gta ggc cgt gcc tgt ggc gtg aaa    2736
Gly Phe Ser Leu Ala Gln Lys Met Val Gly Arg Ala Cys Gly Val Lys
            900                 905                 910 ggc att cgt ccg ggc gcg tac tgt gaa ccg aaa atg act tct gta ggt    2784
Gly Ile Arg Pro Gly Ala Tyr Cys Glu Pro Lys Met Thr Ser Val Gly
        915                 920                 925 tcc cag gac acc acc ggc ccg atg acc cgt gat cag ctg aaa gac ctg    2832
Ser Gln Asp Thr Thr Gly Pro Met Thr Arg Asp Gln Leu Lys Asp Leu
930                 935                 940 gcg tgc ctg ggc ttc tcg gct gac ctg gtg atg cag tct ttc tgc cac    2880
Ala Cys Leu Gly Phe Ser Ala Asp Leu Val Met Gln Ser Phe Cys His
945             950                 955                 960 acc gcg gcg tat ccg aag cca gtt gac gtg aac acg cac cac acg ctg    2928
Thr Ala Ala Tyr Pro Lys Pro Val Asp Val Asn Thr His His Thr Leu
                965                 970                 975 ccg gac ttc att atg aac cgt ggc ggt gtg tcg ctg cgt ccg ggt gac    2976
Pro Asp Phe Ile Met Asn Arg Gly Gly Val Ser Leu Arg Pro Gly Asp
            980                 985                 990 ggc gtc att cac tcc tgg ctg aac cgt atg ctg ctg ccg gat acc gtc    3024
Gly Val Ile His Ser Trp Leu Asn Arg Met Leu Leu Pro Asp Thr Val
        995                 1000                1005
```

-continued

| | | |
|---|---|---|
| ggt acc ggt ggt gac tcc cat acc cgt ttc ccg atc ggt atc tct<br>Gly Thr Gly Gly Asp Ser His Thr Arg Phe Pro Ile Gly Ile Ser<br>1010               1015                   1020 | 3069 |
| ttc ccg gcg ggt tct ggt ctg gtg gcg ttt gct gcc gca act ggc<br>Phe Pro Ala Gly Ser Gly Leu Val Ala Phe Ala Ala Ala Thr Gly<br>1025               1030                   1035 | 3114 |
| gta atg ccg ctt gat atg ccg gaa tcc gtt ctg gtg cgc ttc aaa<br>Val Met Pro Leu Asp Met Pro Glu Ser Val Leu Val Arg Phe Lys<br>1040               1045                   1050 | 3159 |
| ggc aaa atg cag ccg ggc atc acc ctg cgc gat ctg gta cac gct<br>Gly Lys Met Gln Pro Gly Ile Thr Leu Arg Asp Leu Val His Ala<br>1055               1060                   1065 | 3204 |
| att ccg ctg tat gcg atc aaa caa ggt ctg ctg acc gtt gag aag<br>Ile Pro Leu Tyr Ala Ile Lys Gln Gly Leu Leu Thr Val Glu Lys<br>1070               1075                   1080 | 3249 |
| aaa ggc aag aaa aac atc ttc tct ggc cgc atc ctg gaa att gaa<br>Lys Gly Lys Lys Asn Ile Phe Ser Gly Arg Ile Leu Glu Ile Glu<br>1085               1090                   1095 | 3294 |
| ggt ctg ccg gat ctg aaa gtt gag cag gcc ttt gag cta acc gat<br>Gly Leu Pro Asp Leu Lys Val Glu Gln Ala Phe Glu Leu Thr Asp<br>1100               1105                   1110 | 3339 |
| gcg tcc gcc gag cgt tct gcc gct ggt tgt acc atc aag ctg aac<br>Ala Ser Ala Glu Arg Ser Ala Ala Gly Cys Thr Ile Lys Leu Asn<br>1115               1120                   1125 | 3384 |
| aaa gaa ccg atc atc gaa tac ctg aac tct aac atc gtc ctg ctg<br>Lys Glu Pro Ile Ile Glu Tyr Leu Asn Ser Asn Ile Val Leu Leu<br>1130               1135                   1140 | 3429 |
| aag tgg atg atc gcg gaa ggt tac ggc gat cgt cgt acc ctg gaa<br>Lys Trp Met Ile Ala Glu Gly Tyr Gly Asp Arg Arg Thr Leu Glu<br>1145               1150                   1155 | 3474 |
| cgt cgt att cag ggc atg gaa aaa tgg ctg gcg aat cct gag ctg<br>Arg Arg Ile Gln Gly Met Glu Lys Trp Leu Ala Asn Pro Glu Leu<br>1160               1165                   1170 | 3519 |
| ctg gaa gcc gat gca gat gcg gaa tac gcg gca gtg atc gac atc<br>Leu Glu Ala Asp Ala Asp Ala Glu Tyr Ala Ala Val Ile Asp Ile<br>1175               1180                   1185 | 3564 |
| gat ctg gcg gat att aaa gag cca atc ctg tgt gct ccg aac gac<br>Asp Leu Ala Asp Ile Lys Glu Pro Ile Leu Cys Ala Pro Asn Asp<br>1190               1195                   1200 | 3609 |
| ccg gat gac gcg cgt ccg ctg tct gcg gta cag ggt gag aag atc<br>Pro Asp Asp Ala Arg Pro Leu Ser Ala Val Gln Gly Glu Lys Ile<br>1205               1210                   1215 | 3654 |
| gac gaa gtg ttt atc ggt tcc tgc atg acc aac atc ggt cac ttc<br>Asp Glu Val Phe Ile Gly Ser Cys Met Thr Asn Ile Gly His Phe<br>1220               1225                   1230 | 3699 |
| cgt gct gcg ggt aaa ctg ctg gat gcg cat aaa ggt cag ttg ccg<br>Arg Ala Ala Gly Lys Leu Leu Asp Ala His Lys Gly Gln Leu Pro<br>1235               1240                   1245 | 3744 |
| acc cgc ctg tgg gtg gca ccg cca acc cgt atg gac gcc gca cag<br>Thr Arg Leu Trp Val Ala Pro Pro Thr Arg Met Asp Ala Ala Gln<br>1250               1255                   1260 | 3789 |
| ttg acc gaa gaa ggc tac tac agc gtc ttc ggt aag agt ggt gcg<br>Leu Thr Glu Glu Gly Tyr Tyr Ser Val Phe Gly Lys Ser Gly Ala<br>1265               1270                   1275 | 3834 |
| cgt atc gag atc cct ggc tgt tcc ctg tgt atg ggt aac cag gcg<br>Arg Ile Glu Ile Pro Gly Cys Ser Leu Cys Met Gly Asn Gln Ala<br>1280               1285                   1290 | 3879 |
| cgt gtg gcg gac ggt gca acg gtg gtt tcc acc tct acc cgt aac<br>Arg Val Ala Asp Gly Ala Thr Val Val Ser Thr Ser Thr Arg Asn<br>1295               1300                   1305 | 3924 |

```
ttc ccg aac cgt ctg ggt act ggc gcg aat gtc ttc ctg gct tct    3969
Phe Pro Asn Arg Leu Gly Thr Gly Ala Asn Val Phe Leu Ala Ser
1310                1315                1320 gcg gaa ctg gcg gct gtt gcg gcg ctg att ggc aaa ctg ccg acg    4014
Ala Glu Leu Ala Ala Val Ala Ala Leu Ile Gly Lys Leu Pro Thr
    1325                1330                1335 ccg gaa gag tac cag acc tac gtg gcg cag gta gat aaa aca gcc    4059
Pro Glu Glu Tyr Gln Thr Tyr Val Ala Gln Val Asp Lys Thr Ala
        1340                1345                1350 gtt gat act tac cgt tat ctg aac ttc aac cag ctt tct cag tac    4104
Val Asp Thr Tyr Arg Tyr Leu Asn Phe Asn Gln Leu Ser Gln Tyr
            1355                1360                1365 acc gag aaa gcc gat ggg gtg att ttc cag act gcg gtt taa        4146
Thr Glu Lys Ala Asp Gly Val Ile Phe Gln Thr Ala Val
                1370                1375                1380
```

<210> SEQ ID NO 13
<211> LENGTH: 1381
<212> TYPE: PRT
<213> ORGANISM: Artificial sequence
<220> FEATURE:
<223> OTHER INFORMATION: Synthetic Construct

<400> SEQUENCE: 13

```
Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Met Thr Asn Ser Ala Phe Ile
            85                  90                  95

Gln Ala Thr Glu Leu Asp Asp Tyr His Ser Gly Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255
```

-continued

```
Phe Thr Lys Gly Asn Gly Arg Glu Pro Pro Tyr Lys Glu Glu Val
            260                 265                 270
Val Ala Gly Leu Gly Ser Phe Trp His Thr Phe Thr Ile Arg Ile Lys
275                 280                 285
Leu Tyr Ala Cys Cys Gly Leu Val His Gly Pro Val Glu Ala Ile Glu
290                 295                 300
Asn Leu Gln Gly Arg Tyr Pro Glu Leu Leu Asn Arg Ala Asn Leu Ser
305                 310                 315                 320
Asn Ile Arg His Val His Val Gln Leu Ser Thr Ala Ser Asn Ser His
                325                 330                 335
Cys Gly Trp Ile Pro Glu Glu Arg Pro Ile Ser Ser Ile Ala Gly Gln
            340                 345                 350
Met Ser Val Ala Tyr Ile Leu Ala Val Gln Leu Val Asp Gln Gln Cys
        355                 360                 365
Leu Leu Ser Gln Phe Ser Glu Phe Asp Asp Asn Leu Glu Arg Pro Glu
    370                 375                 380
Val Trp Asp Leu Ala Arg Lys Val Thr Ser Ser Gln Ser Glu Glu Phe
385                 390                 395                 400
Asp Gln Asp Gly Asn Cys Leu Ser Ala Gly Arg Val Arg Ile Glu Phe
                405                 410                 415
Asn Asp Gly Ser Ser Ile Thr Glu Ser Val Glu Lys Pro Leu Gly Val
            420                 425                 430
Lys Glu Pro Met Pro Asn Glu Arg Ile Leu His Lys Tyr Arg Thr Leu
        435                 440                 445
Ala Gly Ser Val Thr Asp Glu Ser Arg Val Lys Glu Ile Glu Asp Leu
    450                 455                 460
Val Leu Gly Leu Asp Arg Leu Thr Asp Ile Ser Pro Leu Leu Glu Leu
465                 470                 475                 480
Leu Asn Cys Pro Val Lys Ser Pro Leu Gly Ile Glu Phe Gly Pro Gly
                485                 490                 495
Pro Gly Pro Gly Pro Gly Pro Leu Glu Val Leu Phe Gln Gly Pro Gly
            500                 505                 510
Arg Ala Lys Leu Val Leu Glu Glu Tyr Arg Lys His Val Ala Glu Arg
        515                 520                 525
Ala Ala Glu Gly Ile Ala Pro Lys Pro Leu Asp Ala Asn Gln Met Ala
    530                 535                 540
Ala Leu Val Glu Leu Leu Lys Asn Pro Pro Ala Gly Glu Glu Glu Phe
545                 550                 555                 560
Leu Leu Asp Leu Leu Thr Asn Arg Val Pro Pro Gly Val Asp Glu Ala
                565                 570                 575
Ala Tyr Val Lys Ala Gly Phe Leu Ala Ala Ile Ala Lys Gly Glu Ala
            580                 585                 590
Lys Ser Pro Leu Leu Thr Pro Glu Lys Ala Ile Glu Leu Leu Gly Thr
        595                 600                 605
Met Gln Gly Gly Tyr Asn Ile His Pro Leu Ile Asp Ala Leu Asp Asp
    610                 615                 620
Ala Lys Leu Ala Pro Ile Ala Ala Lys Ala Leu Ser His Thr Leu Leu
625                 630                 635                 640
Met Phe Asp Asn Phe Tyr Asp Val Glu Glu Lys Ala Lys Ala Gly Asn
                645                 650                 655
Glu Tyr Ala Lys Gln Val Met Gln Ser Trp Ala Asp Ala Glu Trp Phe
            660                 665                 670
Leu Asn Arg Pro Ala Leu Ala Glu Lys Leu Thr Val Thr Val Phe Lys
```

-continued

```
            675                 680                 685
Val Thr Gly Glu Thr Asn Thr Asp Asp Leu Ser Pro Ala Pro Asp Ala
            690                 695                 700

Trp Ser Arg Pro Asp Ile Pro Leu His Ala Leu Ala Met Leu Lys Asn
705                 710                 715                 720

Ala Arg Glu Gly Ile Glu Pro Asp Gln Pro Gly Val Val Gly Pro Ile
            725                 730                 735

Lys Gln Ile Glu Ala Leu Gln Gln Lys Gly Phe Pro Leu Ala Tyr Val
            740                 745                 750

Gly Asp Val Val Gly Thr Gly Ser Ser Arg Lys Ser Ala Thr Asn Ser
            755                 760                 765

Val Leu Trp Phe Met Gly Asp Asp Ile Pro His Val Pro Asn Lys Arg
770                 775                 780

Gly Gly Gly Leu Cys Leu Gly Gly Lys Ile Ala Pro Ile Phe Phe Asn
785                 790                 795                 800

Thr Met Glu Asp Ala Gly Ala Leu Pro Ile Glu Val Asp Val Ser Asn
            805                 810                 815

Leu Asn Met Gly Asp Val Ile Asp Val Tyr Pro Tyr Lys Gly Glu Val
            820                 825                 830

Arg Asn His Glu Thr Gly Glu Leu Leu Ala Thr Phe Glu Leu Lys Thr
            835                 840                 845

Asp Val Leu Ile Asp Glu Val Arg Ala Gly Gly Arg Ile Pro Leu Ile
850                 855                 860

Ile Gly Arg Gly Leu Thr Thr Lys Ala Arg Glu Ala Leu Gly Leu Pro
865                 870                 875                 880

His Ser Asp Val Phe Arg Gln Ala Lys Asp Val Ala Glu Ser Asp Arg
            885                 890                 895

Gly Phe Ser Leu Ala Gln Lys Met Val Gly Arg Ala Cys Gly Val Lys
            900                 905                 910

Gly Ile Arg Pro Gly Ala Tyr Cys Glu Pro Lys Met Thr Ser Val Gly
            915                 920                 925

Ser Gln Asp Thr Thr Gly Pro Met Thr Arg Asp Gln Leu Lys Asp Leu
            930                 935                 940

Ala Cys Leu Gly Phe Ser Ala Asp Leu Val Met Gln Ser Phe Cys His
945                 950                 955                 960

Thr Ala Ala Tyr Pro Lys Pro Val Asp Val Asn Thr His His Thr Leu
            965                 970                 975

Pro Asp Phe Ile Met Asn Arg Gly Gly Val Ser Leu Arg Pro Gly Asp
            980                 985                 990

Gly Val Ile His Ser Trp Leu Asn Arg Met Leu Leu Pro Asp Thr Val
            995                 1000                1005

Gly Thr Gly Gly Asp Ser His Thr Arg Phe Pro Ile Gly Ile Ser
            1010                1015                1020

Phe Pro Ala Gly Ser Gly Leu Val Ala Phe Ala Ala Ala Thr Gly
            1025                1030                1035

Val Met Pro Leu Asp Met Pro Glu Ser Val Leu Val Arg Phe Lys
            1040                1045                1050

Gly Lys Met Gln Pro Gly Ile Thr Leu Arg Asp Leu Val His Ala
            1055                1060                1065

Ile Pro Leu Tyr Ala Ile Lys Gln Gly Leu Leu Thr Val Glu Lys
            1070                1075                1080

Lys Gly Lys Lys Asn Ile Phe Ser Gly Arg Ile Leu Glu Ile Glu
            1085                1090                1095
```

```
Gly Leu Pro Asp Leu Lys Val Glu Gln Ala Phe Glu Leu Thr Asp
    1100                1105                1110

Ala Ser Ala Glu Arg Ser Ala Ala Gly Cys Thr Ile Lys Leu Asn
    1115                1120                1125

Lys Glu Pro Ile Ile Glu Tyr Leu Asn Ser Asn Ile Val Leu Leu
    1130                1135                1140

Lys Trp Met Ile Ala Glu Gly Tyr Gly Asp Arg Thr Leu Glu
    1145                1150                1155

Arg Arg Ile Gln Gly Met Glu Lys Trp Leu Ala Asn Pro Glu Leu
    1160                1165                1170

Leu Glu Ala Asp Ala Asp Ala Glu Tyr Ala Ala Val Ile Asp Ile
    1175                1180                1185

Asp Leu Ala Asp Ile Lys Glu Pro Ile Leu Cys Ala Pro Asn Asp
    1190                1195                1200

Pro Asp Asp Ala Arg Pro Leu Ser Ala Val Gln Gly Glu Lys Ile
    1205                1210                1215

Asp Glu Val Phe Ile Gly Ser Cys Met Thr Asn Ile Gly His Phe
    1220                1225                1230

Arg Ala Ala Gly Lys Leu Leu Asp Ala His Lys Gly Gln Leu Pro
    1235                1240                1245

Thr Arg Leu Trp Val Ala Pro Pro Thr Arg Met Asp Ala Ala Gln
    1250                1255                1260

Leu Thr Glu Glu Gly Tyr Tyr Ser Val Phe Gly Lys Ser Gly Ala
    1265                1270                1275

Arg Ile Glu Ile Pro Gly Cys Ser Leu Cys Met Gly Asn Gln Ala
    1280                1285                1290

Arg Val Ala Asp Gly Ala Thr Val Val Ser Thr Ser Thr Arg Asn
    1295                1300                1305

Phe Pro Asn Arg Leu Gly Thr Gly Ala Asn Val Phe Leu Ala Ser
    1310                1315                1320

Ala Glu Leu Ala Ala Val Ala Ala Leu Ile Gly Lys Leu Pro Thr
    1325                1330                1335

Pro Glu Glu Tyr Gln Thr Tyr Val Ala Gln Val Asp Lys Thr Ala
    1340                1345                1350

Val Asp Thr Tyr Arg Tyr Leu Asn Phe Asn Gln Leu Ser Gln Tyr
    1355                1360                1365

Thr Glu Lys Ala Asp Gly Val Ile Phe Gln Thr Ala Val
    1370                1375                1380

<210> SEQ ID NO 14
<211> LENGTH: 3888
<212> TYPE: DNA
<213> ORGANISM: Artificial sequence
<220> FEATURE:
<223> OTHER INFORMATION: fusion polypeptide
<220> FEATURE:
<221> NAME/KEY: CDS
<222> LOCATION: (1)..(3888)

<400> SEQUENCE: 14 atg acc aag cag tct gct gat tcc aac gcg aag tct ggt gtg acc tct    48
Met Thr Lys Gln Ser Ala Asp Ser Asn Ala Lys Ser Gly Val Thr Ser
1               5                   10                  15 gag atc tgt cac tgg gcg tct aat ctc gcc act gat gat atc ccg agc    96
Glu Ile Cys His Trp Ala Ser Asn Leu Ala Thr Asp Asp Ile Pro Ser
            20                  25                  30
```

```
gac gtt ctg gag cgt gca aaa tac ctg atc ctg gat ggt atc gcg tgc      144
Asp Val Leu Glu Arg Ala Lys Tyr Leu Ile Leu Asp Gly Ile Ala Cys
        35                  40                  45 gcg tgg gta ggt gct cgt gtc cca tgg tct gaa aaa tac gtt caa gcg      192
Ala Trp Val Gly Ala Arg Val Pro Trp Ser Glu Lys Tyr Val Gln Ala
 50                  55                  60 acc atg tct ttc gaa cct ccg ggt gcg tgt cgt gtc atc ggt tac ggc      240
Thr Met Ser Phe Glu Pro Pro Gly Ala Cys Arg Val Ile Gly Tyr Gly
 65                  70                  75                  80 cag aaa ctg ggt cca gta gcg gct gcc atg acg aac tct gca ttt att      288
Gln Lys Leu Gly Pro Val Ala Ala Ala Met Thr Asn Ser Ala Phe Ile
                 85                  90                  95 cag gcg acc gaa ctc gat gac tat cac tct gaa gcg ccg ctg cat tcc      336
Gln Ala Thr Glu Leu Asp Asp Tyr His Ser Glu Ala Pro Leu His Ser
            100                 105                 110 gcg tct atc gtt ctc ccg gca gtt ttc gcg gcg agc gaa gta ctg gcc      384
Ala Ser Ile Val Leu Pro Ala Val Phe Ala Ala Ser Glu Val Leu Ala
        115                 120                 125 gaa cag ggt aaa acc atc tct ggt att gac gtg att ctg gct gcg atc      432
Glu Gln Gly Lys Thr Ile Ser Gly Ile Asp Val Ile Leu Ala Ala Ile
130                 135                 140 gtt ggt ttc gag agc ggt cct cgc atc ggc aaa gcg atc tac ggt tct      480
Val Gly Phe Glu Ser Gly Pro Arg Ile Gly Lys Ala Ile Tyr Gly Ser
145                 150                 155                 160 gac ctc ctg aac aac ggc tgg cac tgc ggt gcg gta tat ggc gca ccg      528
Asp Leu Leu Asn Asn Gly Trp His Cys Gly Ala Val Tyr Gly Ala Pro
                165                 170                 175 gct ggt gcg ctc gca act ggt aag ctg ctg ggc ctc acg ccg gac agc      576
Ala Gly Ala Leu Ala Thr Gly Lys Leu Leu Gly Leu Thr Pro Asp Ser
            180                 185                 190 atg gaa gat gca ctg ggt att gcc tgc acg caa gca tgc ggc ctc atg      624
Met Glu Asp Ala Leu Gly Ile Ala Cys Thr Gln Ala Cys Gly Leu Met
        195                 200                 205 tcc gcg cag tat ggt ggc atg gtt aaa cgt gtt cag cac ggt ttc gca      672
Ser Ala Gln Tyr Gly Gly Met Val Lys Arg Val Gln His Gly Phe Ala
    210                 215                 220 gcg cgt aat ggt ctc ctc ggt ggc ctc ctg gct cac ggc ggc tac gag      720
Ala Arg Asn Gly Leu Leu Gly Gly Leu Leu Ala His Gly Gly Tyr Glu
225                 230                 235                 240 gcg atg aaa ggt gtt ctc gag cgt tct tac ggt ggc ttc ctg aag atg      768
Ala Met Lys Gly Val Leu Glu Arg Ser Tyr Gly Gly Phe Leu Lys Met
                245                 250                 255 ttc acc aag ggc aac ggt cgt gaa ccg ccg tac aaa gaa gaa gag gtt      816
Phe Thr Lys Gly Asn Gly Arg Glu Pro Pro Tyr Lys Glu Glu Glu Val
            260                 265                 270 gtg gct ggt ctg ggt agc ttc tgg cac acc ttc acc att cgt atc aaa      864
Val Ala Gly Leu Gly Ser Phe Trp His Thr Phe Thr Ile Arg Ile Lys
        275                 280                 285 ctg tac gcg tgc tgc ggt ctc gta cac ggt cct gtt gaa gcc att gaa      912
Leu Tyr Ala Cys Cys Gly Leu Val His Gly Pro Val Glu Ala Ile Glu
    290                 295                 300 aac ctc cag ggt cgt tac ccg gaa ctg ctc aat cgt gct aac ctg tct      960
Asn Leu Gln Gly Arg Tyr Pro Glu Leu Leu Asn Arg Ala Asn Leu Ser
305                 310                 315                 320 aac atc cgc cac gtt cac gta caa ctc tct acc gcg agc aac tcc cac     1008
Asn Ile Arg His Val His Val Gln Leu Ser Thr Ala Ser Asn Ser His
                325                 330                 335 tgt ggt tgg atc cca gaa gag cgc cca atc tct tct atc gcg ggt caa     1056
Cys Gly Trp Ile Pro Glu Glu Arg Pro Ile Ser Ser Ile Ala Gly Gln
            340                 345                 350
```

```
atg tct gtc gca tat atc ctc gcc gtt cag ctc gtt gac caa cag tgt      1104
Met Ser Val Ala Tyr Ile Leu Ala Val Gln Leu Val Asp Gln Gln Cys
        355                 360                 365 ctg ctc agc cag ttc tcc gag ttt gac gat aat ctg gaa cgc ccg gaa      1152
Leu Leu Ser Gln Phe Ser Glu Phe Asp Asp Asn Leu Glu Arg Pro Glu
    370                 375                 380 gtg tgg gac ctg gca cgt aag gtt acc agc tct caa tct gag gag ttc      1200
Val Trp Asp Leu Ala Arg Lys Val Thr Ser Ser Gln Ser Glu Glu Phe
385                 390                 395                 400 gac cag gac ggt aac tgt ctc tct gcc ggt cgc gtc cgt att gag ttc      1248
Asp Gln Asp Gly Asn Cys Leu Ser Ala Gly Arg Val Arg Ile Glu Phe
                405                 410                 415 aac gac ggc tcc tcc atc acc gaa tcc gtt gag aag ccg ctc ggt gta      1296
Asn Asp Gly Ser Ser Ile Thr Glu Ser Val Glu Lys Pro Leu Gly Val
            420                 425                 430 aag gaa cca atg cca aat gaa cgc atc ctg cac aaa tac cgt acc ctg      1344
Lys Glu Pro Met Pro Asn Glu Arg Ile Leu His Lys Tyr Arg Thr Leu
        435                 440                 445 gcg ggt tct gta acg gac gaa agc cgt gtt aag gag atc gag gat ctc      1392
Ala Gly Ser Val Thr Asp Glu Ser Arg Val Lys Glu Ile Glu Asp Leu
    450                 455                 460 gtg ctc ggc ctg gac cgt ctg acc gat att agc ccg ctc ctc gag ctg      1440
Val Leu Gly Leu Asp Arg Leu Thr Asp Ile Ser Pro Leu Leu Glu Leu
465                 470                 475                 480 ctg aat tgt ccg gtt aaa tcc cca ctg ggt att gaa ttt ggt ccg ggt      1488
Leu Asn Cys Pro Val Lys Ser Pro Leu Gly Ile Glu Phe Gly Pro Gly
                485                 490                 495 cca ggt cct ggt cct ggc cct cta gaa gtg ttg ttc caa ggt cct ggt      1536
Pro Gly Pro Gly Pro Gly Pro Leu Glu Val Leu Phe Gln Gly Pro Gly
            500                 505                 510 cgt gcg aaa ctc atg ctg gct agt cgt gtt tca atc aaa gct cca cgc      1584
Arg Ala Lys Leu Met Leu Ala Ser Arg Val Ser Ile Lys Ala Pro Arg
        515                 520                 525 ctt gca cgt agc ctt gcg act acc act aat gcc tcc ctc aac ttg gac      1632
Leu Ala Arg Ser Leu Ala Thr Thr Thr Asn Ala Ser Leu Asn Leu Asp
    530                 535                 540 tcc aag gtc cga atg aac aac tgg gag gcc aac aac ttc ctc aac ttc      1680
Ser Lys Val Arg Met Asn Asn Trp Glu Ala Asn Asn Phe Leu Asn Phe
545                 550                 555                 560 aag aag cac acc gag aac gtc cag att gtc aag gag cga ctc aac cga      1728
Lys Lys His Thr Glu Asn Val Gln Ile Val Lys Glu Arg Leu Asn Arg
                565                 570                 575 ccc ctg acc tac gct gag aag att ctc tac ggc cat ctc gac aag ccc      1776
Pro Leu Thr Tyr Ala Glu Lys Ile Leu Tyr Gly His Leu Asp Lys Pro
            580                 585                 590 cat gag cag gag att gtc cga ggt cag tcc tac ctc aag ctg cga ccc      1824
His Glu Gln Glu Ile Val Arg Gly Gln Ser Tyr Leu Lys Leu Arg Pro
        595                 600                 605 gat cga gcc gcc tgc cag gat gcc acc gcc cag atg gcc att ctg cag      1872
Asp Arg Ala Ala Cys Gln Asp Ala Thr Ala Gln Met Ala Ile Leu Gln
    610                 615                 620 ttc atg tct gcc ggt atc ccc acc gtc cag acc ccc acc acc gtc cac      1920
Phe Met Ser Ala Gly Ile Pro Thr Val Gln Thr Pro Thr Thr Val His
625                 630                 635                 640 tgt gac cat ctt atc cag gcc cag gtt ggt ggt gag cag gat ctt gct      1968
Cys Asp His Leu Ile Gln Ala Gln Val Gly Gly Glu Gln Asp Leu Ala
                645                 650                 655 cga gcc atc gac atc aac aag gag gtc tac aac ttc ctt ggc acc gcc      2016
Arg Ala Ile Asp Ile Asn Lys Glu Val Tyr Asn Phe Leu Gly Thr Ala
```

```
                         660                 665                 670
tcc gcc aag tac gac att ggt ttc tgg aag gcc gga tcc ggt att atc          2064
Ser Ala Lys Tyr Asp Ile Gly Phe Trp Lys Ala Gly Ser Gly Ile Ile
        675                 680                 685 cac cag atc att ctc gag aac tac gcc ttc ccc ggt gcc ctt ctc att          2112
His Gln Ile Ile Leu Glu Asn Tyr Ala Phe Pro Gly Ala Leu Leu Ile
690                 695                 700 ggt tcc gac tct cat acc ccc aac gcc ggt ggt ctc ggt atg ctc gcc          2160
Gly Ser Asp Ser His Thr Pro Asn Ala Gly Gly Leu Gly Met Leu Ala
705                 710                 715                 720 atc ggt gtc ggt ggt gcc gat gtc gtc gac gtc atg gcc ggt ctc ccc          2208
Ile Gly Val Gly Gly Ala Asp Val Val Asp Val Met Ala Gly Leu Pro
            725                 730                 735 tgg gag ctt aag gcc ccc aag att atc ggt gtc aag ctg acc ggt aag          2256
Trp Glu Leu Lys Ala Pro Lys Ile Ile Gly Val Lys Leu Thr Gly Lys
                740                 745                 750 ctc tct ggc tgg acc tcc ccc aag gat att atc ctg aag gtc gct ggt          2304
Leu Ser Gly Trp Thr Ser Pro Lys Asp Ile Ile Leu Lys Val Ala Gly
            755                 760                 765 atc ctc acc gtc aag ggt gga acc ggt gct atc gtc gag tac ttc ggt          2352
Ile Leu Thr Val Lys Gly Gly Thr Gly Ala Ile Val Glu Tyr Phe Gly
770                 775                 780 gat ggt gtc gat aac ctg tcc tgc act ggt atg gga acc atc tgt aac          2400
Asp Gly Val Asp Asn Leu Ser Cys Thr Gly Met Gly Thr Ile Cys Asn
785                 790                 795                 800 atg ggt gcc gag att ggt gct acc acc tcc acc ttc ccc ttc aac gag          2448
Met Gly Ala Glu Ile Gly Ala Thr Thr Ser Thr Phe Pro Phe Asn Glu
                805                 810                 815 cga atg gcc gac tac ctt aac gcc act ggc cga aag gag att gcc gac          2496
Arg Met Ala Asp Tyr Leu Asn Ala Thr Gly Arg Lys Glu Ile Ala Asp
            820                 825                 830 ttt gct cga ctt tac aac cac ttc ctc tct gcc gat gag ggt tgt gag          2544
Phe Ala Arg Leu Tyr Asn His Phe Leu Ser Ala Asp Glu Gly Cys Glu
            835                 840                 845 tac gat cag ctc atc gag att gac ctg aac acc ctt gag cct tac gtc          2592
Tyr Asp Gln Leu Ile Glu Ile Asp Leu Asn Thr Leu Glu Pro Tyr Val
850                 855                 860 aac ggt ccc ttc act ccc gat ctt gcc acc ccc atc tcc aag ctc aag          2640
Asn Gly Pro Phe Thr Pro Asp Leu Ala Thr Pro Ile Ser Lys Leu Lys
865                 870                 875                 880 gat gtc gcc gtc gag aac gga tgg ccc ctt gag gtc aag gtc ggt ctt          2688
Asp Val Ala Val Glu Asn Gly Trp Pro Leu Glu Val Lys Val Gly Leu
                885                 890                 895 atc ggc tct tgc acc aac tcc tct tac gag gat atg gag cga tcc gcc          2736
Ile Gly Ser Cys Thr Asn Ser Ser Tyr Glu Asp Met Glu Arg Ser Ala
            900                 905                 910 tcc att gcc aag gac gcc atg gcc cac ggt ctt aag tcc aag tcc atc          2784
Ser Ile Ala Lys Asp Ala Met Ala His Gly Leu Lys Ser Lys Ser Ile
        915                 920                 925 tac acc gtc acc ccc ggt tcc gag cag atc cga gcc acc att gag cga          2832
Tyr Thr Val Thr Pro Gly Ser Glu Gln Ile Arg Ala Thr Ile Glu Arg
    930                 935                 940 gat ggt cag ctc cag acc ttc ctc gac ttc ggt ggt atc gtc ctt gct          2880
Asp Gly Gln Leu Gln Thr Phe Leu Asp Phe Gly Gly Ile Val Leu Ala
945                 950                 955                 960 aac gct tgt ggc ccc tgc att ggt cag tgg gac cga cga gac atc aag          2928
Asn Ala Cys Gly Pro Cys Ile Gly Gln Trp Asp Arg Arg Asp Ile Lys
                965                 970                 975 aag ggt gag aag aac acc att gtc tct tct tac aac cga aac ttc act          2976
```

```
                Lys Gly Glu Lys Asn Thr Ile Val Ser Ser Tyr Asn Arg Asn Phe Thr
                            980                 985                 990 ggc cga aac gat tct aac cct gcc  acc cac gct ttc gtc  acc tct ccc          3024
Gly Arg Asn Asp Ser Asn Pro Ala  Thr His Ala Phe Val  Thr Ser Pro
            995                 1000                1005 gat ctc gtc acc gct ttc gcc att gct ggt gac ctc cga ttc aac                3069
Asp Leu Val Thr Ala Phe Ala Ile Ala Gly Asp Leu Arg Phe Asn
    1010                1015                1020 cct ctc act gac tcc ctg aag gat tct gag ggt aag gag ttc aag                3114
Pro Leu Thr Asp Ser Leu Lys Asp Ser Glu Gly Lys Glu Phe Lys
    1025                1030                1035 ctc aag gag ccc act gga aag ggt ctg ccc gac cga ggt tac gac                3159
Leu Lys Glu Pro Thr Gly Lys Gly Leu Pro Asp Arg Gly Tyr Asp
    1040                1045                1050 ccc ggc atg gac acc tac cag gct ccc ccc gcc gac cga tct gcc                3204
Pro Gly Met Asp Thr Tyr Gln Ala Pro Pro Ala Asp Arg Ser Ala
    1055                1060                1065 gtc gag gtt gat gtt tcc ccc act tcc gac cga ctc cag atc ctc                3249
Val Glu Val Asp Val Ser Pro Thr Ser Asp Arg Leu Gln Ile Leu
    1070                1075                1080 aag ccc ttc aag cct tgg gac ggc aag gac ggt att gac atg ccc                3294
Lys Pro Phe Lys Pro Trp Asp Gly Lys Asp Gly Ile Asp Met Pro
    1085                1090                1095 atc ctc atc aag tct ctt ggt aag acc acc act gac cat atc tct                3339
Ile Leu Ile Lys Ser Leu Gly Lys Thr Thr Thr Asp His Ile Ser
    1100                1105                1110 cag gcc ggt ccc tgg ctt aag tac cga ggc cat ctc cag aac atc                3384
Gln Ala Gly Pro Trp Leu Lys Tyr Arg Gly His Leu Gln Asn Ile
    1115                1120                1125 tcc aac aac tac atg att gga gcc atc aac gct gag aac gag gag                3429
Ser Asn Asn Tyr Met Ile Gly Ala Ile Asn Ala Glu Asn Glu Glu
    1130                1135                1140 gcc aac aac gtc cga aac cag atc act ggc gag tgg gga gga gtt                3474
Ala Asn Asn Val Arg Asn Gln Ile Thr Gly Glu Trp Gly Gly Val
    1145                1150                1155 ccc gag act gcc att gct tac cga gac aac ggt cga tgg gtt                    3519
Pro Glu Thr Ala Ile Ala Tyr Arg Asp Asn Gly Ile Arg Trp Val
    1160                1165                1170 gtt gtc gga ggt gat aac ttc ggt gag ggt tct tct cga gag cac                3564
Val Val Gly Gly Asp Asn Phe Gly Glu Gly Ser Ser Arg Glu His
    1175                1180                1185 gct gct ctt gag ccc cga ttc ctc ggt ggt ttc gcc atc atc acc                3609
Ala Ala Leu Glu Pro Arg Phe Leu Gly Gly Phe Ala Ile Ile Thr
    1190                1195                1200 aag tct ttt gcc cga att cac gag act aac ctg aag aag cag ggt                3654
Lys Ser Phe Ala Arg Ile His Glu Thr Asn Leu Lys Lys Gln Gly
    1205                1210                1215 ctc ctg ccc ctt aac ttc gtc aac ggt gct gac tac gac aag atc                3699
Leu Leu Pro Leu Asn Phe Val Asn Gly Ala Asp Tyr Asp Lys Ile
    1220                1225                1230 cag ccc tcc gat aag atc tcc att ctt ggt ctt aag gac ctt gcc                3744
Gln Pro Ser Asp Lys Ile Ser Ile Leu Gly Leu Lys Asp Leu Ala
    1235                1240                1245 ccc ggc aag aac gtc acc att gag gtt acc ccc aag gac ggt gcc                3789
Pro Gly Lys Asn Val Thr Ile Glu Val Thr Pro Lys Asp Gly Ala
    1250                1255                1260 aag tgg acc acc gag gtt tct cac acc tac aac tct gag cag ctc                3834
Lys Trp Thr Thr Glu Val Ser His Thr Tyr Asn Ser Glu Gln Leu
    1265                1270                1275
```

```
              gag tgg ttc aag tac ggc tct gcc ctc aac aag atg gct gcc tcc      3879
              Glu Trp Phe Lys Tyr Gly Ser Ala Leu Asn Lys Met Ala Ala Ser
                  1280                1285                1290 aag aaa taa                                                      3888
              Lys Lys
                  1295

<210> SEQ ID NO 15
<211> LENGTH: 1295
<212> TYPE: PRT
<213> ORGANISM: Artificial sequence
<220> FEATURE:
<223> OTHER INFORMATION: Synthetic Construct

<400> SEQUENCE: 15

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Ile Pro Ser
                20                  25                  30

Asp Val Leu Glu Arg Ala Lys Tyr Leu Ile Leu Asp Gly Ile Ala Cys
            35                  40                  45

Ala Trp Val Gly Ala Arg Val Pro Trp Ser Glu Lys Tyr Val Gln Ala
        50                  55                  60

Thr Met Ser Phe Glu Pro Pro Gly Ala Cys Arg Val Ile Gly Tyr Gly
65              70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
130             135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
    290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
```

-continued

```
                325                 330                 335
Cys Gly Trp Ile Pro Glu Glu Arg Pro Ile Ser Ser Ile Ala Gly Gln
            340                 345                 350
Met Ser Val Ala Tyr Ile Leu Ala Val Gln Leu Val Asp Gln Gln Cys
            355                 360                 365
Leu Leu Ser Gln Phe Ser Glu Phe Asp Asp Asn Leu Glu Arg Pro Glu
            370                 375                 380
Val Trp Asp Leu Ala Arg Lys Val Thr Ser Ser Gln Ser Glu Glu Phe
385                 390                 395                 400
Asp Gln Asp Gly Asn Cys Leu Ser Ala Gly Arg Val Arg Ile Glu Phe
                405                 410                 415
Asn Asp Gly Ser Ser Ile Thr Glu Ser Val Glu Lys Pro Leu Gly Val
            420                 425                 430
Lys Glu Pro Met Pro Asn Glu Arg Ile Leu His Lys Tyr Arg Thr Leu
            435                 440                 445
Ala Gly Ser Val Thr Asp Glu Ser Arg Val Lys Glu Ile Glu Asp Leu
            450                 455                 460
Val Leu Gly Leu Asp Arg Leu Thr Asp Ile Ser Pro Leu Leu Glu Leu
465                 470                 475                 480
Leu Asn Cys Pro Val Lys Ser Pro Leu Gly Ile Glu Phe Gly Pro Gly
                485                 490                 495
Pro Gly Pro Gly Pro Gly Pro Leu Glu Val Leu Phe Gln Gly Pro Gly
            500                 505                 510
Arg Ala Lys Leu Met Leu Ala Ser Arg Val Ser Ile Lys Ala Pro Arg
            515                 520                 525
Leu Ala Arg Ser Leu Ala Thr Thr Asn Ala Ser Leu Asn Leu Asp
            530                 535                 540
Ser Lys Val Arg Met Asn Asn Trp Glu Ala Asn Asn Phe Leu Asn Phe
545                 550                 555                 560
Lys Lys His Thr Glu Asn Val Gln Ile Val Lys Glu Arg Leu Asn Arg
                565                 570                 575
Pro Leu Thr Tyr Ala Glu Lys Ile Leu Tyr Gly His Leu Asp Lys Pro
            580                 585                 590
His Glu Gln Glu Ile Val Arg Gly Gln Ser Tyr Leu Lys Leu Arg Pro
            595                 600                 605
Asp Arg Ala Ala Cys Gln Asp Ala Thr Ala Gln Met Ala Ile Leu Gln
            610                 615                 620
Phe Met Ser Ala Gly Ile Pro Thr Val Gln Thr Pro Thr Thr Val His
625                 630                 635                 640
Cys Asp His Leu Ile Gln Ala Gln Val Gly Gly Glu Gln Asp Leu Ala
                645                 650                 655
Arg Ala Ile Asp Ile Asn Lys Glu Val Tyr Asn Phe Leu Gly Thr Ala
            660                 665                 670
Ser Ala Lys Tyr Asp Ile Gly Phe Trp Lys Ala Gly Ser Gly Ile Ile
            675                 680                 685
His Gln Ile Ile Leu Glu Asn Tyr Ala Phe Pro Gly Ala Leu Leu Ile
            690                 695                 700
Gly Ser Asp Ser His Thr Pro Asn Ala Gly Gly Leu Gly Met Leu Ala
705                 710                 715                 720
Ile Gly Val Gly Gly Ala Asp Val Val Asp Val Met Ala Gly Leu Pro
                725                 730                 735
Trp Glu Leu Lys Ala Pro Lys Ile Ile Gly Val Lys Leu Thr Gly Lys
            740                 745                 750
```

-continued

```
Leu Ser Gly Trp Thr Ser Pro Lys Asp Ile Ile Leu Lys Val Ala Gly
            755                 760                 765

Ile Leu Thr Val Lys Gly Thr Gly Ala Ile Val Glu Tyr Phe Gly
        770                 775                 780

Asp Gly Val Asp Asn Leu Ser Cys Thr Gly Met Gly Thr Ile Cys Asn
785                 790                 795                 800

Met Gly Ala Glu Ile Gly Ala Thr Thr Ser Thr Phe Pro Phe Asn Glu
                805                 810                 815

Arg Met Ala Asp Tyr Leu Asn Ala Thr Gly Arg Lys Glu Ile Ala Asp
                820                 825                 830

Phe Ala Arg Leu Tyr Asn His Phe Leu Ser Ala Asp Glu Gly Cys Glu
                835                 840                 845

Tyr Asp Gln Leu Ile Glu Ile Asp Leu Asn Thr Leu Glu Pro Tyr Val
        850                 855                 860

Asn Gly Pro Phe Thr Pro Asp Leu Ala Thr Pro Ile Ser Lys Leu Lys
865                 870                 875                 880

Asp Val Ala Val Glu Asn Gly Trp Pro Leu Glu Val Lys Val Gly Leu
                885                 890                 895

Ile Gly Ser Cys Thr Asn Ser Ser Tyr Glu Asp Met Glu Arg Ser Ala
                900                 905                 910

Ser Ile Ala Lys Asp Ala Met Ala His Gly Leu Lys Ser Lys Ser Ile
                915                 920                 925

Tyr Thr Val Thr Pro Gly Ser Glu Gln Ile Arg Ala Thr Ile Glu Arg
        930                 935                 940

Asp Gly Gln Leu Gln Thr Phe Leu Asp Phe Gly Gly Ile Val Leu Ala
945                 950                 955                 960

Asn Ala Cys Gly Pro Cys Ile Gly Gln Trp Asp Arg Arg Asp Ile Lys
                965                 970                 975

Lys Gly Glu Lys Asn Thr Ile Val Ser Ser Tyr Asn Arg Asn Phe Thr
                980                 985                 990

Gly Arg Asn Asp Ser Asn Pro Ala Thr His Ala Phe Val Thr Ser Pro
        995                 1000                1005

Asp Leu Val Thr Ala Phe Ala Ile Ala Gly Asp Leu Arg Phe Asn
        1010                1015                1020

Pro Leu Thr Asp Ser Leu Lys Asp Ser Glu Gly Lys Glu Phe Lys
        1025                1030                1035

Leu Lys Glu Pro Thr Gly Lys Gly Leu Pro Asp Arg Gly Tyr Asp
        1040                1045                1050

Pro Gly Met Asp Thr Tyr Gln Ala Pro Pro Ala Asp Arg Ser Ala
        1055                1060                1065

Val Glu Val Asp Val Ser Pro Thr Ser Asp Arg Leu Gln Ile Leu
        1070                1075                1080

Lys Pro Phe Lys Pro Trp Asp Gly Lys Asp Gly Ile Asp Met Pro
        1085                1090                1095

Ile Leu Ile Lys Ser Leu Gly Lys Thr Thr Thr Asp His Ile Ser
        1100                1105                1110

Gln Ala Gly Pro Trp Leu Lys Tyr Arg Gly His Leu Gln Asn Ile
        1115                1120                1125

Ser Asn Asn Tyr Met Ile Gly Ala Ile Asn Ala Glu Asn Glu Glu
        1130                1135                1140

Ala Asn Asn Val Arg Asn Gln Ile Thr Gly Glu Trp Gly Gly Val
        1145                1150                1155
```

```
Pro Glu Thr Ala Ile Ala Tyr Arg Asp Asn Gly Ile Arg Trp Val
    1160            1165                1170

Val Val Gly Gly Asp Asn Phe Gly Glu Gly Ser Ser Arg Glu His
    1175            1180                1185

Ala Ala Leu Glu Pro Arg Phe Leu Gly Gly Phe Ala Ile Ile Thr
    1190            1195                1200

Lys Ser Phe Ala Arg Ile His Glu Thr Asn Leu Lys Lys Gln Gly
    1205            1210                1215

Leu Leu Pro Leu Asn Phe Val Asn Gly Ala Asp Tyr Asp Lys Ile
    1220            1225                1230

Gln Pro Ser Asp Lys Ile Ser Ile Leu Gly Leu Lys Asp Leu Ala
    1235            1240                1245

Pro Gly Lys Asn Val Thr Ile Glu Val Thr Pro Lys Asp Gly Ala
    1250            1255                1260

Lys Trp Thr Thr Glu Val Ser His Thr Tyr Asn Ser Glu Gln Leu
    1265            1270                1275

Glu Trp Phe Lys Tyr Gly Ser Ala Leu Asn Lys Met Ala Ala Ser
    1280            1285                1290

Lys Lys
    1295

<210> SEQ ID NO 16
<211> LENGTH: 1251
<212> TYPE: DNA
<213> ORGANISM: Escherichia coli
<220> FEATURE:
<221> NAME/KEY: CDS
<222> LOCATION: (1)..(1251)
<223> OTHER INFORMATION: isocitrate dehydrogenase

<400> SEQUENCE: 16 atg gaa agt aaa gta gtt gtt ccg gca caa ggc aag aag atc acc ctg      48
Met Glu Ser Lys Val Val Val Pro Ala Gln Gly Lys Lys Ile Thr Leu
1               5                   10                  15 caa aac ggc aaa ctc aac gtt cct gaa aat ccg att atc cct tac att      96
Gln Asn Gly Lys Leu Asn Val Pro Glu Asn Pro Ile Ile Pro Tyr Ile
                20                  25                  30 gaa ggt gat gga atc ggt gta gat gta acc cca gcc atg ctg aaa gtg     144
Glu Gly Asp Gly Ile Gly Val Asp Val Thr Pro Ala Met Leu Lys Val
            35                  40                  45 gtc gac gct gca gtc gag aaa gcc tat aaa ggc gag cgt aaa atc tcc     192
Val Asp Ala Ala Val Glu Lys Ala Tyr Lys Gly Glu Arg Lys Ile Ser
        50                  55                  60 tgg atg gaa att tac acc ggt gaa aaa tcc aca cag gtt tat ggt cag     240
Trp Met Glu Ile Tyr Thr Gly Glu Lys Ser Thr Gln Val Tyr Gly Gln
65                  70                  75                  80 gac gtc tgg ctg cct gct gaa act ctt gat ctg att cgt gaa tat cgc     288
Asp Val Trp Leu Pro Ala Glu Thr Leu Asp Leu Ile Arg Glu Tyr Arg
                85                  90                  95 gtt gcc att aaa ggt ccg ctg acc act ccg gtt ggt ggc ggt att cgc     336
Val Ala Ile Lys Gly Pro Leu Thr Thr Pro Val Gly Gly Gly Ile Arg
                100                 105                 110 tct ctg aac gtt gcc ctg cgc cag gaa ctg gat ctc tac atc tgc ctg     384
Ser Leu Asn Val Ala Leu Arg Gln Glu Leu Asp Leu Tyr Ile Cys Leu
            115                 120                 125 cgt ccg gta cgt tac tat cag ggc act cca agc ccg gtt aaa cac cct     432
Arg Pro Val Arg Tyr Tyr Gln Gly Thr Pro Ser Pro Val Lys His Pro
        130                 135                 140 gaa ctg acc gat atg gtt atc ttc cgt gaa aac tcg gaa gac att tat     480
```

| | | | | | | | | | | | | | |
|---|---|---|---|---|---|---|---|---|---|---|---|---|---|
| Glu | Leu | Thr | Asp | Met | Val | Ile | Phe | Arg | Glu | Asn | Ser | Glu | Asp | Ile | Tyr |
| 145 | | | | | 150 | | | | | 155 | | | | | 160 |

```
gcg ggt atc gaa tgg aaa gca gac tct gcc gac gcc gag aaa gtg att    528
Ala Gly Ile Glu Trp Lys Ala Asp Ser Ala Asp Ala Glu Lys Val Ile
            165                 170                 175 aaa ttc ctg cgt gaa gag atg ggg gtg aag aaa att cgc ttc ccg gaa    576
Lys Phe Leu Arg Glu Glu Met Gly Val Lys Lys Ile Arg Phe Pro Glu
        180                 185                 190 cat tgt ggt atc ggt att aag ccg tgt tcg gaa gaa ggc acc aaa cgt    624
His Cys Gly Ile Gly Ile Lys Pro Cys Ser Glu Glu Gly Thr Lys Arg
    195                 200                 205 ctg gtt cgt gca gcg atc gaa tac gca att gct aac gat cgt gac tct    672
Leu Val Arg Ala Ala Ile Glu Tyr Ala Ile Ala Asn Asp Arg Asp Ser
210                 215                 220 gtg act ctg gtg cac aaa ggc aac atc atg aag ttc acc gaa gga gcg    720
Val Thr Leu Val His Lys Gly Asn Ile Met Lys Phe Thr Glu Gly Ala
225                 230                 235                 240 ttt aaa gac tgg ggc tac cag ctg gcg cgt gaa gag ttt ggc ggt gaa    768
Phe Lys Asp Trp Gly Tyr Gln Leu Ala Arg Glu Glu Phe Gly Gly Glu
                245                 250                 255 ctg atc gac ggt ggc ccg tgg ctg aaa gtt aaa aac ccg aac act ggc    816
Leu Ile Asp Gly Gly Pro Trp Leu Lys Val Lys Asn Pro Asn Thr Gly
            260                 265                 270 aaa gag atc gtc att aaa gac gtg att gct gat gca ttc ctg caa cag    864
Lys Glu Ile Val Ile Lys Asp Val Ile Ala Asp Ala Phe Leu Gln Gln
        275                 280                 285 atc ctg ctg cgt ccg gct gaa tat gat gtt atc gcc tgt atg aac ctg    912
Ile Leu Leu Arg Pro Ala Glu Tyr Asp Val Ile Ala Cys Met Asn Leu
    290                 295                 300 aac ggt gac tac att tct gac gcc ctg gca gcg cag gtt ggc ggt atc    960
Asn Gly Asp Tyr Ile Ser Asp Ala Leu Ala Ala Gln Val Gly Gly Ile
305                 310                 315                 320 ggt atc gcc cct ggt gca aac atc ggt gac gaa tgc gcc ctg ttt gaa   1008
Gly Ile Ala Pro Gly Ala Asn Ile Gly Asp Glu Cys Ala Leu Phe Glu
                325                 330                 335 gcc acc cac ggt act gcg ccg aaa tat gcc ggt cag gac aaa gta aat   1056
Ala Thr His Gly Thr Ala Pro Lys Tyr Ala Gly Gln Asp Lys Val Asn
            340                 345                 350 cct ggc tct att att ctc tcc gct gag atg atg ctg cgc cac atg ggt   1104
Pro Gly Ser Ile Ile Leu Ser Ala Glu Met Met Leu Arg His Met Gly
        355                 360                 365 tgg acc gaa gcg gct gac tta att gtt aaa ggt atg gaa ggc gca atc   1152
Trp Thr Glu Ala Ala Asp Leu Ile Val Lys Gly Met Glu Gly Ala Ile
    370                 375                 380 aac gcg aaa acc gta acc tat gac ttc gag cgt ctg atg gat ggc gct   1200
Asn Ala Lys Thr Val Thr Tyr Asp Phe Glu Arg Leu Met Asp Gly Ala
385                 390                 395                 400 aaa ctg ctg aaa tgt tca gag ttt ggt gac gcg atc atc gaa aac atg   1248
Lys Leu Leu Lys Cys Ser Glu Phe Gly Asp Ala Ile Ile Glu Asn Met
                405                 410                 415 taa                                                               1251
```

<210> SEQ ID NO 17
<211> LENGTH: 416
<212> TYPE: PRT
<213> ORGANISM: Escherichia coli

<400> SEQUENCE: 17

| | | | | | | | | | | | | | | |
|---|---|---|---|---|---|---|---|---|---|---|---|---|---|---|
| Met | Glu | Ser | Lys | Val | Val | Val | Pro | Ala | Gln | Gly | Lys | Lys | Ile | Thr | Leu |
| 1 | | | | 5 | | | | | 10 | | | | | 15 | |

```
Gln Asn Gly Lys Leu Asn Val Pro Glu Asn Pro Ile Ile Pro Tyr Ile
                 20                  25                  30

Glu Gly Asp Gly Ile Gly Val Asp Val Thr Pro Ala Met Leu Lys Val
             35                  40                  45

Val Asp Ala Ala Val Glu Lys Ala Tyr Lys Gly Glu Arg Lys Ile Ser
 50                  55                  60

Trp Met Glu Ile Tyr Thr Gly Glu Lys Ser Thr Gln Val Tyr Gly Gln
 65                  70                  75                  80

Asp Val Trp Leu Pro Ala Glu Thr Leu Asp Leu Ile Arg Glu Tyr Arg
                 85                  90                  95

Val Ala Ile Lys Gly Pro Leu Thr Thr Pro Val Gly Gly Gly Ile Arg
                100                 105                 110

Ser Leu Asn Val Ala Leu Arg Gln Glu Leu Asp Leu Tyr Ile Cys Leu
                115                 120                 125

Arg Pro Val Arg Tyr Tyr Gln Gly Thr Pro Ser Pro Val Lys His Pro
130                 135                 140

Glu Leu Thr Asp Met Val Ile Phe Arg Glu Asn Ser Glu Asp Ile Tyr
145                 150                 155                 160

Ala Gly Ile Glu Trp Lys Ala Asp Ser Ala Asp Ala Glu Lys Val Ile
                165                 170                 175

Lys Phe Leu Arg Glu Glu Met Gly Val Lys Lys Ile Arg Phe Pro Glu
                180                 185                 190

His Cys Gly Ile Gly Ile Lys Pro Cys Ser Glu Gly Thr Lys Arg
                195                 200                 205

Leu Val Arg Ala Ala Ile Glu Tyr Ala Ile Ala Asn Asp Arg Asp Ser
                210                 215                 220

Val Thr Leu Val His Lys Gly Asn Ile Met Lys Phe Thr Glu Gly Ala
225                 230                 235                 240

Phe Lys Asp Trp Gly Tyr Gln Leu Ala Arg Glu Glu Phe Gly Gly Glu
                245                 250                 255

Leu Ile Asp Gly Gly Pro Trp Leu Lys Val Lys Asn Pro Asn Thr Gly
                260                 265                 270

Lys Glu Ile Val Ile Lys Asp Val Ile Ala Asp Ala Phe Leu Gln Gln
                275                 280                 285

Ile Leu Leu Arg Pro Ala Glu Tyr Asp Val Ile Ala Cys Met Asn Leu
                290                 295                 300

Asn Gly Asp Tyr Ile Ser Asp Ala Leu Ala Ala Gln Val Gly Gly Ile
305                 310                 315                 320

Gly Ile Ala Pro Gly Ala Asn Ile Gly Asp Glu Cys Ala Leu Phe Glu
                325                 330                 335

Ala Thr His Gly Thr Ala Pro Lys Tyr Ala Gly Gln Asp Lys Val Asn
                340                 345                 350

Pro Gly Ser Ile Ile Leu Ser Ala Glu Met Met Leu Arg His Met Gly
                355                 360                 365

Trp Thr Glu Ala Ala Asp Leu Ile Val Lys Gly Met Glu Gly Ala Ile
                370                 375                 380

Asn Ala Lys Thr Val Thr Tyr Asp Phe Glu Arg Leu Met Asp Gly Ala
385                 390                 395                 400

Lys Leu Leu Lys Cys Ser Glu Phe Gly Asp Ala Ile Ile Glu Asn Met
                405                 410                 415

<210> SEQ ID NO 18
<211> LENGTH: 2652
```

```
<212> TYPE: DNA
<213> ORGANISM: Escherichia coli
<220> FEATURE:
<221> NAME/KEY: CDS
<222> LOCATION: (1)..(2652)
<223> OTHER INFORMATION: phosphoenolpyruvate carboxylase

<400> SEQUENCE: 18 atg aac gaa caa tat tcc gca ttg cgt agt aat gtc agt atg ctc ggc      48
Met Asn Glu Gln Tyr Ser Ala Leu Arg Ser Asn Val Ser Met Leu Gly
 1               5                  10                  15 aaa gtg ctg gga gaa acc atc aag gat gcg ttg gga gaa cac att ctt      96
Lys Val Leu Gly Glu Thr Ile Lys Asp Ala Leu Gly Glu His Ile Leu
             20                  25                  30 gaa cgc gta gaa act atc cgt aag ttg tcg aaa tct tca cgc gct ggc     144
Glu Arg Val Glu Thr Ile Arg Lys Leu Ser Lys Ser Ser Arg Ala Gly
         35                  40                  45 aat gat gct aac cgc cag gag ttg ctc acc acc tta caa aat ttg tcg     192
Asn Asp Ala Asn Arg Gln Glu Leu Leu Thr Thr Leu Gln Asn Leu Ser
 50                  55                  60 aac gac gag ctg ctg ccc gtt gcg cgt gcg ttt agt cag ttc ctg aac     240
Asn Asp Glu Leu Leu Pro Val Ala Arg Ala Phe Ser Gln Phe Leu Asn
65                  70                  75                  80 ctg gcc aac acc gcc gag caa tac cac agc att tcg ccg aaa ggc gaa     288
Leu Ala Asn Thr Ala Glu Gln Tyr His Ser Ile Ser Pro Lys Gly Glu
                 85                  90                  95 gct gcc agc aac ccg gaa gtg atc gcc cgc acc ctg cgt aaa ctg aaa     336
Ala Ala Ser Asn Pro Glu Val Ile Ala Arg Thr Leu Arg Lys Leu Lys
            100                 105                 110 aac cag ccg gaa ctg agc gaa gac acc atc aaa aaa gca gtg gaa tcg     384
Asn Gln Pro Glu Leu Ser Glu Asp Thr Ile Lys Lys Ala Val Glu Ser
        115                 120                 125 ctg tcg ctg gaa ctg gtc ctc acg gct cac cca acc gaa att acc cgt     432
Leu Ser Leu Glu Leu Val Leu Thr Ala His Pro Thr Glu Ile Thr Arg
    130                 135                 140 cgt aca ctg atc cac aaa atg gtg gaa gtg aac gcc tgt tta aaa cag     480
Arg Thr Leu Ile His Lys Met Val Glu Val Asn Ala Cys Leu Lys Gln
145                 150                 155                 160 ctc gat aac aaa gat atc gct gac tac gaa cac aac cag ctg atg cgt     528
Leu Asp Asn Lys Asp Ile Ala Asp Tyr Glu His Asn Gln Leu Met Arg
                165                 170                 175 cgc ctg cgc cag ttg atc gcc cag tca tgg cat acc gat gaa atc cgt     576
Arg Leu Arg Gln Leu Ile Ala Gln Ser Trp His Thr Asp Glu Ile Arg
            180                 185                 190 aag ctg cgt cca agc ccg gta gat gaa gcc aaa tgg ggc ttt gcc gta     624
Lys Leu Arg Pro Ser Pro Val Asp Glu Ala Lys Trp Gly Phe Ala Val
        195                 200                 205 gtg gaa aac agc ctg tgg caa ggc gta cca aat tac ctg cgc gaa ctg     672
Val Glu Asn Ser Leu Trp Gln Gly Val Pro Asn Tyr Leu Arg Glu Leu
    210                 215                 220 aac gaa caa ctg gaa gag aac ctc ggc tac aaa ctg ccc gtc gaa ttt     720
Asn Glu Gln Leu Glu Glu Asn Leu Gly Tyr Lys Leu Pro Val Glu Phe
225                 230                 235                 240 gtt ccg gtc cgt ttt act tcg tgg atg ggc ggc gac cgc gac ggc aac     768
Val Pro Val Arg Phe Thr Ser Trp Met Gly Gly Asp Arg Asp Gly Asn
                245                 250                 255 ccg aac gtc act gcc gat atc acc cgc cac gtc ctg cta ctc agc cgc     816
Pro Asn Val Thr Ala Asp Ile Thr Arg His Val Leu Leu Leu Ser Arg
            260                 265                 270 tgg aaa gcc acc gat ttg ttc ctg aaa gat att cag gtg ctg gtt tct     864
Trp Lys Ala Thr Asp Leu Phe Leu Lys Asp Ile Gln Val Leu Val Ser
```

|   |   |   |   |   |   |   |   |   |   |   |   |   |   |   |   |   |
|---|---|---|---|---|---|---|---|---|---|---|---|---|---|---|---|---|
|   |   | 275 |   |   |   | 280 |   |   |   | 285 |   |   |   |   |   |   |
| gaa | ctg | tcg | atg | gtt | gaa | gcg | acc | cct | gaa | ctg | ctg | gcg | ctg | gtt | ggc | 912 |
| Glu | Leu | Ser | Met | Val | Glu | Ala | Thr | Pro | Glu | Leu | Leu | Ala | Leu | Val | Gly |   |
|   |   | 290 |   |   |   | 295 |   |   |   | 300 |   |   |   |   |   |   |
| gaa | gaa | ggt | gcc | gca | gaa | ccg | tat | cgc | tat | ctg | atg | aaa | aac | ctg | cgt | 960 |
| Glu | Glu | Gly | Ala | Ala | Glu | Pro | Tyr | Arg | Tyr | Leu | Met | Lys | Asn | Leu | Arg |   |
| 305 |   |   |   | 310 |   |   |   |   | 315 |   |   |   | 320 |   |   |   |
| tct | cgc | ctg | atg | gcg | aca | cag | gca | tgg | ctg | gaa | gcg | cgc | ctg | aaa | ggc | 1008 |
| Ser | Arg | Leu | Met | Ala | Thr | Gln | Ala | Trp | Leu | Glu | Ala | Arg | Leu | Lys | Gly |   |
|   |   |   |   | 325 |   |   |   | 330 |   |   |   |   | 335 |   |   |   |
| gaa | gaa | ctg | cca | aaa | cca | gaa | ggc | ctg | ctg | aca | caa | aac | gaa | gaa | ctg | 1056 |
| Glu | Glu | Leu | Pro | Lys | Pro | Glu | Gly | Leu | Leu | Thr | Gln | Asn | Glu | Glu | Leu |   |
|   |   | 340 |   |   |   | 345 |   |   |   | 350 |   |   |   |   |   |   |
| tgg | gaa | ccg | ctc | tac | gct | tgc | tac | cag | tca | ctt | cag | gcg | tgt | ggc | atg | 1104 |
| Trp | Glu | Pro | Leu | Tyr | Ala | Cys | Tyr | Gln | Ser | Leu | Gln | Ala | Cys | Gly | Met |   |
|   |   | 355 |   |   |   | 360 |   |   |   | 365 |   |   |   |   |   |   |
| ggt | att | atc | gcc | aac | ggc | gat | ctg | ctc | gac | acc | ctg | cgc | cgc | gtg | aaa | 1152 |
| Gly | Ile | Ile | Ala | Asn | Gly | Asp | Leu | Leu | Asp | Thr | Leu | Arg | Arg | Val | Lys |   |
| 370 |   |   |   | 375 |   |   |   |   | 380 |   |   |   |   |   |   |   |
| tgt | ttc | ggc | gta | ccg | ctg | gtc | cgt | att | gat | atc | cgt | cag | gag | agc | acg | 1200 |
| Cys | Phe | Gly | Val | Pro | Leu | Val | Arg | Ile | Asp | Ile | Arg | Gln | Glu | Ser | Thr |   |
| 385 |   |   |   | 390 |   |   |   |   | 395 |   |   |   | 400 |   |   |   |
| cgt | cat | acc | gaa | gcg | ctg | ggc | gag | ctg | acc | cgc | tac | ctc | ggt | atc | ggc | 1248 |
| Arg | His | Thr | Glu | Ala | Leu | Gly | Glu | Leu | Thr | Arg | Tyr | Leu | Gly | Ile | Gly |   |
|   |   |   |   | 405 |   |   |   | 410 |   |   |   |   | 415 |   |   |   |
| gac | tac | gaa | agc | tgg | tca | gag | gcc | gac | aaa | cag | gcg | ttc | ctg | atc | cgc | 1296 |
| Asp | Tyr | Glu | Ser | Trp | Ser | Glu | Ala | Asp | Lys | Gln | Ala | Phe | Leu | Ile | Arg |   |
|   |   |   |   | 420 |   |   |   | 425 |   |   |   |   | 430 |   |   |   |
| gaa | ctg | aac | tcc | aaa | cgt | ccg | ctt | ctg | ccg | cgc | aac | tgg | caa | cca | agc | 1344 |
| Glu | Leu | Asn | Ser | Lys | Arg | Pro | Leu | Leu | Pro | Arg | Asn | Trp | Gln | Pro | Ser |   |
|   |   | 435 |   |   |   | 440 |   |   |   | 445 |   |   |   |   |   |   |
| gcc | gaa | acg | cgc | gaa | gtg | ctc | gat | acc | tgc | cag | gtg | att | gcc | gaa | gca | 1392 |
| Ala | Glu | Thr | Arg | Glu | Val | Leu | Asp | Thr | Cys | Gln | Val | Ile | Ala | Glu | Ala |   |
|   |   | 450 |   |   |   | 455 |   |   |   | 460 |   |   |   |   |   |   |
| ccg | caa | ggc | tcc | att | gcc | gcc | tac | gtg | atc | tcg | atg | gcg | aaa | acg | ccg | 1440 |
| Pro | Gln | Gly | Ser | Ile | Ala | Ala | Tyr | Val | Ile | Ser | Met | Ala | Lys | Thr | Pro |   |
| 465 |   |   |   | 470 |   |   |   |   | 475 |   |   |   | 480 |   |   |   |
| tcc | gac | gta | ctg | gct | gtc | cac | ctg | ctg | ctg | aaa | gaa | gcg | ggt | atc | ggg | 1488 |
| Ser | Asp | Val | Leu | Ala | Val | His | Leu | Leu | Leu | Lys | Glu | Ala | Gly | Ile | Gly |   |
|   |   |   |   | 485 |   |   |   | 490 |   |   |   |   | 495 |   |   |   |
| ttt | gcg | atg | ccg | gtt | gct | ccg | ctg | ttt | gaa | acc | ctc | gat | gat | ctg | aac | 1536 |
| Phe | Ala | Met | Pro | Val | Ala | Pro | Leu | Phe | Glu | Thr | Leu | Asp | Asp | Leu | Asn |   |
|   |   |   |   | 500 |   |   |   | 505 |   |   |   |   | 510 |   |   |   |
| aac | gcc | aac | gat | gtc | atg | acc | cag | ctg | ctc | aat | att | gac | tgg | tat | cgt | 1584 |
| Asn | Ala | Asn | Asp | Val | Met | Thr | Gln | Leu | Leu | Asn | Ile | Asp | Trp | Tyr | Arg |   |
|   |   | 515 |   |   |   | 520 |   |   |   | 525 |   |   |   |   |   |   |
| ggc | ctg | att | cag | ggc | aaa | cag | atg | gtg | atg | att | ggc | tat | tcc | gac | tca | 1632 |
| Gly | Leu | Ile | Gln | Gly | Lys | Gln | Met | Val | Met | Ile | Gly | Tyr | Ser | Asp | Ser |   |
| 530 |   |   |   | 535 |   |   |   |   | 540 |   |   |   |   |   |   |   |
| gca | aaa | gat | gcg | gga | gtg | atg | gca | gct | tcc | tgg | gcg | caa | tat | cag | gca | 1680 |
| Ala | Lys | Asp | Ala | Gly | Val | Met | Ala | Ala | Ser | Trp | Ala | Gln | Tyr | Gln | Ala |   |
| 545 |   |   |   | 550 |   |   |   |   | 555 |   |   |   | 560 |   |   |   |
| cag | gat | gca | tta | atc | aaa | acc | tgc | gaa | aaa | gcg | ggt | att | gag | ctg | acg | 1728 |
| Gln | Asp | Ala | Leu | Ile | Lys | Thr | Cys | Glu | Lys | Ala | Gly | Ile | Glu | Leu | Thr |   |
|   |   |   |   | 565 |   |   |   | 570 |   |   |   |   | 575 |   |   |   |
| ttg | ttc | cac | ggt | cgc | ggc | ggt | tcc | att | ggt | cgc | ggc | ggc | gca | cct | gct | 1776 |
| Leu | Phe | His | Gly | Arg | Gly | Gly | Ser | Ile | Gly | Arg | Gly | Gly | Ala | Pro | Ala |   |
|   |   |   |   | 580 |   |   |   | 585 |   |   |   |   | 590 |   |   |   |
| cat | gcg | gcg | ctg | ctg | tca | caa | ccg | cca | gga | agc | ctg | aaa | ggc | ggc | ctg | 1824 |

```
His Ala Ala Leu Leu Ser Gln Pro Gly Ser Leu Lys Gly Gly Leu
            595                 600                 605 cgc gta acc gaa cag ggc gag atg atc cgc ttt aaa tat ggt ctg cca      1872
Arg Val Thr Glu Gln Gly Glu Met Ile Arg Phe Lys Tyr Gly Leu Pro
610                 615                 620 gaa atc acc gtc agc agc ctg tcg ctt tat acc ggg gcg att ctg gaa      1920
Glu Ile Thr Val Ser Ser Leu Ser Leu Tyr Thr Gly Ala Ile Leu Glu
625                 630                 635                 640 gcc aac ctg ctg cca ccg ccg gag ccg aaa gag agc tgg cgt cgc att      1968
Ala Asn Leu Leu Pro Pro Pro Glu Pro Lys Glu Ser Trp Arg Arg Ile
                645                 650                 655 atg gat gaa ctg tca gtc atc tcc tgc gat gtc tac cgc ggc tac gta      2016
Met Asp Glu Leu Ser Val Ile Ser Cys Asp Val Tyr Arg Gly Tyr Val
            660                 665                 670 cgt gaa aac aaa gat ttt gtg cct tac ttc cgc tcc gct acg ccg gaa      2064
Arg Glu Asn Lys Asp Phe Val Pro Tyr Phe Arg Ser Ala Thr Pro Glu
        675                 680                 685 caa gaa ctg ggc aaa ctg ccg ttg ggt tca cgt ccg gcg aaa cgt cgc      2112
Gln Glu Leu Gly Lys Leu Pro Leu Gly Ser Arg Pro Ala Lys Arg Arg
    690                 695                 700 cca acc ggc ggc gtc gag tca cta cgc gcc att ccg tgg atc ttc gcc      2160
Pro Thr Gly Gly Val Glu Ser Leu Arg Ala Ile Pro Trp Ile Phe Ala
705                 710                 715                 720 tgg acg caa aac cgt ctg atg ctc ccc gcc tgg ctg ggt gca ggt acg      2208
Trp Thr Gln Asn Arg Leu Met Leu Pro Ala Trp Leu Gly Ala Gly Thr
                725                 730                 735 gcg ctg caa aaa gtg gtc gaa gac ggc aaa cag agc gag ctg gag gct      2256
Ala Leu Gln Lys Val Val Glu Asp Gly Lys Gln Ser Glu Leu Glu Ala
            740                 745                 750 atg tgc cgc gat tgg cca ttc ttc tcg acg cgt ctc ggc atg ctg gag      2304
Met Cys Arg Asp Trp Pro Phe Phe Ser Thr Arg Leu Gly Met Leu Glu
        755                 760                 765 atg gtc ttc gcc aaa gca gac ctg tgg ctg gcg gaa tac tat gac caa      2352
Met Val Phe Ala Lys Ala Asp Leu Trp Leu Ala Glu Tyr Tyr Asp Gln
    770                 775                 780 cgc ctg gta gac aaa gca ctg tgg ccg tta ggt aaa gag tta cgc aac      2400
Arg Leu Val Asp Lys Ala Leu Trp Pro Leu Gly Lys Glu Leu Arg Asn
785                 790                 795                 800 ctg caa gaa gaa gac atc aaa gtg gtg ctg gcg att gcc aac gat tcc      2448
Leu Gln Glu Glu Asp Ile Lys Val Val Leu Ala Ile Ala Asn Asp Ser
                805                 810                 815 cat ctg atg gcc gat ctg ccg tgg att gca gag tct att cag cta cgg      2496
His Leu Met Ala Asp Leu Pro Trp Ile Ala Glu Ser Ile Gln Leu Arg
            820                 825                 830 aat att tac acc gac ccg ctg aac gta ttg cag gcc gag ttg ctg cac      2544
Asn Ile Tyr Thr Asp Pro Leu Asn Val Leu Gln Ala Glu Leu Leu His
        835                 840                 845 cgc tcc cgc cag gca gaa aaa gaa ggc cag gaa ccg gat cct cgc gtc      2592
Arg Ser Arg Gln Ala Glu Lys Glu Gly Gln Glu Pro Asp Pro Arg Val
    850                 855                 860 gaa caa gcg tta atg gtc act att gcc ggg att gcg gca ggt atg cgt      2640
Glu Gln Ala Leu Met Val Thr Ile Ala Gly Ile Ala Ala Gly Met Arg
865                 870                 875                 880 aat acc ggc taa                                                       2652
Asn Thr Gly <210> SEQ ID NO 19
<211> LENGTH: 883
<212> TYPE: PRT
<213> ORGANISM: Escherichia coli
```

<400> SEQUENCE: 19

Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
    370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly

```
                405                 410                 415
Asp Tyr Glu Ser Trp Ser Glu Ala Asp Lys Gln Ala Phe Leu Ile Arg
                420                 425                 430

Glu Leu Asn Ser Lys Arg Pro Leu Leu Pro Arg Asn Trp Gln Pro Ser
                435                 440                 445

Ala Glu Thr Arg Glu Val Leu Asp Thr Cys Gln Val Ile Ala Glu Ala
            450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
                500                 505                 510

Asn Ala Asn Asp Val Met Thr Gln Leu Leu Asn Ile Asp Trp Tyr Arg
            515                 520                 525

Gly Leu Ile Gln Gly Lys Gln Met Val Met Ile Gly Tyr Ser Asp Ser
        530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
        595                 600                 605

Arg Val Thr Glu Gln Gly Glu Met Ile Arg Phe Lys Tyr Gly Leu Pro
    610                 615                 620

Glu Ile Thr Val Ser Ser Leu Ser Leu Tyr Thr Gly Ala Ile Leu Glu
625                 630                 635                 640

Ala Asn Leu Leu Pro Pro Pro Glu Pro Lys Glu Ser Trp Arg Arg Ile
                645                 650                 655

Met Asp Glu Leu Ser Val Ile Ser Cys Asp Val Tyr Arg Gly Tyr Val
            660                 665                 670

Arg Glu Asn Lys Asp Phe Val Pro Tyr Phe Arg Ser Ala Thr Pro Glu
        675                 680                 685

Gln Glu Leu Gly Lys Leu Pro Leu Gly Ser Arg Pro Ala Lys Arg Arg
    690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
        755                 760                 765

Met Val Phe Ala Lys Ala Asp Leu Trp Leu Ala Glu Tyr Tyr Asp Gln
    770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830
```

```
Asn Ile Tyr Thr Asp Pro Leu Asn Val Leu Gln Ala Glu Leu Leu His
            835                 840                 845
Arg Ser Arg Gln Ala Glu Lys Glu Gly Gln Glu Pro Asp Pro Arg Val
    850                 855                 860
Glu Gln Ala Leu Met Val Thr Ile Ala Gly Ile Ala Ala Gly Met Arg
865                 870                 875                 880
Asn Thr Gly

<210> SEQ ID NO 20
<211> LENGTH: 1284
<212> TYPE: DNA
<213> ORGANISM: Escherichia coli
<220> FEATURE:
<221> NAME/KEY: CDS
<222> LOCATION: (1)..(1284)
<223> OTHER INFORMATION: citrate synthase

<400> SEQUENCE: 20 atg gct gat aca aaa gca aaa ctc acc ctc aac ggg gat aca gct gtt        48
Met Ala Asp Thr Lys Ala Lys Leu Thr Leu Asn Gly Asp Thr Ala Val
1               5                   10                  15 gaa ctg gat gtg ctg aaa ggc acg ctg ggt caa gat gtt att gat atc        96
Glu Leu Asp Val Leu Lys Gly Thr Leu Gly Gln Asp Val Ile Asp Ile
            20                  25                  30 cgt act ctc ggt tca aaa ggt gtg ttc acc ttt gac cca ggc ttc act       144
Arg Thr Leu Gly Ser Lys Gly Val Phe Thr Phe Asp Pro Gly Phe Thr
        35                  40                  45 tca acc gca tcc tgc gaa tct aaa att act ttt att gat ggt gat gaa       192
Ser Thr Ala Ser Cys Glu Ser Lys Ile Thr Phe Ile Asp Gly Asp Glu
    50                  55                  60 ggt att ttg ctg cac cgc ggt ttc ccg atc gat cag ctg gcg acc gat       240
Gly Ile Leu Leu His Arg Gly Phe Pro Ile Asp Gln Leu Ala Thr Asp
65                  70                  75                  80 tct aac tac ctg gaa gtt tgt tac atc ctg ctg aat ggt gaa aaa ccg       288
Ser Asn Tyr Leu Glu Val Cys Tyr Ile Leu Leu Asn Gly Glu Lys Pro
                85                  90                  95 act cag gaa cag tat gac gaa ttt aaa act acg gtg acc cgt cat acc       336
Thr Gln Glu Gln Tyr Asp Glu Phe Lys Thr Thr Val Thr Arg His Thr
            100                 105                 110 atg atc cac gag cag att acc cgt ctg ttc cat gct ttc cgt cgc gac       384
Met Ile His Glu Gln Ile Thr Arg Leu Phe His Ala Phe Arg Arg Asp
        115                 120                 125 tcg cat cca atg gca gtc atg tgt ggt att acc ggc gcg ctg gcg gcg       432
Ser His Pro Met Ala Val Met Cys Gly Ile Thr Gly Ala Leu Ala Ala
    130                 135                 140 ttc tat cac gac tcg ctg gat gtt aac aat cct cgt cac cgt gaa att       480
Phe Tyr His Asp Ser Leu Asp Val Asn Asn Pro Arg His Arg Glu Ile
145                 150                 155                 160 gcc gcg ttc cgc ctg ctg tcg aaa atg ccg acc atg gcc gcg atg tgt       528
Ala Ala Phe Arg Leu Leu Ser Lys Met Pro Thr Met Ala Ala Met Cys
                165                 170                 175 tac aag tat tcc att ggt cag cca ttt gtt tac ccg cgc aac gat ctc       576
Tyr Lys Tyr Ser Ile Gly Gln Pro Phe Val Tyr Pro Arg Asn Asp Leu
            180                 185                 190 tcc tac gcc ggt aac ttc ctg aat atg atg ttc tcc acg ccg tgc gaa       624
Ser Tyr Ala Gly Asn Phe Leu Asn Met Met Phe Ser Thr Pro Cys Glu
        195                 200                 205 ccg tat gaa gtt aat ccg att ctg gaa cgt gct atg gac cgt att ctg       672
Pro Tyr Glu Val Asn Pro Ile Leu Glu Arg Ala Met Asp Arg Ile Leu
    210                 215                 220
```

```
atc ctg cac gct gac cat gaa cag aac gcc tct acc tcc acc gtg cgt        720
Ile Leu His Ala Asp His Glu Gln Asn Ala Ser Thr Ser Thr Val Arg
225                 230                 235                 240 acc gct ggc tct tcg ggt gcg aac ccg ttt gcc tgt atc gca gca ggt        768
Thr Ala Gly Ser Ser Gly Ala Asn Pro Phe Ala Cys Ile Ala Ala Gly
                245                 250                 255 att gct tca ctg tgg gga cct gcg cac ggc ggt gct aac gaa gcg gcg        816
Ile Ala Ser Leu Trp Gly Pro Ala His Gly Gly Ala Asn Glu Ala Ala
            260                 265                 270 ctg aaa atg ctg gaa gaa atc agc tcc gtt aaa cac att ccg gaa ttt        864
Leu Lys Met Leu Glu Glu Ile Ser Ser Val Lys His Ile Pro Glu Phe
        275                 280                 285 gtt cgt cgt gcg aaa gac aaa aat gat tct ttc cgc ctg atg ggc ttc        912
Val Arg Arg Ala Lys Asp Lys Asn Asp Ser Phe Arg Leu Met Gly Phe
    290                 295                 300 ggt cac cgc gtg tac aaa aat tac gac ccg cgc gcc acc gta atg cgt        960
Gly His Arg Val Tyr Lys Asn Tyr Asp Pro Arg Ala Thr Val Met Arg
305                 310                 315                 320 gaa acc tgc cat gaa gtg ctg aaa gag ctg ggc acg aag gat gac ctg       1008
Glu Thr Cys His Glu Val Leu Lys Glu Leu Gly Thr Lys Asp Asp Leu
                325                 330                 335 ctg gaa gtg gct atg gag ctg gaa aac atc gcg ctg aac gac ccg tac       1056
Leu Glu Val Ala Met Glu Leu Glu Asn Ile Ala Leu Asn Asp Pro Tyr
            340                 345                 350 ttt atc gag aag aaa ctg tac ccg aac gtc gat ttc tac tct ggt atc       1104
Phe Ile Glu Lys Lys Leu Tyr Pro Asn Val Asp Phe Tyr Ser Gly Ile
        355                 360                 365 atc ctg aaa gcg atg ggt att ccg tct tcc atg ttc acc gtc att ttc       1152
Ile Leu Lys Ala Met Gly Ile Pro Ser Ser Met Phe Thr Val Ile Phe
    370                 375                 380 gca atg gca cgt acc gtt ggc tgg atc gcc cac tgg agc gaa atg cac       1200
Ala Met Ala Arg Thr Val Gly Trp Ile Ala His Trp Ser Glu Met His
385                 390                 395                 400 agt gac ggt atg aag att gcc cgt ccg cgt cag ctg tat aca gga tat       1248
Ser Asp Gly Met Lys Ile Ala Arg Pro Arg Gln Leu Tyr Thr Gly Tyr
                405                 410                 415 gaa aaa cgc gac ttt aaa agc gat atc aag cgt taa                       1284
Glu Lys Arg Asp Phe Lys Ser Asp Ile Lys Arg
            420                 425

<210> SEQ ID NO 21
<211> LENGTH: 427
<212> TYPE: PRT
<213> ORGANISM: Escherichia coli

<400> SEQUENCE: 21

Met Ala Asp Thr Lys Ala Lys Leu Thr Leu Asn Gly Asp Thr Ala Val
1               5                   10                  15

Glu Leu Asp Val Leu Lys Gly Thr Leu Gly Gln Asp Val Ile Asp Ile
            20                  25                  30

Arg Thr Leu Gly Ser Lys Gly Val Phe Thr Phe Asp Pro Gly Phe Thr
        35                  40                  45

Ser Thr Ala Ser Cys Glu Ser Lys Ile Thr Phe Ile Asp Gly Asp Glu
    50                  55                  60

Gly Ile Leu Leu His Arg Gly Phe Pro Ile Asp Gln Leu Ala Thr Asp
65                  70                  75                  80

Ser Asn Tyr Leu Glu Val Cys Tyr Ile Leu Leu Asn Gly Glu Lys Pro
                85                  90                  95
```

Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
        115                 120                 125

Ser His Pro Met Ala Val Met Cys Gly Ile Thr Gly Ala Leu Ala Ala
    130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Asn Met Met Phe Ser Thr Pro Cys Glu
        195                 200                 205

Pro Tyr Glu Val Asn Pro Ile Leu Glu Arg Ala Met Asp Arg Ile Leu
    210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
            260                 265                 270

Leu Lys Met Leu Glu Glu Ile Ser Ser Val Lys His Ile Pro Glu Phe
        275                 280                 285

Val Arg Arg Ala Lys Asp Lys Asn Asp Ser Phe Arg Leu Met Gly Phe
    290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
        355                 360                 365

Ile Leu Lys Ala Met Gly Ile Pro Ser Ser Met Phe Thr Val Ile Phe
    370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
            420                 425

<210> SEQ ID NO 22
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 22
gtgagcggat aacaattgac at                                    22

<210> SEQ ID NO 23
<211> LENGTH: 34
<212> TYPE: DNA

<213> ORGANISM: Artificial Sequence
<220> FEATURE:
<223> OTHER INFORMATION: Synthetic oligonucleotide

<400> SEQUENCE: 23
tgtccggtta atccccact gggtattgaa tttg                          34

<210> SEQ ID NO 24
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 24
tgtccggtta atccccact gggtattgaa tttggtccgg gtc                43

<210> SEQ ID NO 25
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 25
agagggccag gaccaggacc tggacccgga ccaaattcaa ta                42

<210> SEQ ID NO 26
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 26
cctggtcctg gccctctaga agtgttgttc caaggtcc                     38

<210> SEQ ID NO 27
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 27
tagcacgagt ttcgcacgac caggaccttg gaacaacact t                 41

<210> SEQ ID NO 28
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 28
cgtgcgaaac tcgtgctaga agaataccgt aagcacgtag c                 41

<210> SEQ ID NO 29
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 29
gcttatcgat accgtcgact taaaccgcag tctggaaaat ca                42

<210> SEQ ID NO 30
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 30
ggaattcgat atcaagctta tcgataccgt cgactta                              37

<210> SEQ ID NO 31
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 31
catgagtttc gcacgaccag gaccttggaa caacactt                             38

<210> SEQ ID NO 32
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 32
ggtcgtgcga aactcatgtc gtcaaccctc cgagaagcca                           40

<210> SEQ ID NO 33
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 33
cttatcgata ccgtcgactt acttcaacat attacgaatg acat                      44

<210> SEQ ID NO 34
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 34
acaccaccgg cccgatgacc cgtgatcagc tgaaaga                              37

<210> SEQ ID NO 35
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 35
aggcacgcca ggtctttcag ctgatcacgg gtcat                                35

<210> SEQ ID NO 36
<211> LENGTH: 23
<212> TYPE: DNA
<213> ORGANISM: Artificial Sequence
<220> FEATURE:

<223> OTHER INFORMATION: Synthetic oligonucleotide

<400> SEQUENCE: 36
acgggtcatc gggccggtgg tgt                                           23

<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 37
aaagacctgg cgtgcctggg ctt                                           23

<210> SEQ ID NO 38
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 38
ggtcccaaaa ttacctcgac caaccaca                                      28

<210> SEQ ID NO 39
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 39
gtaaacatga caaaactgtc gatcacaatc aa                                 32

<210> SEQ ID NO 40
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 40
ggtcgtgcga aactcatgct ggctagtcgt gtttcaatca aag                     43

<210> SEQ ID NO 41
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 41
aggctacgtg caaggcgtgg agctttgatt gaaacacgac ta                      42

<210> SEQ ID NO 42
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 42
acgccttgca cgtagccttg cgactaccac taatgcctcc ctc                     43

```
<210> SEQ ID NO 43
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 43
tgggcgaagc ttatacacaa aacacttatt tcttggaggc ag                              42
```

US 9,328,362 B2

RECOMBINANT ENZYME SYSTEMS FOR EFFICIENT PRODUCTION OF ITACONATE IN CELLS

CROSS REFERENCE TO RELATED APPLICATION

This application claims priority to U.S. Provisional Application No. 61/955,468, filed on Mar. 19, 2014, the content of which is incorporated herein by reference in its entirety.

BACKGROUND

Itaconate, in high demand in the chemical industry, is a precursor compound commonly used in the manufacture of various products, such as acrylic fibers, rubbers, artificial diamonds, and lenses. Certain filamentous fungi (e.g., *Ustilago*, *Helicobasidium*, and *Aspergillus*) convert monosaccharides to this compound. Currently, industrial production of itaconate relies mainly on the fermentation of native itaconate—producing microorganisms such as *Aspergillus terreus*. *Aspergillus terreus* grows slowly and does not produce itaconate in its spore-forming stage. There is a need for a method that produces itaconate in high yield.

SUMMARY

In one aspect, described herein is a fusion polypeptide that contains an aconitase (Aco) and a cis-aconitate decarboxylase (CAD), wherein the polypeptide exhibits an Aco activity and a CAD activity. The fusion polypeptide can further include a linker between the Aco and the CAD. In one embodiment, the CAD is in the N-terminal portion of the polypeptide.

In the fusion polypeptide, the Aco can be a eukaryotic Aco, e.g., a yeast Aco. In one embodiment, the Aco is an *E. coli* AcnA or *E. coli* AcnB. The AcnB can be the AcnB E424Q mutant. In one embodiment, the CAD is the CAD V490GI mutant. The fusion polypeptide can have the amino acid sequence of SEQ ID NO: 9, 11, 13, or 15.

Also described herein is a nucleic acid molecule that contains a nucleic acid sequence encoding any of the fusion polypeptides described herein. An expression vector, containing a nucleic acid sequence encoding any of the fusion polypeptides and a promoter operably linked to the nucleic acid sequence, is also described herein.

In another aspect, a genetically modified cell is described. The cell contains a nucleic acid sequence encoding any of the fusion polypeptides described herein (e.g., a fusion polypeptide containing the amino acid sequence of SEQ ID NO: 9, 11, 13, or 15) and a promoter operably linked to the nucleic acid sequence. The genetically modified cell can be an *E. coli* cell and the promoter can be an inducible or constitutive promoter that is functional in the *E. coli* cell. The genetically modified cell can also be any eukaryotic cell and the promoter can be an inducible or constitutive promoter that is functional in the eukaryotic cell. In one embodiment, the promoter is the $P_{CP25}$ promoter.

In an embodiment, the cell further contains a nucleic acid encoding another AcnA polypeptide and a nucleic acid encoding another AcnB polypeptide. In one embodiment, the cell further contains a nucleic acid encoding an *A. terreus* CAD.

In one embodiment, the genetically modified cell also lacks a functional isocitrate dehydrogenase or expresses a lower level of isocitrate dehydrogenase. The cell can also further include a ppc gene and a gltA gene.

Also described herein is a method of producing itaconate. The method includes culturing any of the genetically modified cells described herein in a medium under conditions suitable for producing itaconate, whereby the cell produces itaconate. The method can further include a step of isolating the itaconate.

Another method of producing itaconate is also described. The method includes producing a genetically modified cell that expresses any of the fusion polypeptides described herein, culturing the cell under conditions that allow expression of the fusion polypeptide and production of itaconate, whereby the cell expresses the polypeptide and produces itaconate.

The details of one or more embodiments are set forth in the accompanying drawing and the description below. Other features, objects, and advantages of the embodiments will be apparent from the description and drawing, and from the claims.

DETAILED DESCRIPTION

Figure 1:
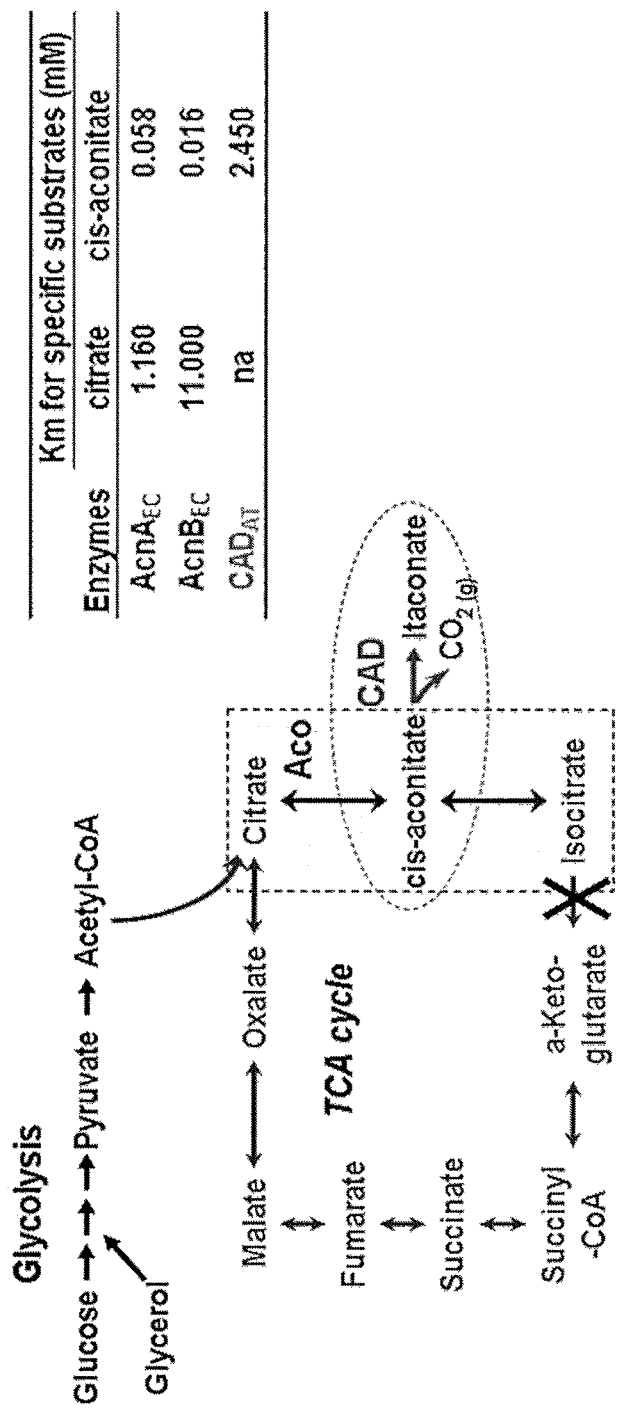
FIG. 1 includes a schematic representation (A) of the reactions catalyzed by aconitase (Aco) and cis-aconitate decarboxylase (CAD) and a table (B) showing the Km values of AcnA, AcnB (from *E. coli*) and CAD (from *A. terreus*) for citrate and cis-aconitate.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Biosynthesis of itaconate, in either eukaryotic or prokaryotic hosts, requires two enzymes, aconitase (Aco) and cis-aconitate decarboxylase (CAD), for two sequential reactions that convert citrate to itaconate. Citrate is first converted to cis-aconitate by Aco. The resulting cis-aconitate is further converted to itaconate by CAD, along with the release of one molecule of $CO_2$. See FIG. 1. The terms "itaconate" and "itaconic acid" are used interchangeably herein.

It was unexpectedly found that a cell expressing a fusion polypeptide containing an Aco and a CAD produces a high level of itaconate.

Accordingly, described herein is a fusion polypeptide including an Aco and a CAD.

The term "cis-aconitateic acid decarboxylase" or "CAD" refers to any naturally occurring CADs (e.g., the *A. terreus* CAD described in Dwiarti et al., J. Bioscience and Bioengineering, 94 (1):29-33, 2002 and WO 2009/014437) and functional equivalents thereof. For example, CADs include the mutant *A. terreus* CADs described in U.S. Pat. No. 8,338,158. Provided below are the nucleotide sequence (SEQ ID NO:1) and amino acid sequence (SEQ ID NO:2) of an exemplary *A. terreus* CAD:

```
atgaccaagcagtctgctgattccaacgcgaagtctggtgtgacctctgagatctgtcac
 M   T   K   Q   S   A   D   S   N   A   K   S   G   V   T   S   E   I   C   H tgggcgtctaatctcgccactgatgatatcccgagcgacgttctggagcgtgcaaaatac
 W   A   S   N   L   A   T   D   D   I   P   S   D   V   L   E   R   A   K   Y ctgatcctggatggtatcgcgtgcgcgtgggtaggtgctcgtgtcccatggtctgaaaaa
 L   I   L   D   G   I   A   C   A   W   V   G   A   R   V   P   W   S   E   K tacgttcaagcgaccatgtctttcgaacctccgggtgcgtgtcgtgtcatcggttacggc
 Y   V   Q   A   T   M   S   F   E   P   P   G   A   C   R   V   I   G   Y   G cagaaactgggtccggtagcggctgccatgacgaactctgcatttattcaggcgaccgaa
 Q   K   L   G   P   V   A   A   A   M   T   N   S   A   F   I   Q   A   T   E ctcgatgactatcactctgaagcgccgctgcattccgcgtctatcgttctcccggcagtt
 L   D   D   Y   H   S   E   A   P   L   H   S   A   S   I   V   L   P   A   V ttcgcggcgagcgaagtactggccgaacagggtaaaaccatctctggtattgacgtgatt
 F   A   A   S   E   V   L   A   E   Q   G   K   T   I   S   G   I   D   V   I ctggctgcgatcgttggtttcgagagcggtcctcgcatcggcaaagcgatctacggttct
 L   A   A   I   V   G   F   E   S   G   P   R   I   G   K   A   I   Y   G   S gacctcctgaacaacggctggcactgcggtgcggtatatggcgcaccggctggtgcgctc
 D   L   L   N   N   G   W   H   C   G   A   V   Y   G   A   P   A   G   A   L gcaactggtaagctcctgggcctcacgccggacagcatggaagatgcactgggtattgcc
 A   T   G   K   L   L   G   L   T   P   D   S   M   E   D   A   L   G   I   A tgcacgcaagcatgcggcctcatgtccgcgcagtatggtggcatggttaaacgtgttcag
 C   T   Q   A   C   G   L   M   S   A   Q   Y   G   G   M   V   K   R   V   Q cacggtttcgcagcgcgtaatggtctcctcggtggcctcctggctcacggcggctacgag
 H   G   F   A   A   R   N   G   L   L   G   G   L   L   A   H   G   G   Y   E gcgatgaaaggtgttctcgagcgttcttacggtggcttcctgaagatgttcaccaagggc
 A   M   K   G   V   L   E   R   S   Y   G   G   F   L   K   M   F   T   K   G aacggtcgtgaaccgccgtacaaagaagaagaggttgtggctggtctgggtagcttctgg
 N   G   R   E   P   P   Y   K   E   E   E   V   V   A   G   L   G   S   F   W cacaccttcaccattcgtatcaaactgtacgcgtgctgcggtctcgtacacggtcctgtt
 H   T   F   T   I   R   I   K   L   Y   A   C   C   G   L   V   H   G   P   V gaagccattgaaaacctccagggtcgttacccggaactgctcaatcgtgctaacctgtct
 E   A   I   E   N   L   Q   G   R   Y   P   E   L   L   N   R   A   N   L   S aacatccgccacgttcacgtacaactctctaccgcgagcaactcccactgtggttggatc
 N   I   R   H   V   H   V   Q   L   S   T   A   S   N   S   H   C   G   W   I ccagaagagcgcccaatctcttctatcgcgggtcaaatgtctgtcgcatatatcctcgcc
 P   E   E   R   P   I   S   S   I   A   G   Q   M   S   V   A   Y   I   L   A gttcagctcgttgaccaacagtgtctgctcagccagttctccgagtttgacgataatctg
 V   Q   L   V   D   Q   Q   C   L   L   S   Q   F   S   E   F   D   D   N   L gaacgcccggaagtgtgggacctggcacgtaaggttaccagctctcaatctgaggagttc
 E   R   P   E   V   W   D   L   A   R   K   V   T   S   S   Q   S   E   E   F gaccaggacggtaactgtctctctgccggtcgcgtccgtattgagttcaacgacggctcc
 D   Q   D   G   N   C   L   S   A   G   R   V   R   I   E   F   N   D   G   S
```

```
                              -continued
tccatcaccgaatccgttgagaagccgctcggtgtaaaggaaccaatgccaaatgaacgc
  S  I  T  E  S  V  E  K  P  L  G  V  K  E  P  M  P  N  E  R atcctgcacaaataccgtaccctggcgggttctgtaacggacgaaagccgtgttaaggag
  I  L  H  K  Y  R  T  L  A  G  S  V  T  D  E  S  R  V  K  E atcgaggatctcgtgctcggcctggaccgtctgaccgatattagcccgctcctcgagctg
  I  E  D  L  V  L  G  L  D  R  L  T  D  I  S  P  L  L  E  L Ctgaattgtccggttaaatccccactggtttaa
  L  N  C  P  V  K  S  P  L  V  -
```

As used herein, the term "aconitase" or "Aco" refers to any naturally occurring aconitases and functional equivalents thereof, including but not limited to, naturally occurring *A. terreus* and *E. coli* aconitases and variants thereof. Provided below are nucleotide sequences and amino acid sequences of *E. coli* aconitase A (encoded by acnA gene) and aconitase B (encoded by acnB gene):

```
Nucleic acid sequence (SEQ ID NO: 3) and amino acid sequence
(SEQ ID NO: 4) of an E. coli aconitase A
atgtcgtcaaccctacgagaagccagtaaggacacgttgcaggccaaagataaaacttac
  M  S  S  T  L  R  E  A  S  K  D  T  L  Q  A  K  D  K  T  Y cactactacagcctgccgcttgctgctaaatcactgggcgatatcacccgtctacccaag
  H  Y  Y  S  L  P  L  A  A  K  S  A  G  D  I  T  R  L  P  K tcactcaaagttttgctcgaaaacctgctgcgctggcaggatggtaactcggttaccgaa
  S  L  K  V  L  L  E  N  L  L  R  W  Q  D  G  N  S  V  T  E gaggatatccacgcgctggcaggatggctgaaaaatgcccatgctgaccgtgaaattgcc
  E  D  I  H  A  L  A  G  W  L  K  N  A  H  A  D  R  E  I  A taccgcccggcaagggtgctgatgcaggactttaccggcgtacctgccgttgttgatctg
  Y  R  P  A  R  V  L  M  Q  D  F  T  G  V  P  A  V  V  D  L gcggcaatgcgcgaagcggttaaacgcctcggaggcgatactgcaaaggttaacccgctc
  A  A  M  R  E  A  V  K  R  L  G  G  D  T  A  K  V  N  P  L tcaccggtcgacctggtcattgaccactcggtgaccgtcgatcgttttggtgatgatgag
  S  P  V  D  L  V  I  D  H  S  V  T  V  D  R  F  G  D  D  E gcatttgaagaaaacgtacgcctggaaatggagcgcaaccacgaacgttatgtgttcctg
  A  F  E  E  N  V  R  L  E  M  E  R  N  H  E  R  Y  V  F  L aaatggggaaagcaagcgttcagtcggtttagcgtcgtgccgccaggcacaggcatttgc
  K  W  G  K  Q  A  F  S  R  F  S  V  V  P  P  G  T  G  I  C catcaggttaacctcgaatatctcggcaaagcagtgtggagtgaattgcaggacggtgaa
  H  Q  V  N  L  E  Y  L  G  K  A  V  W  S  E  L  Q  D  G  E tggattgcttatccggatacactcgttggtactgactcgcacaccaccatgatcaacggc
  W  I  A  Y  P  D  T  L  V  G  T  D  S  H  T  T  M  I  N  G cttggcgtgctgggtggggcgttggtgggatcgaagcagaagccgcaatgttaggccag
  L  G  V  L  G  W  G  V  G  G  I  E  A  E  A  A  M  L  G  Q ccggtttccatgcttatcccggatgtagtgggcttcaaacttaccggaaaattacgtgaa
  P  V  S  M  L  I  P  D  V  V  G  F  K  L  T  G  K  L  R  E ggtattaccgccacagacctggttctcactgttacccaaatgctgcgcaaacatggcgtg
  G  I  T  A  T  D  L  V  L  T  V  T  Q  M  L  R  K  H  G  V gtggggaaattcgtcgaattttatggtgatggtctggattcactaccgttggcggatcgc
  V  G  K  F  V  E  F  Y  G  D  G  L  D  S  L  P  L  A  D  R gccaccattgccaatatgtcgccagaatatggtgccacctgtggcttcttcccaatcgat
  A  T  I  A  N  M  S  P  E  Y  G  A  T  C  G  F  F  P  I  D gctgtaaccctcgattacatgcgtttaagcgggcgcagcgaagatcaggtcgagttggtc
  A  V  T  L  D  Y  M  R  L  S  G  R  S  E  D  Q  V  E  L  V gaaaaatatgccaaagcgcagggcatgtggcgtaacccgggcgatgaaccaatttttacc
  E  K  Y  A  K  A  Q  G  M  W  R  N  P  G  D  E  P  I  F  T agtacgttagaactggatatgaatgacgttgaagcgagcctggcagggcctaaacgccca
  S  T  L  E  L  D  M  N  D  V  E  A  S  L  A  G  P  K  R  P caggatcgcgttgcactgcccgatgtaccaaaagcatttgccgccagtaacgaactggaa
  Q  D  R  V  A  L  P  D  V  P  K  A  F  A  A  S  N  E  L  E
```

-continued

```
gtgaatgccacgcataaagatcgccagccggtcgattatgttatgaacggacatcagtat
 V  N  A  T  H  K  D  R  Q  P  V  D  Y  V  M  N  G  H  Q  Y cagttacctgatggcgctgtggtcattgctgcgataacctcgtgcaccaacacctctaac
 Q  L  P  D  G  A  V  V  I  A  A  I  T  S  C  T  N  T  S  N ccaagtgtgctgatggccgcaggcttgctggcgaaaaaagccgtaactctgggcctcaag
 P  S  V  L  M  A  A  G  L  L  A  K  K  A  V  T  L  G  L  K cggcaaccatgggtcaaagcgtcgctggcaccgggttcgaaagtcgtttctgattatctg
 R  Q  P  W  V  K  A  S  L  A  P  G  S  K  V  V  S  D  Y  L gcaaaagcgaaactgacaccgtatctcgacgaactggggtttaaccttgtgggatacggt
 A  K  A  K  L  T  P  Y  L  D  E  L  G  F  N  L  V  G  Y  G tgtaccacctgtattggtaactctgggccgctgcccgatcctatcgaaacggcaatcaaa
 C  T  T  C  I  G  N  S  G  P  L  P  D  P  I  E  T  A  I  K aaaagcgatttaaccgtcggtgcggtgctgtccggcaaccgtaactttgaaggccgtatc
 K  S  D  L  T  V  G  A  V  L  S  G  N  R  N  F  E  G  R  I catccgctggttaaaactaactggctggcctcgccgccgctggtggttgcctatgcgctg
 H  P  L  V  K  T  N  W  L  A  S  P  P  L  V  V  A  Y  A  L gcgggaaatatgaatatcaacctggcttctgagcctatcggccatgatcgcaaaggcgat
 A  G  N  M  N  I  N  L  A  S  E  P  I  G  H  D  R  K  G  D ccggtttatctgaaagatatctggccatcggcacaagaaattgcccgtgcggtagaacaa
 P  V  Y  L  K  D  I  W  P  S  A  Q  E  I  A  R  A  V  E  Q gtctccacagaaatgttccgcaaagagtacgcagaagtttttgaaggcacagcagagtgg
 V  S  T  E  M  F  R  K  E  Y  A  E  V  F  E  G  T  A  E  W aagggaattaacgtcacacgatccgatacctacggttggcaggaggactcaacctatatt
 K  G  I  N  V  T  R  S  D  T  Y  G  W  Q  E  D  S  T  Y  I cgcttatcgcctttctttgatgaaatgcaggcaacaccagcaccagtggaagatattcac
 R  L  S  P  F  F  D  E  M  Q  A  T  P  A  P  V  E  D  I  H ggtgcgcggatcctcgcaatgctgggggattcagtcaccactgaccatatctctccggcg
 G  A  R  I  L  A  M  L  G  D  S  V  T  T  D  H  I  S  P  A ggcagtattaagcccgacagcccagcgggtcgatatctacaaggtcggggtgttgagcga
 G  S  I  K  P  D  S  P  A  G  R  Y  L  Q  G  R  G  V  E  R aaagactttaactcctacggttcgcggcgtggtaaccatgaagtgatgatgcgcggcacc
 K  D  F  N  S  Y  G  S  R  R  G  N  H  E  V  M  M  R  G  T ttcgccaatattcgcatccgtaatgaaatggtgcctggcgttgaagggggatgacgcgg
 F  A  N  I  R  I  R  N  E  M  V  P  G  V  E  G  G  M  T  R catttacctgacagcgacgtagtctctatttatgatgctgcgatgcgctataagcaggag
 H  L  P  D  S  D  V  V  S  I  Y  D  A  A  M  R  Y  K  Q  E caaacgccgctggcggtgattgccgggaaagagtatggatcaggctccagtcgtgactgg
 Q  T  P  L  A  V  I  A  G  K  E  Y  G  S  G  S  S  R  D  W gcggcaaaaggtccgcgtctgcttggtattcgtgtggtgattgccgaatcgtttgaacga
 A  A  K  G  P  R  L  L  G  I  R  V  V  I  A  E  S  F  E  R attcaccgttcgaatttaattggcatgggcatcctgccgctggaatttccgcaaggcgta
 I  H  R  S  N  L  I  G  M  G  I  L  P  L  E  F  P  Q  G  V acgcgtaaaacgttagggctaaccggggaagagaagattgatattggcgatctgcaaaac
 T  R  K  T  L  G  L  T  G  E  E  K  I  D  I  G  D  L  Q  N ctacaacccggcgcgacggttccggtgacgcttacgcgcgcggatggtagccaggaagtc
 L  Q  P  G  A  T  V  P  V  T  L  T  R  A  D  G  S  Q  E  V gtaccctgccgttgtcgtatcgacaccgcgacggagttgacctactaccagaacgacggc
 V  P  C  R  C  R  I  D  T  A  T  E  L  T  Y  Y  Q  N  D  G attttgcattatgtcattcgtaatatgttgaagtaa
 I  L  H  Y  V  I  R  N  M  L  K  -
```

Nucleic acid sequence (SEQ ID NO: 5) and amino acid sequence (SEQ ID NO: 6) of an *E. coli* aconitase B

```
atgctagaagaataccgtaagcacgtagctgagcgtgccgctgaggggattgcgcccaaa
 M  L  E  E  Y  R  K  H  V  A  E  R  A  A  E  G  I  A  P  K
```

```
cccctggatgcaaaccaaatggccgcacttgtagagctgctgaaaaacccgcccgcgggc
 P  L  D  A  N  Q  M  A  A  L  V  E  L  L  K  N  P  P  A  G gaagaagaattcctgttagatctgttaaccaaccgtgttccccaggcgtcgatgaagcc
 E  E  E  F  L  L  D  L  L  T  N  R  V  P  P  G  V  D  E  A gcctatgtcaaagcaggcttcctggctgctatcgcgaaaggcgaagccaaatcccctctg
 A  Y  V  K  A  G  F  L  A  A  I  A  K  G  E  A  K  S  P  L ctgactccggaaaaagccatcgaactgctgggcaccatgcagggtggttacaacattcat
 L  T  P  E  K  A  I  E  L  L  G  T  M  Q  G  G  Y  N  I  H ccgctgatcgacgcgctggatgatgccaaactggcacctattgctgccaaagcactttct
 P  L  I  D  A  L  D  D  A  K  L  A  P  I  A  A  K  A  L  S cacacgctgctgatgttcgataacttctatgacgtagaagagaaagcgaaagcaggcaac
 H  T  L  L  M  F  D  N  F  Y  D  V  E  E  K  A  K  A  G  N gaatatgcgaagcaggttatgcagtcctgggcggatgccgaatggttcctgaatcgcccg
 E  Y  A  K  Q  V  M  Q  S  W  A  D  A  E  W  F  L  N  R  P gcgctggctgaaaaactgaccgttactgtcttcaaagtcactggcgaaactaacaccgat
 A  L  A  E  K  L  T  V  T  V  F  K  V  T  G  E  T  N  T  D gacctttctccggcaccggatgcgtggtcacgcccggatatcccactgcacgcgctggcg
 D  L  S  P  A  P  D  A  W  S  R  P  D  I  P  L  H  A  L  A atgctgaaaaacgcccgtgaaggtattgagccagaccagcctggtgttgttggtccgatc
 M  L  K  N  A  R  E  G  I  E  P  D  Q  P  G  V  V  G  P  I aagcaaatcgaagctctgcaacagaaaggtttcccgctggcgtacgtcggtgacgttgtg
 K  Q  I  E  A  L  Q  Q  K  G  F  P  L  A  Y  V  G  D  V  V ggtacgggttcttcgcgtaaatccgccactaactccgttctgtggtttatgggcgatgat
 G  T  G  S  S  R  K  S  A  T  N  S  V  L  W  F  M  G  D  D attccacatgtgccgaacaaacgcggcggtggtttgtgcctcggcggtaaaattgcaccc
 I  P  H  V  P  N  K  R  G  G  G  L  C  L  G  G  K  I  A  P atcttctttaacacgatggaagacgcgggtgcactgccaatcgaagtcgacgtctctaac
 I  F  F  N  T  M  E  D  A  G  A  L  P  I  E  V  D  V  S  N ctgaacatgggcgacgtgattgacgtttacccgtacaaaggtgaagtgcgtaaccacgaa
 L  N  M  G  D  V  I  D  V  Y  P  Y  K  G  E  V  R  N  H  E accggcgaactgctggcgaccttcgaactgaaaaccgacgtgctgattgatgaagtgcgt
 T  G  E  L  L  A  T  F  E  L  K  T  D  V  L  I  D  E  V  R gctggtggccgtattccgctgattatcgggcgtggcctgaccaccaaagcgcgtgaagca
 G  R  I  P  I  P  L  I  I  G  R  G  L  T  T  K  A  R  E  A cttggtctgccgcacagtgatgtgttccgtcaggcgaaagatgtcgctgagagcgatcgc
 L  G  L  P  H  S  D  V  F  R  Q  A  K  D  V  A  E  S  D  R ggcttctcgctggcgcaaaaaatggtaggccgtgcctgtggcgtgaaaggcattcgtccg
 G  F  S  L  A  Q  K  M  V  G  R  A  C  G  V  K  G  I  R  P ggcgcgtactgtgaaccgaaaatgacttctgtaggttcccaggacaccaccggcccgatg
 G  A  Y  C  E  P  K  M  T  S  V  G  S  Q  D  T  T  G  P  M acccgtgatgaactgaaagacctggcgtgcctgggcttctcggctgacctggtgatgcag
 T  R  D  E  L  K  D  L  A  C  L  G  F  S  A  D  L  V  M  Q tcttttctgccacaccgcgcgtatccgaagccagttgacgtgaacacgcaccacacgctg
 S  F  C  H  T  A  A  Y  P  K  P  V  D  V  N  T  H  H  T  L ccggacttcattatgaaccgtggcggtgtgtcgctgcgtccgggtgacggcgtcattcac
 P  D  F  I  M  N  R  G  G  V  S  L  R  P  G  D  G  V  I  H tcctggctgaaccgtatgctgctgccggataccgtcggtaccggtggtgactcccatacc
 S  W  L  N  R  M  L  L  P  D  T  V  G  T  G  G  D  S  H  T cgtttccccgatcggtatctctttcccggcgggttctggtctggtggcgtttgctgccgca
 R  P  I  G  I  S  P  F  P  A  G  S  G  L  V  A  F  A  A  A actggcgtaatgccgcttgatatgccggaatccgttctggtgcgcttcaaaggcaaaatg
 T  G  V  M  P  L  D  M  P  E  S  V  L  V  R  F  K  G  K  M cagccgggcatcacccctgcgcgatctggtacacgctattccgctgtatgcgatcaaacaa
 P  G  G  I  T  L  R  D  L  V  H  A  I  P  L  Y  A  I  K  Q
```

-continued

```
ggtctgctgaccgttgagaagaaaggcaagaaaaacatcttctctggccgcatcctggaa
 G  L  L  T  V  E  K  K  G  K  K  N  I  F  S  G  R  I  L  E attgaaggtctgccggatctgaaagttgagcaggcctttgagctaaccgatgcgtccgcc
 I  E  G  L  P  D  L  K  V  E  Q  A  F  E  L  T  D  A  S  A gagcgttctgccgctggttgtaccatcaagctgaacaaagaaccgatcatcgaatacctg
 E  R  S  A  A  G  C  T  I  K  L  N  K  E  P  I  I  E  Y  L aactctaacatcgtcctgctgaagtggatgatcgcggaaggttacggcgatcgtcgtacc
 N  S  N  I  V  L  L  K  W  M  I  A  E  G  Y  G  D  R  R  T ctggaacgtcgtattcagggcatggaaaaatggctggcgaatcctgagctgctggaagcc
 L  E  R  R  I  Q  G  M  E  K  W  L  A  N  P  E  L  L  E  A gatgcagatgcggaatacgcggcagtgatcgacatcgatctggcggatattaaagagcca
 D  A  D  A  E  Y  A  A  V  I  D  I  D  L  A  D  I  K  E  P atcctgtgtgctccgaacgaccggatgacgcgcgtccgctgtctgcggtacagggtgag
 I  L  C  A  P  N  D  P  D  D  A  R  P  L  S  A  V  Q  G  E aagatcgacgaagtgtttatcggttcctgcatgaccaacatcggtcacttccgtgctgcg
 K  I  D  E  F  I  G  G  S  C  M  T  N  I  G  H  F  R  A  A ggtaaactgctggatgcgcataaaggtcagttgccgacccgcctgtgggtggcaccgcca
 G  K  L  L  D  A  H  K  G  Q  L  P  T  R  L  W  V  A  P  P acccgtatggacgccgcacagttgaccgaagaaggctactacagcgtcttcggtaagagt
 T  R  M  D  A  A  Q  L  T  E  E  G  Y  Y  S  V  F  G  K  S ggtgcgcgtatcgagatccctggctgttccctgtgtatgggtaaccaggcgcgtgtggcg
 G  A  R  I  E  I  P  G  C  S  L  C  M  G  N  Q  A  R  V  A gacggtgcaacggtggtttccacctctacccgtaacttcccgaaccgtctgggtactggc
 D  G  A  T  V  V  S  T  S  T  R  N  F  P  N  R  L  G  T  G gcgaatgtcttcctggcttctgcggaactggcggctgttgcggcgctgattggcaaactg
 A  N  V  F  L  A  S  A  E  L  A  A  V  A  A  L  I  G  K  L ccgacgccggaagagtaccagacctacgtggcgcaggtagataaaacagccgttgatact
 P  T  P  E  E  Y  Q  T  Y  V  A  Q  V  D  K  T  A  V  D  T taccgttatctgaacttcaaccagctttctcagtacaccgagaaagccgatggggtgatt
 Y  R  Y  L  N  F  N  Q  L  S  Q  Y  T  E  K  A  D  G  V  I ttccagactgcggtttaa
 F  Q  T  A  V  -
```

The fusion polypeptide, for example, can have the CAD at the N-terminal end of the polypeptide. In one embodiment, the Aco and the CAD are linked by a linker having, for example, 1-200 amino acids. A linker can be EFGPGPGPG-PGPLEVLFQGPGRAKL (SEQ ID NO:7).

Shown below are the amino acid sequences of exemplary fusion polypeptides and the nucleic acid sequences encoding the polypeptides:

```
Nucleic acid sequence (SEQ ID NO: 8) and amino acid sequence
(SEQ ID NO: 9) of cad-linker-acnA
atgaccaagcagtctgctgattccaacgcgaagtctggtgtgacctctgagatctgtcac
 M  T  K  Q  S  A  D  S  N  A  K  S  G  V  T  S  E  I  C  H tgggcgtctaatctcgccactgatgatatcccgagcgacgttctggagcgtgcaaaatac
 W  A  S  N  L  A  T  D  D  I  P  S  D  V  L  E  R  A  K  Y Ctgatcctggatggtatcgcgtgcgcgtgggtaggtgctcgtgtcccatggtctgaaaaa
 L  I  L  D  G  I  A  C  A  W  V  G  A  R  V  P  W  S  E  K tacgttcaagcgaccatgtctttcgaacctccgggtgcgtgtcgtgtcatcggttacggc
 Y  V  Q  A  T  M  S  F  E  P  P  G  A  C  R  V  I  G  Y  G cagaaactgggtccggtagcggctgccatgacgaactctgcatttattcaggcgaccgaa
 Q  K  L  G  P  V  A  A  A  M  T  N  S  A  F  I  Q  A  T  E ctcgatgactatcactctgaagcgccgctgcattccgcgtctatcgttctcccggcagtt
 L  D  D  Y  H  S  E  A  P  L  H  S  A  S  I  V  L  P  A  V
```

-continued

```
ttcgcggcgagcgaagtactggccgaacagggtaaaaccatctctggtattgacgtgatt
 F  A  A  S  E  V  L  A  E  Q  G  K  T  I  S  G  I  D  V  I ctggctgcgatcgttggtttcgagagcggtcctcgcatcggcaaagcgatctacggttct
 L  A  A  I  V  G  F  E  S  G  P  R  I  G  K  A  I  Y  G  S gacctcctgaacaacggctggcactgcggtgcggtatatggcgcaccggctggtgcgctc
 D  L  L  N  N  G  W  H  C  G  A  V  Y  G  A  P  A  G  A  L gcaactggtaagctcctgggcctcacgccggacagcatggaagatgcactgggtattgcc
 A  T  G  K  L  L  G  L  T  P  D  S  M  E  D  A  L  G  I  A tgcacgcaagcatgcggcctcatgtccgcgcagtatggtggcatggttaaacgtgttcag
 C  T  Q  A  C  G  L  M  S  A  Q  Y  G  G  M  V  K  R  V  Q cacggtttcgcagcgcgtaatggtctcctcggtggcctcctggctcacggcggctacgag
 H  G  F  A  A  R  N  G  L  L  G  G  L  L  A  H  G  G  Y  E gcgatgaaaggtgttctcgagcgttcttacggtggcttcctgaagatgttcaccaagggc
 A  M  K  G  V  L  E  R  S  Y  G  G  F  L  K  M  F  T  K  G aacggtcgtgaaccgccgtacaaagaagaagaggttgtggctggtctgggtagcttctgg
 N  G  R  E  P  P  Y  K  E  E  E  V  V  A  G  L  G  S  F  W cacaccttcaccattcgtatcaaactgtacgcgtgctgcggtctcgtacacggtcctgtt
 H  T  F  T  I  R  I  K  L  Y  A  C  C  G  L  V  H  G  P  V gaagccattgaaaacctccagggtcgttacccggaactgctcaatcgtgctaacctgtct
 E  A  I  E  N  L  Q  G  R  Y  P  E  L  L  N  R  A  N  L  S aacatccgccacgttcacgtacaactctctaccgcgagcaactcccactgtggttggatc
 N  I  R  H  V  H  V  Q  L  S  T  A  S  N  S  H  C  G  W  I ccagaagagcgcccaatctcttctatcgcgggtcaaatgtctgtcgcatatatcctcgcc
 P  E  E  R  P  I  S  S  I  A  G  Q  M  S  V  A  Y  I  L  A gttcagctcgttgaccaacagtgtctgctcagccagttctccgagtttgacgataatctg
 V  Q  L  V  D  Q  Q  C  L  L  S  Q  F  S  E  F  D  D  N  L gaacgcccggaagtgtgggacctggcacgtaaggttaccagctctcaatctgaggagttc
 E  R  P  E  V  W  D  L  A  R  K  V  T  S  S  Q  S  E  E  F gaccaggacggtaactgtctctctgccggtcgcgtccgtattgagttcaacgacggctcc
 D  Q  D  G  N  C  L  S  A  G  R  V  R  I  E  F  N  D  G  S tccatcaccgaatccgttgagaagccgctcggtgtaaaggaaccaatgccaaatgaacgc
 S  I  T  E  S  V  E  K  P  L  G  V  K  E  P  M  P  N  E  R atcctgcacaaataccgtaccctggcgggttctgtaacggacgaaagccgtgttaaggag
 I  L  H  K  Y  R  L  A  G  S  S  V  T  D  E  S  R  V  K  E atcgaggatctcgtgctcggcctggaccgtctgaccgatattagcccgctcctcgagctg
 I  E  D  L  V  L  G  L  D  R  L  T  D  I  S  P  L  L  E  L ctgaattgtccggttaaatccccactgggtattgaatttggtccgggtccaggtcctggt
 L  N  C  P  V  K  S  P  L  G  I  E  F  G  P  G  P  G  P  G cctggccctctagaagtgttgttccaaggtcctggtcgtgcgaaactcatgtcgtcaacc
 P  G  P  L  E  V  L  F  Q  G  P  G  R  A  K  L  M  S  S  T ctacgagaagccagtaaggacacgttgcaggccaaagataaaacttaccactactacagc
 L  R  E  A  S  K  D  T  L  Q  A  K  D  K  T  Y  H  Y  Y  S ctgccgcttgctgctaaatcactgggcgatatcacccgtctacccaagtcactcaaagtt
 L  P  L  A  A  K  S  L  G  D  I  T  R  L  P  K  S  L  K  V ttgctcgaaaacctgctgcgctggcaggatggtaactcggttaccgaagaggatatccac
 L  L  E  N  L  L  R  W  Q  D  G  N  S  V  T  E  E  D  I  H gcgctggcaggatggctgaaaaatgcccatgctgaccgtgaaattgcctaccgccggca
 A  L  A  G  W  L  K  N  A  H  A  D  R  E  I  A  Y  R  P  A agggtgctgatgcaggactttaccggcgtacctgccgttgttgatctggcggcaatgcgc
 R  V  L  M  Q  D  F  T  G  V  P  A  V  V  D  L  A  A  M  R gaagcggttaaacgcctcggcggcgatactgcaaaggttaacccgctctcaccggtcgac
 E  A  V  K  R  L  G  G  D  T  A  K  V  N  P  L  S  P  V  D ctggtcattgaccactcggtgaccgtcgatcgttttggtgatgatgaggcatttgaagaa
 L  V  I  D  H  S  V  T  V  D  R  E  G  D  D  E  A  F  E  E
```

```
-continued
aacgtacgcctggaaatggagcgcaaccacgaacgttatgtgttcctgaaatggggaaag
 N  V  R  L  E  M  E  R  N  H  E  R  Y  V  F  L  K  W  G  K caagcgttcagtcggtttagcgtcgtgccgccaggcacaggcatttgccatcaggttaac
 Q  A  F  S  R  F  S  V  V  P  P  G  T  G  I  C  H  Q  V  N ctcgaatatctcggcaaagcagtgtggagtgaattgcaggacggtgaatggattgcttat
 L  E  Y  L  G  K  A  V  W  S  E  L  Q  D  G  E  W  I  A  Y ccggatacactcgttggtactgactcgcacaccaccatgatcaacggccttggcgtgctg
 P  D  T  L  V  G  T  D  S  H  T  T  M  I  N  G  L  G  V  L gggtggggcgttggtgggatcgaagcagaagccgcaatgttaggccagccggtttccatg
 G  W  G  V  G  G  I  E  A  E  A  A  M  L  G  Q  P  V  S  M cttatcccggatgtagtgggcttcaaacttaccggaaaattacgtgaaggtattaccgcc
 L  I  P  D  V  V  G  F  K  L  T  G  K  L  R  E  G  I  T  A acagacctggttctcactgttacccaaatgctgcgcaaacatggcgtggtggggaaattc
 T  D  L  V  L  T  V  T  Q  M  L  R  K  H  G  V  V  G  K  F gtcgaattttatggtgatggtctggattcactaccgttggcggatcgcgccaccattgcc
 V  E  F  Y  G  D  G  L  D  S  L  L  A  D  D  R  A  T  I  A aatatgtcgccagaatatggtgccacctgtggcttcttcccaatcgatgctgtaaccctc
 N  M  S  P  E  Y  G  A  T  C  G  F  F  P  I  D  A  V  T  L gattacatgcgtttaagcgggcgcagcgaagatcaggtcgagttggtcgaaaaatatgcc
 D  Y  M  R  L  S  G  R  S  E  D  Q  V  E  L  V  E  K  Y  A aaagcgcagggcatgtggcgtaacccgggcgatgaaccaattttttaccagtacgttagaa
 K  A  Q  G  M  W  R  N  P  G  D  E  P  I  F  T  S  T  L  E ctggatatgaatgacgttgaagcgagcctggcagggcctaaacgcccacaggatcgcgtt
 L  D  M  N  D  V  E  A  S  L  A  G  P  K  R  P  Q  D  R  V gcactgcccgatgtaccaaaagcatttgccgccagtaacgaactggaagtgaatgccacg
 A  L  P  D  V  P  K  A  F  A  A  S  N  E  L  E  V  N  A  T cataaagatcgccagccggtcgattatgttatgaacggacatcagtatcagttacctgat
 H  K  D  R  Q  P  V  D  Y  V  M  N  G  H  Q  Y  Q  L  P  D ggcgctgtggtcattgctgcgataaccctcgtgcaccaacacctctaacccaagtgtgctg
 G  A  V  V  I  A  A  I  T  S  C  T  N  T  S  N  P  S  V  L atggccgcaggcttgctggcgaaaaaagccgtaactctgggcctcaagcggcaaccatgg
 M  A  A  G  L  L  A  K  K  A  V  T  L  G  L  K  R  Q  P  W gtcaaagcgtcgctggcaccgggttcgaaagtcgtttctgattatctggcaaaagcgaaa
 V  K  S  L  A  P  P  S  K  V  V  S  D  Y  L  A  K  A  K ctgacaccgtatctcgacgaactgggtttaaccttgtgggatacggttgtaccacctgt
 L  T  P  Y  L  D  E  L  G  F  N  L  V  G  Y  G  C  T  T  C attggtaactctgggccgctgcccgatcctatcgaaacggcaatcaaaaaaagcgattta
 I  G  N  S  G  P  L  P  D  P  I  E  T  A  I  K  K  S  D  L accgtcggtgcggtgctgtccggcaaccgtaactttgaaggccgtatccatccgctggtt
 T  V  G  A  V  L  S  G  N  R  N  F  E  G  R  I  H  P  L  V aaaactaactggctggcctcgccgccgctggtggttgcctatgcgctggcgggaaatatg
 K  T  N  W  L  A  S  P  P  L  V  V  A  Y  A  L  A  G  N  M aatatcaacctggcttctgagcctatcggccatgatcgcaaaggcgatccggtttatctg
 N  I  N  L  A  S  E  P  I  G  H  D  R  K  G  D  P  V  Y  L aaagatatctggccatcggcacaagaaattgcccgtgcggtagaacaagtctccacagaa
 K  D  I  W  P  S  A  Q  E  I  A  R  A  V  E  Q  V  S  T  E atgttccgcaaagagtacgcagaagtttttgaaggcacagcagagtggaagggaattaac
 M  F  R  K  E  Y  A  E  V  F  E  G  T  A  E  W  K  G  I  N gtcacacgatccgatacctacggttggcaggaggactcaacctatattcgcttatcgcct
 V  T  R  S  D  T  Y  G  W  Q  E  D  S  T  Y  I  R  L  S  P ttctttgatgaaatgcaggcaacaccagcaccagtggaagatattcacggtgcgcggatc
 F  F  D  E  M  Q  A  T  P  A  P  V  E  D  I  H  G  A  R  I ctcgcaatgctgggggattcagtcaccactgaccatatctctccggcgggcagtattaag
 L  A  M  L  G  D  S  V  T  T  D  H  I  S  P  A  G  S  I  K
```

```
-continued
cccgacagcccagcgggtcgatatctacaaggtcggggtgttgagcgaaaagactttaac
 P  D  S  P  A  G  R  Y  L  Q  G  R  G  V  E  R  K  D  F  N tcctacggttcgcggcgtggtaaccatgaagtgatgatgcgcggccttcgccaatatt
 S  Y  G  S  R  R  G  N  H  E  V  M  M  R  G  T  F  A  N  I cgcatccgtaatgaaatggtgcctggcgttgaaggggggatgacgcggcatttacctgac
 R  I  R  N  E  M  V  P  G  V  E  G  G  M  T  R  H  L  P  D agcgacgtagtctctatttatgatgctgcgatgcgctataagcaggagcaaacgccgctg
 S  D  V  V  S  I  Y  D  A  A  M  R  Y  K  Q  E  Q  T  P  L gcggtgattgccgggaaagagtatggatcaggctccagtcgtgactgggcggcaaaaggt
 A  V  I  A  G  K  E  Y  G  S  G  S  S  R  D  W  A  A  K  G ccgcgtctgcttggtattcgtgtggtgattgccgaatcgtttgaacgaattcaccgttcg
 P  R  L  L  G  I  R  V  V  I  A  E  S  F  E  R  I  H  R  S aatttaattggcatgggcatcctgccgctggaatttccgcaaggcgtaacgcgtaaaacg
 N  L  I  G  M  G  I  L  P  L  E  F  P  Q  G  V  T  R  K  T ttagggctaaccggggaagagaagattgatattggcgatctgcaaaacctacaacccggc
 L  G  L  T  G  E  E  K  I  D  I  G  D  L  Q  N  L  Q  P  G gcgacggttccggtgacgcttacgcgcgcggatggtagccaggaagtcgtaccctgccgt
 A  T  V  P  V  T  L  T  R  A  D  G  S  Q  E  V  V  P  C  R tgtcgtatcgacaccgcgacggagttgacctactaccagaacgacggcattttgcattat
 C  R  I  D  T  A  T  E  L  T  Y  Y  Q  N  D  G  I  L  H  Y g t c a t t c g t  a  at  g  t t g a  ag  t a a
  V    I    R       N     M     L     K
*

Nucleic acid sequence (SEQ ID NO: 10) and amino acid sequence
(SEQ ID NO: 11) of CAD-linker-acnB
atgaccaagcagtctgctgattccaacgcgaagtctggtgtgacctctgagatctgtcac
 M  T  K  S  A  D  D  S  N  A  K  S  G  V  T  S  E  I  C  H tgggcgtctaatctcgccactgatgatatcccgagcgacgttctggagcgtgcaaaatac
 W  A  S  N  L  A  T  D  D  I  P  S  D  V  L  E  R  A  K  Y Ctgatcctggatggtatcgcgtgcgcgtgggtaggtgctcgtgtcccatggtctgaaaaa
 L  I  L  D  G  I  A  C  A  W  V  G  A  R  V  P  W  S  E  K tacgttcaagcgaccatgtctttcgaacctccgggtgcgtgtcgtgtcatcggttacggc
 Y  V  Q  A  T  M  S  F  E  P  P  G  A  C  R  V  I  G  Y  G cagaaactgggtccggtagcggctgccatgacgaactctgcatttattcaggcgaccgaa
 Q  K  L  G  P  V  A  A  A  M  T  N  S  A  F  I  Q  A  T  E ctcgatgactatcactctgaagcgccgctgcattccgcgtctatcgttctcccggcagtt
 L  D  D  Y  H  S  E  A  P  L  H  S  A  S  I  V  L  P  A  V ttcgcggcgagcgaagtactggccgaacagggtaaaaccatctctggtattgacgtgatt
 F  A  A  S  E  V  L  A  E  Q  G  K  T  I  S  G  I  D  V  I ctggctgcgatcgttggtttcgagagcggtcctcgcatcggcaaagcgatctacggttct
 L  A  A  I  V  G  E  E  S  P  R  I  G  G  K  A  I  Y  G  S gacctcctgaacaacggctggcactgcggtgcggtatatggcgcaccggctggtgcgctc
 D  L  L  N  N  G  W  H  C  G  A  V  Y  G  A  P  A  G  A  L gcaactggtaagctcctgggcctcacgccggacagcatggaagatgcactgggtattgcc
 A  T  G  K  L  L  G  L  T  P  D  S  M  E  D  A  L  G  I  A tgcacgcaagcatgcggcctcatgtccgcgcagtatggtggcatggttaaacgtgttcag
 C  T  Q  A  C  G  L  M  S  A  Q  Y  G  G  M  V  K  R  V  Q cacggtttcgcagcgcgtaatggtctcctcggtggcctcctggctcacggcggctacgag
 H  G  F  A  A  R  N  G  L  L  G  G  L  L  A  H  G  G  Y  E gcgatgaaaggtgttctcgagcgttcttacggtggcttcctgaagatgttcaccaagggc
 A  M  K  G  V  L  E  R  S  Y  G  G  F  L  K  M  F  T  K  G aacggtcgtgaaccgccgtacaaagaagaagaggttgtggctggtctgggtagcttctgg
 N  G  R  E  P  P  Y  K  E  E  E  V  V  A  G  L  G  S  F  W cacaccttcaccattcgtatcaaactgtacgcgtgctgcggtctcgtacacggtcctgtt
 H  T  F  T  I  R  I  K  L  Y  A  C  C  G  L  V  H  G  P  V
```

-continued

```
gaagccattgaaaacctccagggtcgttacccggaactgctcaatcgtgctaacctgtct
 E  A  I  E  N  L  Q  G  R  Y  P  E  L  L  N  R  A  N  L  S aacatccgccacgttcacgtacaactctctaccgcgagcaactcccactgtggttggatc
 N  I  R  H  V  H  V  Q  L  S  T  A  S  N  S  H  C  G  W  I ccagaagagcgcccaatctcttctatcgcgggtcaaatgtctgtcgcatatatcctcgcc
 P  E  E  R  P  I  S  S  I  A  G  Q  M  S  V  A  Y  I  L  A gttcagctcgttgaccaacagtgtctgctcagccagttctccgagtttgacgataatctg
 V  Q  L  V  D  Q  Q  C  L  L  S  Q  F  S  E  F  D  D  N  L gaacgcccggaagtgtgggacctggcacgtaaggttaccagctctcaatctgaggagttc
 E  R  P  E  V  W  D  L  A  R  K  V  T  S  S  Q  S  E  E  F gaccaggacggtaactgtctctctgccggtcgcgtccgtattgagttcaacgacggctcc
 D  Q  D  G  N  C  L  S  A  G  R  V  R  I  E  F  N  D  G  S tccatcaccgaatccgttgagaagccgctcggtgtaaaggaaccaatgccaaatgaacgc
 S  I  T  E  S  V  E  K  P  L  G  V  K  E  P  M  P  N  E  R atcctgcacaaataccgtaccctggcgggttctgtaacggacgaaagccgtgttaaggag
 I  L  H  K  Y  R  T  L  A  G  S  V  T  D  E  S  R  V  K  E atcgaggatctcgtgctcggcctggaccgtctgaccgatattagcccgctcctcgagctg
 I  E  D  L  V  L  G  L  D  R  L  T  D  I  S  P  L  L  E  L ctgaattgtccggttaaatccccactgggtattgaatttggtccgggtccaggtcctggt
 L  N  C  P  V  K  S  P  I  G  I  E  F  G  P  G  P  G  P  G cctggccctctagaagtgttgttccaaggtcctggtcgtgcgaaactcgtgctagaagaa
.P  G  P  L  E  V  L  F  Q  G  P  G  R  A  K  L  V  L  E  E taccgtaagcacgtagctgagcgtgccgctgaggggattgcgcccaaacccctggatgca
 Y  R  K  H  V  A  E  R  A  A  E  G  I  A  P  K  P  L  D  A aaccaaatggccgcacttgtagagctgctgaaaaacccgcccgcgggcgaagaagaattc
 N  Q  M  A  A  L  V  E  L  L  K  N  P  P  A  G  E  E  E  F ctgttagatctgttaaccaaccgtgttcccccaggcgtcgatgaagccgcctatgtcaaa
 L  L  D  L  L  T  N  R  V  P  P  G  V  D  E  A  A  Y  V  K gcaggcttcctggctgctatcgcgaaaggcgaagccaaatcccctctgctgactccggaa
 A  G  F  L  A  A  I  A  K  G  E  A  K  S  P  L  L  T  P  E aaagccatcgaactgctgggcaccatgcagggtggttacaacattcatccgctgatcgac
 K  A  I  E  L  L  G  T  M  Q  G  G  Y  N  I  H  P  L  I  D gcgctggatgatgccaaactggcacctattgctgccaaagcactttctcacacgctgctg
 A  L  D  D  A  K  L  A  P  I  A  A  K  A  L  S  H  T  L  L atgttcgataacttctatgacgtagaagagaaagcgaaagcaggcaacgaatatgcgaag
 M  F  D  N  F  Y  D  V  E  E  K  A  K  A  G  N  E  Y  A  K caggttatgcagtcctgggcggatgccgaatggttcctgaatcgcccggcgctggctgaa
 Q  V  M  Q  S  W  A  D  A  E  W  F  L  N  R  P  A  L  A  E aaactgaccgttactgtcttcaaagtcactggcgaaactaacaccgatgacctttctccg
 K  L  T  V  T  V  F  K  V  T  G  E  T  N  T  D  D  L  S  P gcaccggatgcgtggtcacgcccggatatcccactgcacgcgctggcgatgctgaaaaac
 A  P  D  A  W  S  R  P  D  I  P  L  H  A  L  A  M  L  K  N gcccgtgaaggtattgagccagaccagcctggtgttgttggtccgatcaagcaaatcgaa
 A  R  E  G  I  E  P  D  Q  P  G  V  V  G  P  I  K  Q  I  E gctctgcaacagaaaggtttcccgctggcgtacgtcggtgacgttgtgggtacgggttct
 A  L  Q  Q  K  G  F  P  L  A  Y  V  G  D  V  V  G  T  G  S tcgcgtaaatccgccactaactccgttctgtggtttatgggcgatgatattccacatgtg
 S  R  K  S  A  T  N  S  V  L  W  F  M  G  D  D  I  P  H  V ccgaacaaacgcggcggtggtttgtgcctcggcggtaaaattgcacccatcttctttaac
 P  N  K  R  G  G  G  L  C  L  G  G  K  I  A  P  I  F  F  N acgatggaagacgcgggtgcactgccaatcgaagtcgacgtctctaacctgaacatgggc
 T  M  E  D  A  G  A  L  P  I  E  V  D  V  S  N  L  N  M  G gacgtgattgacgtttacccgtacaaaggtgaagtgcgtaaccacgaaaccggcgaactg
 D  V  I  D  V  Y  P  Y  K  G  E  V  R  N  H  E  T  G  E  L
```

-continued

```
ctggcgaccttcgaactgaaaaccgacgtgctgattgatgaagtgcgtgctggtggccgt
 L  A  T  F  E  L  K  T  D  V  L  I  D  E  V  R  A  G  G  R attccgctgattatcgggcgtggcctgaccaccaaagcgcgtgaagcacttggtctgccg
 I  P  L  I  I  G  R  G  L  T  T  K  A  R  E  A  L  G  L  P cacagtgatgtgttccgtcaggcgaaagatgtcgctgagagcgatcgcggcttctcgctg
 H  S  D  V  F  R  Q  A  K  D  V  A  E  S  D  R  G  F  S  L gcgcaaaaaatggtaggccgtgcctgtggcgtgaaaggcattcgtccgggcgcgtactgt
 A  Q  K  M  V  G  R  A  C  G  V  K  G  I  R  P  G  A  Y  C gaaccgaaaatgacttctgtaggttcccaggacaccaccggcccgatgacccgtgatgaa
 E  P  K  M  T  S  V  G  S  Q  D  T  T  G  P  M  T  R  D  E ctgaaagacctggcgtgcctgggcttctcggctgacctggtgatgcagtctttctgccac
 L  K  D  L  A  C  L  G  F  S  A  D  L  V  M  Q  S  F  C  H accgcggcgtatccgaagccagttgacgtgaacacgcaccacacgctgccggacttcatt
 T  A  A  Y  P  K  P  V  D  V  N  T  H  H  T  L  P  D  F  I atgaaccgtggcggtgtgtcgctgcgtccgggtgacggcgtcattcactcctggctgaac
 M  N  R  G  G  V  S  L  R  P  G  D  G  V  I  H  S  W  L  N cgtatgctgctgccggataccgtcggtaccggtggtgactcccataccgtttcccgatc
 R  M  L  L  P  D  T  V  G  T  G  G  D  S  H  T  R  F  P  I ggtatctctttcccggcgggttctggtctggtggcgtttgctgccgcaactggcgtaatg
 G  I  S  F  P  A  G  S  G  L  V  A  F  A  A  A  T  G  V  M ccgcttgatatgccggaatccgttctggtgcgcttcaaaggcaaaatgcagccgggcatc
 P  L  D  M  P  E  S  V  L  V  R  F  K  G  K  M  Q  P  G  I accctgcgcgatctggtacacgctattccgctgtatgcgatcaaacaaggtctgctgacc
 T  L  R  D  L  V  H  A  I  P  L  Y  A  I  K  Q  G  L  L  T gttgagaagaaaggcaagaaaaacatcttctctggccgcatcctggaaattgaaggtctg
 V  E  K  K  G  K  K  N  I  F  S  G  R  I  L  E  I  E  G  L ccggatctgaaagttgagcaggcctttgagctaaccgatgcgtccgccgagcgttctgcc
 P  D  L  K  V  E  Q  A  F  E  L  T  D  A  S  A  E  R  S  A gctggttgtaccatcaagctgaacaaagaaccgatcatcgaatacctgaactctaacatc
 A  G  C  T  I  K  L  N  K  E  P  I  I  E  Y  L  N  S  N  I gtcctgctgaagtggatgatcgcggaaggttacggcgatcgtcgtaccctggaacgtcgt
 V  L  L  K  W  M  I  A  E  G  Y  G  D  R  R  T  L  E  R  R attcagggcatggaaaaatggctggcgaatcctgagctgctggaagccgatgcagatgcg
 I  Q  G  M  E  K  W  L  A  N  P  E  L  L  E  A  D  A  D  A gaatacgcggcagtgatcgacatcgatctggcggatattaaagagccaatcctgtgtgct
 E  Y  A  A  V  I  D  I  D  L  A  D  I  K  E  P  I  L  C  A ccgaacgacccggatgacgcgcgtccgctgtctgcggtacagggtgagaagatcgacgaa
 P  N  D  P  D  D  A  R  P  L  S  A  V  Q  G  E  K  I  D  E gtgtttatcggttcctgcatgaccaacatcggtcacttccgtgctgcgggtaaactgctg
 F  I  G  G  S  C  M  T  N  I  G  H  F  R  A  A  G  K  L  L gatgcgcataaaggtcagttgccgacccgcctgtgggtggcaccgccaacccgtatggac
 D  A  H  K  G  Q  L  P  T  R  L  W  V  A  P  P  T  R  M  D gccgcacagttgaccgaagaaggctactacagcgtcttcggtaagagtggtgcgcgtatc
 A  A  Q  L  T  E  E  G  Y  Y  S  V  F  G  K  S  G  A  R  I gagatccctggctgttccctgtgtatgggtaaccaggcgcgtgtggcggacggtgcaacg
 E  I  P  G  C  S  L  C  M  G  N  Q  A  R  V  A  D  G  A  T gtggtttccacctctacccgtaacttcccgaaccgtctgggtactggcgcgaatgtcttc
 V  V  S  T  S  T  R  N  F  P  N  R  L  G  T  G  A  N  V  F ctggcttctgcggaactggcggctgttgcggcgctgattggcaaactgccgacgccggaa
 L  A  S  A  E  L  A  A  V  A  A  L  I  G  K  L  P  T  P  E gagtaccagacctacgtggcgcaggtagataaaacagccgttgatacttaccgttatctg
 E  Y  Q  T  Y  V  A  Q  V  D  K  T  A  V  D  T  Y  R  Y  L aacttcaaccagctttctcagtacaccgagaaagccgatggggtgattttccagactgcg
 N  F  N  Q  L  S  Q  Y  T  E  K  A  D  G  V  I  F  Q  T  A
```

```
gtttaa
 V  *
```

Nucleic acid sequence (SEQ ID NO: 12) and amino acid sequence (SEQ ID NO: 13) of CAD-linker-acnB E424Q

```
atgaccaagcagtctgctgattccaacgcgaagtctggtgtgacctctgagatctgtcac
 M  T  K  Q  S  A  D  S  N  A  K  S  G  V  T  S  E  I  C  H tgggcgtctaatctcgccactgatgatatcccgagcgacgttctggagcgtgcaaaatac
 W  A  S  N  L  A  T  D  D  I  P  S  D  V  L  E  R  A  K  Y Ctgatcctggatggtatcgcgtgcgcgtgggtaggtgctcgtgtcccatggtctgaaaaa
 L  I  L  D  G  I  A  C  A  W  V  G  A  R  V  P  W  S  E  K tacgttcaagcgaccatgtctttcgaacctccgggtgcgtgtcgtgtcatcggttacggc
 Y  V  Q  A  T  M  S  F  E  P  P  G  A  C  R  V  I  G  Y  G cagaaactgggtccggtagcggctgccatgacgaactctgcatLtattcaggcgaccgaa
 Q  K  L  G  P  V  A  A  A  M  T  N  S  A  F  I  Q  A  T  E ctcgatgactatcactctgaagcgccgctgcattccgcgtctatcgttctcccggcagtt
 L  D  D  Y  H  S  E  A  P  L  H  S  A  S  I  V  L  P  A  V ttcgcggcgagcgaagtactggccgaacagggtaaaaccatctctggtattgacgtgatt
 F  A  A  S  E  V  L  A  E  Q  G  K  T  I  S  G  I  D  V  I ctggctgcgatcgttggtttcgagagcggtcctcgcatcggcaaagcgatctacggttct
 L  A  A  I  V  G  F  E  S  P  R  I  G  G  K  A  I  Y  G  S gacctcctgaacaacggctggcactgcggtgcggtatatggcgcaccggctggtgcgctc
 D  L  L  N  N  G  W  H  C  G  A  V  Y  G  A  P  A  G  A  L gcaactggtaagctcctgggcctcacgccggacagcatggaagatgcactgggtattgcc
 A  T  G  K  L  L  G  L  T  P  D  S  M  E  D  A  L  G  I  A tgcacgcaagcatgcgggcctcatgtccgcgcagtatggtggcatggttaaacgtgttcag
 C  T  Q  A  C  G  L  M  S  A  Q  Y  G  G  M  V  K  R  V  Q cacggtttcgcagcgcgtaatggtctcctcggtggcctcctggctcacggcggctacgag
 H  G  F  A  A  R  N  G  L  L  G  G  L  L  A  H  G  G  Y  E gcgatgaaaggtgttctcgagcgttcttacggtggcttcctgaagatgttcaccaagggc
 A  M  K  G  V  L  E  R  S  Y  G  G  F  L  K  M  F  T  K  G aacggtcgtgaaccgccgtacaaagaagaagaggttgtggctggtctgggtagcttctgg
 N  G  R  E  P  P  Y  K  E  E  E  V  V  A  G  L  G  S  F  W cacaccttcaccattcgtatcaaactgtacgcgtgctgcggtctcgtacacggtcctgtt
 H  T  F  T  I  R  I  K  L  Y  A  C  C  G  L  V  H  G  P  V gaagccattgaaaacctccagggtcgttacccggaactgctcaatcgtgctaacctgtct
 E  A  I  E  N  L  Q  G  R  Y  P  E  L  L  N  R  A  N  L  S aacatccgccacgttcacgtacaactctctaccgcgagcaactcccactgtggttggatc
 N  I  R  H  V  H  V  Q  L  S  T  A  S  N  S  H  C  G  W  I ccagaagagcgcccaatctcttctatcgcgggtcaaatgtctgtcgcatatatcctcgcc
 P  E  E  R  P  I  S  S  I  A  G  Q  M  S  V  A  Y  I  L  A gttcagctcgttgaccaacagtgtctgctcagccagttctccgagtttgacgataatctg
 V  Q  L  V  D  Q  Q  C  L  L  S  Q  F  S  E  F  D  D  N  L gaacgcccggaagtgtgggacctggcacgtaaggttaccagctctcaatctgaggagttc
 E  R  P  E  V  W  D  L  A  R  K  V  T  S  S  Q  S  E  E  F gaccaggacggtaactgtctctctgccggtcgcgtccgtattgagttcaacgacggctcc
 D  Q  D  G  N  C  L  S  A  G  R  V  R  I  E  F  N  D  G  S tccatcaccgaatccgttgagaagccgctcggtgtaaaggaaccaatgccaaatgaacgc
 S  I  T  E  S  V  E  K  P  L  G  V  K  E  P  M  P  N  E  R atcctgcacaaataccgtaccctggcgggttctgtaacggacgaaagccgtgttaaggag
 I  L  H  K  Y  R  T  L  A  G  S  V  T  D  E  S  R  V  K  E atcgaggatctcgtgctcggcctggaccgtctgaccgatattagcccgctcctcgagctg
 I  E  D  L  V  L  G  L  D  R  L  T  D  I  S  P  L  L  E  L ctgaattgtccggttaaatccccactgggtattgaatttggtccgggtccaggtcctggt
 L  N  C  P  V  K  S  P  L  G  I  E  F  G  P  G  P  G  P  G
```

```
cctggccctctagaagtgttgttccaaggtcctggtcgtgcgaaactcgtgctagaagaa
 P  G  P  L  E  V  L  F  Q  G  P  G  R  A  K  L  V  L  E  E taccgtaagcacgtagctgagcgtgccgctgaggggattgcgcccaaaccctggatgca
 Y  R  K  H  V  A  E  R  A  A  E  G  I  A  P  K  P  L  D  A aaccaaatggccgcacttgtagagctgctgaaaaacccgcccgcgggcgaagaagaattc
 N  Q  M  A  A  L  V  E  L  L  K  N  P  P  A  G  E  E  E  F ctgttagatctgttaaccaaccgtgttccccaggcgtcgatgaagccgcctatgtcaaa
 L  L  D  L  L  T  N  R  V  P  P  G  V  D  E  A  A  Y  V  K gcaggcttcctggctgctatcgcgaaaggcgaagccaaatcccctctgctgactccggaa
 A  G  E  L  A  A  I  A  K  G  E  A  K  S  P  L  L  T  P  E aaagccatcgaactgctgggcaccatgcagggtggttacaacattcatccgctgatcgac
 K  A  I  E  L  L  G  T  M  Q  G  G  Y  N  I  H  P  L  I  D gcgctggatgatgccaaactggcacctattgctgccaaagcactttctcacacgctgctg
 A  L  D  D  A  K  L  A  P  I  A  A  K  A  L  S  H  T  L  L atgttcgataacttctatgacgtagaagagaaagcgaaagcaggcaacgaatatgcgaag
 M  F  D  N  F  Y  D  V  E  E  K  A  K  A  G  N  E  Y  A  K caggttatgcagtcctgggcggatgccgaatggttcctgaatcgcccggcgctggctgaa
 Q  V  M  Q  S  W  A  D  A  E  W  F  L  N  R  P  A  L  A  E aaactgaccgttactgtcttcaaagtcactggcgaaactaacaccgatgacctttctccg
 K  L  T  V  T  V  F  K  V  T  G  E  T  N  T  D  D  L  S  P gcaccggatgcgtggtcacgcccggatatcccactgcacgcgctggcgatgctgaaaaac
 A  P  D  A  W  S  R  P  D  I  P  L  H  A  L  A  M  L  K  N gcccgtgaaggtattgagccagaccagcctggtgttgttggtccgatcaagcaaatcgaa
 A  R  E  G  I  E  P  D  Q  P  G  V  V  G  P  I  K  Q  I  E gctctgcaacagaaaggtttcccgctggcgtacgtcggtgacgttgtgggtacgggttct
 A  L  Q  Q  K  G  F  P  L  A  Y  V  G  D  V  V  G  T  G  S tcgcgtaaatccgccactaactccgttctgtggtttatgggcgatgatattccacatgtg
 S  R  K  S  A  T  N  S  V  L  W  F  M  G  D  D  I  P  H  V ccgaacaaacgcggcggtggtttgtgcctcggcggtaaaattgcacccatcttctttaac
 P  N  K  R  G  G  G  L  C  L  G  G  K  I  A  P  I  F  F  N acgatggaagacgcgggtgcactgccaatcgaagtcgacgtctctaacctgaacatgggc
 T  M  E  D  A  G  A  L  P  I  E  V  D  V  S  N  L  N  M  G gacgtgattgacgtttacccgtacaaaggtgaagtgcgtaaccacgaaaccggcgaactg
 D  V  I  D  V  Y  P  Y  K  G  E  V  R  N  H  E  T  G  E  L ctggcgaccttcgaactgaaaaccgacgtgctgattgatgaagtgcgtgctggtggccgt
 L  A  T  F  E  L  K  T  D  V  L  I  D  E  V  R  A  G  G  R attccgctgattatcgggcgtggcctgaccaccaaagcgcgtgaagcacttggtctgccg
 I  P  L  I  I  G  R  G  L  T  T  K  A  R  E  A  L  G  L  P cacagtgatgtgttccgtcaggcgaaagatgtcgctgagagcgatcgcggcttctcgctg
 H  S  D  V  F  R  Q  A  K  D  V  A  E  S  D  R  G  F  S  L gcgcaaaaaatggtaggccgtgcctgtggcgtgaaaggcattcgtccgggcgcgtactgt
 A  Q  K  M  V  G  R  A  C  G  V  K  G  I  R  P  G  A  Y  C gaaccgaaaatgacttctgtaggttcccaggacaccaccggcccgatgacccgtgatcag
 E  P  K  M  T  S  V  G  S  Q  D  T  T  G  P  M  T  R  D  Q ctgaaagacctggcgtgcctgggcttctcggctgacctggtgatgcagtcttttctgccac
 L  K  D  L  A  C  L  G  F  S  A  D  L  V  M  Q  S  F  C  H accgcggcgtatccgaagccagttgacgtgaacacgcaccacacgctgccggacttcatt
 T  A  A  Y  P  K  P  V  D  V  N  T  H  H  T  L  P  D  F  I atgaaccgtggcggtgtgtcgctgcgtccgggtgacggcgtcattcactcctggctgaac
 M  N  R  G  G  V  S  L  R  P  G  D  G  V  I  H  S  W  L  N cgtatgctgctgccggataccgtcggtaccggtggtgactcccatacccgtttcccgatc
 R  M  L  L  P  D  T  V  G  T  G  G  D  S  H  T  R  F  P  I ggtatctcttttcccggcggggttctggtctggtggcgtttgctgccgcaactggcgtaatg
 G  I  S  F  P  A  G  S  G  L  V  A  F  A  A  A  T  G  V  M
```

-continued

```
ccgcttgatatgccggaatccgttctggtgcgcttcaaaggcaaaatgcagccgggcatc
 P  L  D  M  P  E  S  V  L  V  R  F  K  G  K  M  Q  P  G  I accctgcgcgatctggtacacgctattccgctgtatgcgatcaaacaaggtctgctgacc
 T  L  R  D  L  V  H  A  I  P  L  Y  A  I  K  Q  G  L  L  T gttgagaagaaaggcaagaaaaacatcttctctggccgcatcctggaaattgaaggtctg
 V  E  K  K  G  K  K  N  I  F  S  G  R  I  L  E  I  E  G  L ccggatctgaaagttgagcaggcctttgagctaaccgatgcgtccgccgagcgttctgcc
 P  D  L  K  V  E  Q  A  F  E  L  T  D  A  S  A  E  R  S  A gctggttgtaccatcaagctgaacaaagaaccgatcatcgaatacctgaactctaacatc
 A  G  C  T  I  K  L  N  K  E  P  I  I  E  Y  L  N  S  N  I gtcctgctgaagtggatgatcgcggaaggttacggcgatcgtcgtaccctggaacgtcgt
 V  L  L  K  W  M  I  A  E  G  Y  G  D  R  R  T  L  E  R  R attcagggcatggaaaaatggctggcgaatcctgagctgctggaagccgatgcagatgcg
 I  Q  G  M  E  K  W  L  A  N  P  E  L  L  E  A  D  A  D  A gaatacgcggcagtgatcgacatcgatctggcggatattaaagagccaatcctgtgtgct
 E  Y  A  A  V  I  D  I  D  L  A  D  I  K  E  P  I  L  C  A ccgaacgaccggatgacgcgcgtccgctgtctgggtacagggtgagaagatcgacgaa
 P  N  D  P  D  D  A  R  P  L  S  A  V  Q  G  E  K  I  D  E gtgtttatcggttcctgcatgaccaacatcggtcacttccgtgctgcgggtaaactgctg
 V  F  I  G  S  C  M  T  N  I  G  H  F  R  A  A  G  K  L  L gatgcgcataaaggtcagttgccgacccgcctgtgggtggcaccgccaacccgtatggac
 D  A  H  K  G  Q  L  P  T  R  L  W  V  A  P  P  T  R  M  D gccgcacagttgaccgaagaaggctactacagcgtcttcggtaagagtggtgcgcgtatc
 A  A  Q  L  T  E  E  G  Y  Y  S  V  F  G  K  S  G  A  R  I gagatccctggctgttccctgtgtatgggtaaccaggcgcgtgtggcggacggtgcaacg
 E  I  P  G  C  S  L  C  M  G  N  Q  A  R  V  A  D  G  A  T gtggtttccacctctacccgtaacttcccgaaccgtctgggtactggcgcgaatgtcttc
 V  V  S  T  S  T  R  N  F  P  N  R  L  G  T  G  A  N  V  F ctggcttctgcggaactggcggctgttgcggcgctgattggcaaactgccgacgccggaa
 L  A  S  A  E  L  A  A  V  A  A  L  I  G  K  L  P  T  P  E gagtaccagacctacgtggcgcaggtagataaaacagccgttgatacttaccgttatctg
 E  Y  Q  T  Y  V  A  Q  V  D  K  T  A  V  D  T  Y  R  Y  L aacttcaaccagctttctcagtacaccgagaaagccgatggggtgattttccagactgcg
 N  F  N  Q  L  S  Q  Y  T  E  K  A  D  V  I  E  F  Q  T  A gtttaa
 V  *
```

Nucleic acid sequence (SEQ ID NO: 14) and amino acid sequence
(SEQ ID NO: 15) of CAD-linker-Yaco1

```
atgaccaagcagtctgctgattccaacgcgaagtctggtgtgacctctgagatctgtcac
 M  T  K  Q  S  A  D  S  N  A  K  S  G  V  T  S  E  I  C  H tgggcgtctaatctcgccactgatgatatcccgagcgacgttctggagcgtgcaaaatac
 W  A  S  N  L  A  T  D  D  I  P  S  D  V  L  E  R  A  K  Y Ctgatcctggatggtatcgcgtgcgcgtgggtaggtgctcgtgtcccatggtctgaaaaa
 L  I  L  D  G  I  A  D  A  W  V  G  A  R  V  P  W  S  E  K tacgttcaagcgaccatgtctttcgaacctccgggtgcgtgtcgtgtcatcggttacggc
 Y  V  Q  A  T  M  S  F  E  P  P  G  A  C  R  V  I  G  Y  G cagaaactgggtccggtagcggctgccatgacgaactctgcatttattcaggcgaccgaa
 Q  K  L  G  P  V  A  A  A  M  T  N  S  A  F  I  Q  A  T  E ctcgatgactatcactctgaagcgccgctgcattccgcgtctatcgttctcccggcagtt
 L  D  D  Y  H  S  E  A  P  L  H  S  A  S  I  V  L  P  A  V ttcgcggcgagcgaagtactggccgaacagggtaaaaccatctctggtattgacgtgatt
 F  A  A  S  E  V  L  A  E  Q  G  K  T  I  S  G  I  D  V  I ctggctgcgatcgttggtttcgagagcggtcctcgcatcggcaaagcgatctacggttct
 L  A  A  I  V  G  F  E  S  P  R  I  G  G  K  A  I  Y  G  S
```

```
-continued
gacctcctgaacaacggctggcactgcggtgcggtatatggcgcaccggctggtgcgctc
 D   L   L   N   N   G   W   H   C   G   A   V   Y   G   A   P   A   G   A   L gcaactggtaagctcctgggcctcacgccggacagcatggaagatgcactgggtattgcc
 A   T   G   K   L   L   G   L   T   P   D   S   M   E   D   A   L   G   I   A tgcacgcaagcatgcggcctcatgtccgcgcagtatggtggcatggttaaacgtgttcag
 C   T   Q   A   C   G   L   M   S   A   Q   Y   G   G   M   V   K   R   V   Q cacggtttcgcagcgcgtaatggtctcctcggtggcctcctggctcacggcggctacgag
 H   G   F   A   A   R   N   G   L   L   G   G   L   L   A   H   G   G   Y   E gcgatgaaaggtgttctcgagcgttcttacggtggcttcctgaagatgttcaccaagggc
 A   M   K   G   V   L   E   R   S   Y   G   G   F   L   K   M   F   T   K   G aacggtcgtgaaccgccgtacaaagaagaagaggttgtggctggtctgggtagcttctgg
 N   G   R   E   P   P   Y   K   E   E   E   V   V   A   G   L   G   S   F   W cacaccttcaccattcgtatcaaactgtacgcgtgctgcggtctcgtacacggtcctgtt
 H   T   F   T   I   R   I   K   L   Y   A   C   C   G   L   V   H   G   P   V gaagccattgaaaacctccagggtcgttaccggaactgctcaatcgtgctaacctgtct
 E   A   I   E   N   L   Q   G   R   Y   P   E   L   L   N   R   A   N   L   S aacatccgccacgttcacgtacaactctctaccgcgagcaactcccactgtggttggatc
 N   I   R   H   V   H   V   Q   L   S   T   A   S   N   S   H   C   G   W   I ccagaagagcgcccaatctcttctatcgcgggtcaaatgtctgtcgcatatatcctcgcc
 P   E   E   R   P   I   S   S   I   A   G   Q   M   S   V   A   Y   I   L   A gttcagctcgttgaccaacagtgtctgctcagccagttctccgagtttgacgataatctg
 V   Q   L   V   D   Q   Q   C   L   L   S   Q   F   S   E   F   D   D   N   L gaacgcccggaagtgtgggacctggcacgtaaggttaccagctctcaatctgaggagttc
 E   R   P   E   V   W   D   L   A   R   K   V   T   S   S   Q   S   E   E   F gaccaggacggtaactgtctctctgccggtcgcgtccgtattgagttcaacgacggctcc
 D   Q   D   G   N   C   L   S   A   G   R   V   R   I   E   F   N   D   G   S tccatcaccgaatccgttgagaagccgctcggtgtaaaggaaccaatgccaaatgaacgc
 S   I   T   E   S   V   E   K   P   L   G   V   K   E   P   M   P   N   E   R atcctgcacaaataccgtaccctggcgggttctgtaacggacgaaagccgtgttaaggag
 I   L   H   K   Y   R   T   L   A   G   S   V   T   D   E   S   R   V   K   E atcgaggatctcgtgctcggcctggaccgtctgaccgatattagcccgctcctcgagctg
 I   E   D   L   V   L   G   L   D   R   L   T   D   I   S   P   L   L   E   L ctgaattgtccggttaaatccccactgggtattgaatttggtccgggtccaggtcctggt
 L   N   C   P   V   K   S   P   L   G   I   E   F   G   P   G   P   G   P   G cctggccctctagaagtgttgttccaaggtcctggtcgtgcgaaactcatgctggctagt
 .P   G   P   L   E   V   L   F   Q   G   P   G   R   A   K   L   M   L   A   S cgtgtttcaatcaaagctccacgccttgcacgtagccttgcgactaccactaatgcctcc
 R   V   S   I   K   A   P   R   L   A   R   S   L   A   T   T   T   N   A   S ctcaacttggactccaaggtccgaatgaacaactgggaggccaacaacttcctcaacttc
 L   N   L   D   S   K   V   R   M   N   N   W   E   A   N   N   F   L   N   F aagaagcacaccgagaacgtccagattgtcaaggagcgactcaaccgaccccctgacctac
 K   K   H   T   E   N   V   Q   I   V   K   E   R   L   N   R   P   L   T   Y gctgagaagattctctacggccatctcgacaagcccatgagcaggagattgtccgaggt
 A   E   K   I   L   Y   G   H   L   D   K   P   H   E   Q   E   I   V   R   G cagtcctacctcaagctgcgacccgatcgagccgcctgccaggatgccaccgcccagatg
 Q   S   Y   L   K   L   R   P   D   R   A   A   C   Q   D   A   T   A   Q   M gccattctgcagttcatgtctgccggtatccccaccgtccagacccccaccaccgtccac
 A   I   L   Q   F   M   S   A   G   I   P   T   V   Q   T   P   T   T   V   H tgtgaccatcttatccaggcccaggttggtggtgagcaggatcttgctcgagccatcgac
 C   D   H   L   I   Q   A   Q   V   G   G   E   Q   D   L   A   R   A   I   D atcaacaaggaggtctacaacttccttggcaccgcctccgccaagtacgacattggtttc
 I   N   K   E   V   Y   N   F   L   G   T   A   S   A   K   Y   D   I   G   F tggaaggccggatccggtattatccaccagatcattctcgagaactacgccttccccggt
 W   K   A   G   S   G   I   I   H   Q   I   I   L   E   N   Y   A   F   P   G
```

```
gcccttctcattggttccgactctcataccccaacgccggtggtctcggtatgctcgcc
 A  L  L  I  G  S  D  S  H  T  P  N  A  G  G  L  G  M  L  A atcggtgtcggtggtgccgatgtcgtcgacgtcatggccggtctcccctgggagcttaag
 I  G  V  G  G  A  D  V  V  D  V  M  A  G  L  P  W  E  L  K gcccccaagattatcggtgtcaagctgaccggtaagctctctggctggacctccoccaag
 A  P  K  I  I  G  V  K  L  T  G  K  L  S  G  W  T  S  P  K gatattatcctgaaggtcgctggtatcctcaccgtcaagggtggaaccggtgctatcgtc
 D  I  I  L  K  V  A  G  I  L  T  V  K  G  G  T  G  A  I  V gagtacttcggtgatggtgtcgataacctgtcctgcactggtatgggaaccatctgtaac
 E  Y  F  G  D  G  V  D  N  L  S  C  T  G  M  G  T  I  C  N atgggtgccgagattggtgctaccacctccaccttccccttcaacgagcgaatggccgac
 M  G  A  E  I  G  A  T  T  S  T  F  P  F  N  E  R  M  A  D taccttaacgccactggccgaaaggagattgccgactttgctcgactttacaaccacttc
 Y  L  N  A  T  G  R  K  E  I  A  D  F  A  R  L  Y  N  H  F ctctctgccgatgagggttgtgagtacgatcagctcatcgagattgacctgaacacccttt
 L  S  A  D  E  G  C  E  Y  D  Q  L  I  E  I  D  L  N  T  L gagccttacgtcaacggtcccttcactccgatcttgccaccccatctccaagctcaag
 E  P  Y  V  N  G  P  F  T  P  D  L  A  T  P  I  S  K  L  K gatgtcgccgtcgagaacggatggccccttgaggtcaaggtcggtcttatcggctcttgc
 D  V  A  V  E  N  G  W  P  L  E  V  K  V  G  L  I  G  S  C accaactcctcttacgaggatatggagcgatccgcctccattgccaaggacgccatggcc
 T  N  S  S  Y  E  D  M  E  R  S  A  S  I  A  K  D  A  M  A cacggtcttaagtccaagtccatctacaccgtcaccccggttccgagcagatccgagcc
 H  G  L  K  S  K  S  I  Y  T  V  T  P  G  S  E  Q  I  R  A accattgagcgagatggtcagctccagaccttcctcgacttcggtggtatcgtccttgct
 T  I  E  R  D  G  Q  L  Q  T  F  L  D  F  G  G  I  V  L  A aacgcttgtggcccctgcattggtcagtgggaccgacgagacatcaagaagggtgagaag
 N  A  C  G  P  C  I  G  Q  W  D  R  R  D  I  K  K  G  E  K aacaccattgtctcttcttacaaccgaaacttcactggccgaaacgattctaaccctgcc
 N  T  I  V  S  S  Y  N  R  N  F  T  G  R  N  D  S  N  P  A acccacgctttcgtcacctctcccgatctcgtcaccgctttcgccattgctggtgacctc
 T  H  A  F  V  T  S  P  D  L  V  T  A  F  A  I  A  G  D  L cgattcaaccctctcactgactccctgaaggattctgagggtaaggagttcaagctcaag
 R  F  N  P  L  T  D  S  L  K  D  S  E  G  K  E  F  K  L  K gagcccactggaaagggtctgcccgaccgaggttacgaccccggcatggacacctaccag
 E  P  T  G  K  G  L  P  D  R  G  Y  D  P  G  M  D  T  Y  Q gctcccccgccgaccgatctgccgtcgaggttgatgtttcccccacttccgaccgactc
 A  P  P  A  D  R  S  A  V  E  V  D  V  S  P  T  S  D  R  L cagatcctcaagcccttcaagccttgggacggcaaggacggtattgacatgcccatcctc
 Q  I  L  K  P  F  K  P  W  D  G  K  D  G  I  D  M  P  I  L atcaagtctcttggtaagaccaccactgaccatatctctcaggccggtccctggcttaag
 I  K  S  L  G  K  T  T  T  D  H  I  S  Q  A  G  P  W  L  K taccgaggccatctccagaacatctccaacaactacatgattggagccatcaacgctgag
 Y  R  G  H  L  Q  N  I  S  N  N  Y  M  I  G  A  I  N  A  E aacgaggaggccaacaacgtccgaaaccagatcactggcgagtggggaggagttcccgag
 N  E  E  A  N  N  V  R  N  Q  I  T  G  E  W  G  G  V  P  E actgccattgcttaccgagacaacggtatccgatgggttgttgtcggaggtgataacttc
 T  A  I  A  Y  R  D  N  G  I  R  W  V  V  V  G  G  D  N  F ggtgagggttcttctcgagagcacgctgctcttgagcccgattcctcggtggtttcgcc
 G  E  G  S  S  R  E  H  A  A  L  E  P  R  F  L  G  G  F  A atcatcaccaagtcttttgcccgaattcacgagactaacctgaagaagcagggtctcctg
 I  I  T  K  S  F  A  R  I  H  E  T  N  L  K  K  Q  G  L  L ccccttaacttcgtcaacggtgctgactacgacaagatccagcccctccgataagatctcc
 P  L  N  F  V  N  G  A  D  Y  D  K  I  Q  P  S  D  K  I  S
```

```
-continued
attcttggtcttaaggacctttgccccggcaagaacgtcaccattgaggttaccccaag
 I  L  G  L  K  D  L  A  P  G  K  N  V  T  I  E  V  T  P  K gacggtgccaagtggaccaccgaggtttctcacacctacaactctgagcagctcgagtgg
 D  G  A  K  W  T  T  E  V  S  H  T  Y  N  S  E  Q  L  E  W ttcaagtacggctctgccctcaacaagatggctgcctccaagaaataa
 F  K  Y  G  S  A  L  N  K  M  A  A  S  K  K  *
```

The fusion polypeptides and nucleic acid molecules encoding the polypeptides can be generated using methods known in the art or described herein, e.g., recombinant techniques.

A nucleic acid sequence encoding a fusion polypeptide can be operably linked to a suitable promoter to produce an expression cassette. In one example, the expression cassette includes one coding sequence operably linked to a promoter. In another example, the expression cassette includes multiple coding sequences, all of which are in operative linkage with a promoter. In that case, it is preferred that a ribosomal binding site is incorporated 5' to each of the coding sequences. If desired, the coding sequences are subjected to codon optimization based on the optimal codon usage in the host cell.

As used herein, the term "promoter" refers to a nucleotide sequence containing elements that initiate the transcription of an operably linked nucleic acid sequence in a desired host cell. At a minimum, a promoter contains an RNA polymerase binding site. It can further contain one or more enhancer elements which, by definition, enhance transcription, or one or more regulatory elements that control the on/off status of the promoter. A promoter can be an inducible or constitutive promoter.

The expression cassette for expressing a fusion polypeptide described above can be introduced into a suitable host cell to produce a genetically modified cell. Positive transformants are selected and expression of the fusion polypeptide can be confirmed by methods known in the art, e.g., immune-blotting or enzymatic activity analysis. The modified cell can then be cultured in a suitable medium for itaconate production. For example, the medium can contain glucose, glycerol, or citrate as the precursor for making itaconate. See, e.g., U.S. Pat. No. 8,192,965. After a sufficient culturing period, the secreted itaconate can be isolated from the medium.

Suitable host cells include, but are not limited to, *Aspergillus niger, Aspergillus terreus, Escherichia coli, Pseudozyma antarctica, Yarrowia lipotica*, and *Saccharomyces cerevisiae* cells.

The genetically modified cell described above can have a mutated endogenous icd gene (encoding an isocitrate dehydrogenase) so that it expresses a lower level of isocitrate dehydrogenase as compared with its host cell and/or wild-type counterpart. Isocitrate dehydrogenase converts isocitrate to α-ketoglutarate. Icd gene exists in various types of microorganisms, including *Aspergillus terreus* (GenBank Accession Nos. XM_001210553 and XP_001210553), *Citrobacter koseri* (GenBank Accession Nos. NC_009792 and No. YP_001453397), *Lactobacillus fermentum* (GenBank Accession Nos. NC_010610 and YP_001843755), *Saccharomyces cerevisiae* (GenBank Accession Nos. NM_001182876 and NP_014361), *Yarrowia lipolytica* (GenBank Accession Nos. XM_503571 and XP_503571), and *Escherichia coli* (GenBank Accession Nos. NC_000913 and NP_415654). Also see U.S. Pat. No. 8,143,036. Methods for producing a microorganism with a mutated endogenous icd gene are known in the art. For example, mutations (e.g., insertion, deletion, or substitution) of the icd gene can be introduced by homologous recombination. As an example, the coding region of an *E. coli* icd gene is shown below:

```
Nucleotide sequence (SEQ ID NO: 16) and amino acid sequence
(SEQ ID NO: 17) of an E. coli icd
atggaaagtaaagtagttgttccggcacaaggcaagaagatcaccctgcaaaacggcaaa
 M  E  S  K  V  V  V  P  A  Q  G  K  K  I  T  L  Q  N  G  K ctcaacgttcctgaaaatccgattatcccttacattgaaggtgatggaatcggtgtagat
 L  N  V  P  E  N  P  I  I  P  Y  I  E  G  D  G  I  G  V  D gtaaccccagccatgctgaaagtggtcgacgctgcagtcgagaaagcctataaaggcgag
 V  T  P  A  M  L  K  V  V  D  A  A  V  E  K  A  Y  K  G  E cgtaaaatctcctggatggaaatttacaccggtgaaaaatccacacaggtttatggtcag
 R  K  I  S  W  M  E  I  Y  T  G  E  K  S  T  Q  V  Y  G  Q gacgtctggctgcctgctgaaactcttgatctgattcgtgaatatcgcgttgccattaaa
 D  V  W  L  P  A  E  T  L  D  L  I  R  E  Y  R  V  A  I  K ggtccgctgaccactccggttggtggcggtattcgctctctgaacgttgccctgcgccag
 G  P  L  T  T  P  V  G  G  I  R  S  L  N  V  A  L  R  Q gaactggatctctacatctgcctgcgtccggtacgttactatcagggcactccaagcccg
 E  L  D  L  Y  I  C  L  R  P  V  R  Y  Y  Q  G  T  P  S  P gttaaacaccctgaactgaccgatatggttatcttccgtgaaaactcggaagacatttat
 V  K  H  P  E  L  T  D  M  V  I  F  R  E  N  S  E  D  I  Y gcgggtatcgaatggaaagcagactctgccgacgccgagaaagtgattaaattcctgcgt
 A  G  I  E  W  K  A  D  S  A  D  A  E  K  V  I  K  F  L  R gaagagatgggggtgaagaaaattcgcttcccggaacattgtggtatcggtattaagccg
 E  E  M  G  V  K  K  I  R  F  P  E  H  C  G  I  G  I  K  P
```

```
tgttcggaagaaggcaccaaacgtctggttcgtgcagcgatcgaatacgcaattgctaac
 C   S   E   E   G   T   K   R   L   V   R   A   A   I   E   Y   A   I   A   N gatcgtgactctgtgactctggtgcacaaaggcaacatcatgaagttcaccgaaggagcg
 D   R   D   S   V   T   L   V   H   K   G   N   I   M   K   F   T   E   G   A tttaaagactggggctaccagctggcgcgtgaagagtttggcggtgaactgatcgacggt
 F   K   D   W   G   Y   Q   L   A   R   E   E   F   G   G   E   L   I   D   G ggcccgtggctgaaagttaaaaacccgaacactggcaaagagatcgtcattaaagacgtg
 G   P   W   L   K   V   K   N   P   N   T   G   K   E   I   V   I   K   D   V attgctgatgcattcctgcaacagatcctgctgcgtccggctgaatatgatgttatcgcc
 I   A   D   A   F   L   Q   Q   I   L   L   R   P   A   E   Y   D   V   I   A tgtatgaacctgaacggtgactacatttctgacgccctggcagcgcaggttggcggtatc
 C   M   N   L   N   G   D   Y   I   S   D   A   L   A   A   Q   V   G   G   I ggtatcgcccctggtgcaaacatcggtgacgaatgcgccctgtttgaagccacccacggt
 G   I   A   P   G   A   N   I   G   D   E   C   A   L   F   E   A   T   H   G actgcgccgaaatatgccggtcaggacaaagtaaatcctggctctattattctctccgct
 T   A   P   K   Y   A   G   Q   D   K   V   N   P   G   S   I   I   L   S   A gagatgatgctgcgccacatgggttggaccgaagcggctgacttaattgttaaaggtatg
 E   M   M   L   R   H   M   G   W   T   E   A   A   D   L   I   V   K   G   M gaaggcgcaatcaacgcgaaaaccgtaacctatgacttcgagcgtctgatggatggcgct
 E   G   A   I   N   A   K   T   V   T   Y   D   F   E   R   L   M   D   G   A Aaactgctgaaatgttcagagtttggtgacgcgatcatcgaaaacatgtaa
 K   L   L   K   C   S   E   F   G   D   A   I   I   E   N   M   -
```

Alternatively or in addition, the genetically modified cell can express or over-express one or more of the following enzymes: (a) an enzyme that converts phosphoenolpyruvate to oxaloacetate (e.g., phosphoenolpyruvate carboxylase/carboxykinases, including three isoforms EC 4.1.1.32, EC 4.1.1.38, and EC 4.1.1.49, and also EC 4.1.1.31 that exhibits similar activity), (b) an enzyme that converts oxaloacetate to citrate (e.g., a citrate synthase, a 2-methylcitrate synthase, or a citrate lyase), and (c) an enzyme that converts citrate or isocitrate to cis-aconitic acid (e.g., an aconitase or a 2-methylcitrate dehydratase). Also see U.S. Pat. No. 8,143,036.

The terms "phosphoenolpyruvate carboxylase/carboxykinase," "citrate synthase," "2-methylcitrate synthase," "citrate lyase," and "2-methylcitrate dehydratase" each refer to all enzymes that possess the enzymatic activity described above, including both naturally-occurring enzymes and their functional equivalents.

Provided below are the nucleotide sequences and amino acid sequences of an *E. coli* phosphoenolpyruvate carboxylase (encoded by ppc gene) and an *E. coli* citrate synthase (encoded by gltA gene).

```
Nucleic acid sequence (SEQ ID NO: 18) and amino acid sequence
(SEQ ID NO: 19) of an E. coli phosphoenolpyruvate carboxylase
atgaacgaacaatattccgcattgcgtagtaatgtcagtatgctcggcaaagtgctggga
 M   N   E   Q   Y   S   A   L   R   S   N   V   S   M   L   G   K   V   L   G gaaaccatcaaggatgcgttgggagaacacattcttgaacgcgtagaaactatccgtaag
 E   T   I   K   D   A   L   G   E   H   I   L   E   R   V   E   T   I   R   K ttgtcgaaatcttcacgcgctggcaatgatgctaaccgccaggagttgctcaccaccta
 L   S   K   S   S   R   A   G   N   D   A   N   R   Q   E   L   L   T   T   L caaaatttgtcgaacgacgagctgctgcccgttgcgcgtgcgtttagtcagttcctgaac
 Q   N   L   S   N   D   E   L   L   P   V   A   R   A   F   S   Q   F   L   N ctggccaacaccgccgagcaataccacagcatttcgccgaaaggcgaagctgccagcaac
 L   A   N   T   A   E   Q   Y   H   S   I   S   P   K   G   E   A   A   S   N ccggaagtgatcgcccgcaccctgcgtaaactgaaaaaccagccggaactgagcgaagac
 P   E   V   I   A   R   T   L   R   K   L   K   N   Q   P   E   L   S   E   D accatcaaaaaagcagtggaatcgctgtcgctggaactggtcctcacggctcacccaacc
 T   I   K   K   A   V   E   S   L   S   L   E   L   V   L   T   A   H   P   T gaaattacccgtcgtacactgatccacaaaatggtggaagtgaacgcctgttttaaaacag
 E   I   T   R   R   T   L   I   H   K   M   V   E   V   N   A   C   L   K   Q ctcgataacaaagatatcgctgactacgaacacaaccagctgatgcgtcgcctgcgccag
 L   D   N   K   D   I   A   D   Y   E   H   N   Q   L   M   R   R   L   R   Q
```

```
ttgatcgcccagtcatggcataccgatgaaatccgtaagctgcgtccaagcccggtagat
 L   I   A   Q   S   W   H   T   D   E   I   R   K   L   R   P   S   P   V   D gaagccaaatgggctttgccgtagtggaaaacagcctgtggcaaggcgtaccaaattac
 E   A   K   W   G   F   A   V   V   E   N   S   L   W   Q   G   V   P   N   Y ctgcgcgaactgaacgaacaactggaagagaacctcggctacaaactgcccgtcgaattt
 L   R   E   L   N   E   Q   L   E   E   N   L   G   Y   K   L   P   V   E   F gttccggtccgttttacttcgtggatgggcggcgaccgcgacggcaacccgaacgtcact
 V   P   V   R   F   T   S   W   M   G   G   D   R   D   G   N   P   N   V   T gccgatatcacccgccacgtcctgctactcagccgctggaaagccaccgatttgttcctg
 A   D   I   T   R   H   V   L   L   L   S   R   W   K   A   T   D   L   F   L aaagatattcaggtgctggtttctgaactgtcgatggttgaagcgacccctgaactgctg
 K   D   I   Q   V   L   V   S   E   L   S   M   V   E   A   T   P   E   L   L gcgctggttggcgaagaaggtgccgcagaaccgtatcgctatctgatgaaaaacctgcgt
 A   L   V   G   E   E   G   A   A   E   P   Y   R   Y   L   M   K   N   L   R tctcgcctgatggcgacacaggcatggctggaagcgcgcctgaaaggcgaagaactgcca
 S   R   L   M   A   T   Q   A   W   L   E   A   R   L   K   G   E   E   L   P aaaccagaaggcctgctgacacaaaacgaagaactgtgggaaccgctctacgcttgctac
 K   P   E   G   L   L   T   Q   N   E   E   L   W   E   P   L   Y   A   C   Y cagtcacttcaggcgtgtggcatgggtattatcgccaacggcgatctgctcgacaccctg
 Q   S   L   Q   A   C   G   M   G   I   I   A   N   G   D   L   L   D   T   L cgccgcgtgaaatgtttcggcgtaccgctggtccgtattgatatccgtcaggagagcacg
 R   R   V   K   C   F   G   V   P   L   V   R   I   D   I   R   Q   E   S   T cgtcataccgaagcgctgggcgagctgacccgctacctcggtatcggcgactacgaaagc
 R   H   T   E   A   L   G   E   L   T   R   Y   L   G   I   G   D   Y   E   S tggtcagaggccgacaaacaggcgttcctgatccgcgaactgaactccaaacgtccgctt
 W   S   E   A   D   K   Q   A   F   L   I   R   E   L   N   S   K   R   P   L ctgccgcgcaactggcaaccaagcgccgaaacgcgcgaagtgctcgatacctgccaggtg
 L   P   R   N   W   Q   P   S   A   E   T   R   E   V   L   D   T   C   Q   V attgccgaagcaccgcaaggctccattgccgcctacgtgatctcgatggcgaaaacgccg
 I   A   E   A   P   Q   G   S   I   A   A   Y   V   I   S   M   A   K   T   P tccgacgtactggctgtccacctgctgctgaaagaagcgggtatcgggtttgcgatgccg
 S   D   V   L   A   V   H   L   L   L   K   E   A   G   I   G   F   A   M   P gttgctccgctgtttgaaaccctcgatgatctgaacaacgccaacgatgtcatgacccag
 V   A   P   L   F   E   T   L   D   D   L   N   N   A   N   D   V   M   T   Q ctgctcaatattgactggtatcgtggcctgattcagggcaaacagatggtgatgattggc
 L   L   N   I   D   W   Y   R   G   L   I   Q   G   K   Q   M   V   M   I   G tattccgactcagcaaaagatgcgggagtgatggcagcttcctgggcgcaatatcaggca
 Y   S   D   S   A   K   D   A   G   V   M   A   A   S   W   A   Q   Y   Q   A caggatgcattaatcaaaacctgcgaaaaagcgggtattgagctgacgttgttccacggt
 Q   D   A   L   I   K   T   C   E   K   A   G   I   E   L   T   L   F   H   G cgcggcggttccattggtcgcggcggcgcacctgctcatgcggcgctgctgtcacaaccg
 R   G   G   S   I   G   R   G   G   A   P   A   H   A   A   L   L   S   Q   P ccaggaagcctgaaaggcggcctgcgcgtaaccgaacagggcgagatgatccgctttaaa
 P   G   S   L   K   G   G   L   R   V   T   E   Q   G   E   M   I   R   F   K tatggtctgccagaaatcaccgtcagcagcctgtcgctttataccggggcgattctggaa
 Y   G   L   P   E   I   T   V   S   S   L   S   L   Y   T   G   A   I   L   E gccaacctgctgccaccgccggagccgaaagagagctggcgtcgcattatggatgaactg
 A   N   L   L   P   P   P   E   P   K   E   S   W   R   R   I   M   D   E   L tcagtcatctcctgcgatgtctaccgcggctacgtacgtgaaaacaaagattttgtgcct
 S   V   I   S   C   D   V   Y   R   G   Y   V   R   E   N   K   D   F   V   P tacttccgctccgctacgccggaacaagaactgggcaaactgccgttgggttcacgtccg
 Y   F   R   S   A   T   P   E   Q   E   L   G   K   L   P   L   G   S   R   P gcgaaacgtcgcccaaccggcggcgtcgagtcactacgcgccattccgtggatcttcgcc
 A   K   R   R   P   T   G   G   V   E   S   L   R   A   I   P   W   I   F   A
```

```
tggacgcaaaaccgtctgatgctccccgcctggctgggtgcaggtacggcgctgcaaaaa
 W  T  Q  N  R  L  M  L  P  A  W  L  G  A  G  T  A  L  Q  K gtggtcgaagacggcaaacagagcgagctggaggctatgtgccgcgattggccattcttc
 V  V  E  D  G  K  Q  S  E  L  E  A  M  C  R  D  W  P  F  F tcgacgcgtctcggcatgctggagatggtcttcgccaaagcagacctgtggctggcggaa
 S  T  R  L  G  M  L  E  M  V  F  A  K  A  D  L  W  L  A  E tactatgaccaacgcctggtagacaaagcactgtggccgttaggtaaagagttacgcaac
 Y  Y  D  Q  R  L  V  D  K  A  L  W  P  L  G  K  E  L  R  N ctgcaagaagaagacatcaaagtggtgctggcgattgccaacgattcccatctgatggcc
 L  Q  E  E  D  I  K  V  V  L  A  I  A  N  D  S  H  L  M  A gatctgccgtggattgcagagtctattcagctacggaatatttacaccgacccgctgaac
 D  L  P  W  I  A  E  S  I  Q  L  R  N  I  Y  T  D  P  L  N gtattgcaggccgagttgctgcaccgctcccgccaggcagaaaaagaaggccaggaaccg
 V  L  Q  A  E  L  L  H  R  S  R  Q  A  E  K  E  G  Q  E  P gatcctcgcgtcgaacaagcgttaatggtcactattgccgggattgcggcaggtatgcgt
 D  P  R  V  E  Q  A  L  M  V  T  I  A  G  I  A  A  G  M  R aataccggctaa
 N  T  G  -

Nucleic acid sequence (SEQ ID NO: 20) and amino acid sequence
of an E. coli citrate synthase (SEQ ID NO: 21)
atggctgatacaaaagcaaaactcaccctcaacggggatacagctgttgaactggatgtg
 M  A  D  T  K  A  K  L  T  L  N  G  D  T  A  V  E  L  D  V ctgaaaggcacgctgggtcaagatgttattgatatccgtactctcggttcaaaaggtgtg
 L  K  G  T  L  G  Q  D  V  I  D  I  R  T  L  G  S  K  G  V ttcacctttgacccaggcttcacttcaaccgcatcctgcgaatctaaaattactttttatt
 F  T  F  D  P  G  F  T  S  T  A  S  C  E  S  K  I  T  F  I gatggtgatgaaggtattttgctgcaccgcggtttccgatcgatcagctggcgaccgat
 D  G  D  E  G  I  L  L  H  R  G  F  P  I  D  Q  L  A  T  D tctaactacctggaagtttgttacatcctgctgaatggtgaaaaaccgactcaggaacag
 S  N  Y  L  E  V  C  Y  I  L  L  N  G  E  K  P  T  Q  E  Q tatgacgaatttaaaactacggtgacccgtcataccatgatccacgagcagattacccgt
 Y  D  E  F  K  T  T  V  T  R  H  T  M  I  H  E  Q  I  T  R ctgttccatgctttccgtcgcgactcgcatccaatggcagtcatgtgtggtattaccggc
 L  F  H  A  F  R  R  D  S  H  P  M  A  V  M  C  G  I  T  G gcgctggcggcgttctatcacgactcgctggatgttaacaatcctcgtcaccgtgaaatt
 A  L  A  A  F  Y  H  D  S  L  D  V  N  N  P  R  H  R  E  I gccgcgttccgcctgctgtcgaaaatgccgaccatggccgcgatgtgttacaagtattcc
 A  A  F  R  L  L  S  K  M  P  T  M  A  A  M  C  Y  K  Y  S attggtcagccatttgtttacccgcgcaacgatctctcctacgccggtaacttcctgaat
 I  G  Q  P  F  V  Y  P  R  N  D  L  S  Y  A  G  N  F  L  N atgatgttctccacgccgtgcgaaccgtatgaagttaatccgattctggaacgtgctatg
 M  M  F  S  T  P  C  E  P  Y  E  V  N  P  I  L  E  R  A  M gaccgtattctgatcctgcacgctgaccatgaacagaacgcctctacctccaccgtgcgt
 D  R  I  L  I  L  H  A  D  H  E  Q  N  A  S  T  S  T  V  R accgctggctcttcgggtgcgaacccgtttgcctgtatcgcagcaggtattgcttcactg
 T  A  G  S  S  G  A  N  P  F  A  C  I  A  A  G  I  A  S  L tggggacctgcgcacggcggtgctaacgaagcggcgctgaaaatgctggaagaaatcagc
 W  G  P  A  H  G  G  A  N  E  A  A  L  K  M  L  E  E  I  S tccgttaaacacattccggaatttgttcgtcgtgcgaaagacaaaaatgattctttccgc
 S  V  K  H  I  P  E  F  V  R  R  A  K  D  K  N  D  S  F  R ctgatgggcttcggtcaccgcgtgtacaaaaattacgacccgcgcgccaccgtaatgcgt
 L  M  G  F  G  H  R  V  Y  K  N  Y  D  P  R  A  T  V  M  R gaaacctgccatgaagtgctgaaagagctgggcacgaaggatgacctgctggaagtggct
 E  T  C  H  E  V  L  K  E  L  G  T  K  D  D  L  L  E  V  A
```

```
                          -continued
atggagctggaaaacatcgcgctgaacgacccgtactttatcgagaagaaactgtacccg
 M   E   L   E   N   I   A   L   N   D   P   Y   F   I   E   K   K   L   Y   P aacgtcgatttctactctggtatcatcctgaaagcgatgggtattccgtcttccatgttc
 N   V   D   F   Y   S   G   I   I   L   K   A   M   G   I   P   S   S   M   F accgtcattttcgcaatggcacgtaccgttggctggatcgcccactggagcgaaatgcac
 T   V   I   F   A   M   A   R   T   V   G   W   I   A   H   W   S   E   M   H agtgacggtatgaagattgcccgtccgcgtcagctgtatacaggatatgaaaaacgcgac
 S   D   G   M   K   I   A   R   P   R   Q   L   Y   T   G   Y   E   K   R   D Tttaaaagcgatatcaagcgttaa
 F   K   S   D   I   K   R   -
```

Table 1 below lists additional examples of phosphoenolpyruvate carboxylases/carboxykinase, citrate synthases, and aconitases, as well as exemplary 2-methylcitrate synthases, citrate lyases, and 2-methylcitrate dehydratase:

The above-described genetically modified cell can be constructed by methods known in the art, e.g., recombinant technology. A sequence encoding any of the above-described enzymes can be operably linked to a suitable promoter to produce an expression cassette, which can then be introduced into a host cell.

TABLE 1

| Enzymes | GenBank Accession Numbers |
|---|---|
| Phosphoenolpyruvate carboxykinase/ carboxylase | NP_417862 (*E. coli*, EC4.1.1.49); AAB07805 (*Staphylococcus aureus*, EC4.1.1.32); CAC32156 (*Mycobacterium leprae*, EC 4.1.1.32); XP_645396 (*Dictyostelium discoideum*, EC 4.1.1.32); NP_013023 (*S. cerevisiae*, EC 4.1.1.49); XP_001215073 (*A. terreus*, EC 4.1.1.49); PC2168 (*Brassica napus*, EC4.1.1.38); NP_850372 (*Arabidopsi thaliana*, EC 4.1.1.31); CAA35251 (*Sorghum bicolor*, EC 4.1.1.31); CAB95920 (*Streptomyces coelicolor*); XP_001391222 (*A. niger*, EC 4.1.1.49) and XP_501928 (*Y. lipolytica*, EC 4.1.1.49) |
| Citrate synthase | AAC73814 (*E. coli*); NP_001080194 (*Xenopus laevis*); CAB66275 (*S. coelicolor*); NP_080720 (*Mus musculus*); ABP36423 (*Chlorobium phaeovibrioides*); XP_001827205 (*Aspergillus oryzae*); NP_014398 (*S. cerevisiae*); XP_503469 (*Y. lipolytica*); XP_001393983 (*A. niger*) and XP_001216611 (*A. terreus*) |
| 2-methylcitrate synthase | ABN63514 (*Shewanella baltica*); ABI57944 (*Alkalilimnicola ehrlichei*); XP_001396731 (*A. niger*); XP_503380 (*Y. lipolytica*); NP_414867 (*E. coli*); XP_001209805 (*A. terreus*); NP_390294 (*Bacillus subtilis*) and NP_459364 (*Salmonella typhimurium*) |
| Citrate lyase | WP_011575489 (*Pseudoalteromonas atlantica*); ABH11558 (*Lactobacillus helveticus*); AAL50820 (*Rhodococcus erythropolis*); YP_488905 (*E. coli*); XP_750953 (*Aspergillus fumigatus*) and YP_651218 (*Yersinia. pestis*) |
| Aconitase | CAA90177 (*Bos taurus*); CAQ01753 (*Clavibacter michiganesis*); CAC37548 (*S. coelicolor*); AAC46192 (*Mycobacterium avium*); NP_414660 (*E. coli*); NP_013407 (*S. cerevisiae*); XP_502616 (*Y. lipolytica*); XP_503960 (*Y. lipolytica*); AAC61778 (*A. terreus*); and WP_011744016 (*Chlorobium phaeobacteroides*) |
| 2-methylcitrate dehydratase | WP_008953837 (*Pseudogulbenkiania ferrooxidans*); WP_006384082 (*Stenotrophomonas maltophilia*); YP_488628 (*E. coli*); NP_015326 (*S. cerevisiae*); XP_504908 (*Y. lipolytica*); XP_001209777 (*A. terreus*) and WP_012403641 (*Burkholderia phymatum*) |

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited are hereby incorporated by reference herein in their entirety.

Example 1

Construction of Cad-Aco Fusion Genes with acnA or acnB from *E. coli*

The approaches reported by Tsuchiya et al (Biochim. Biophysi. Acta, 2008, 1784:1847-1856) were adopted to design the CAD-Aco fusion polypeptides, which each contained a CAD at the N-terminal end and an Aco at the C-terminal end, linked with a short peptide containing 25 amino acids rich in PG (SEQ ID NO:7). The C-terminus of the CAD was also modified slightly, with the incorporation of a V490GI mutation. In the case of Aco, three types of aconitase were tested: AcnA, AcnB, and the AcnB E424Q mutant. In total, 3 types of CAD-Aco fusion polypeptides were then constructed: CAD-AcnA, CAD-AcnB, and CAD-AcnB E424Q (SEQ ID NOs: 9, 11, and 13, respectively).

Figure 2:
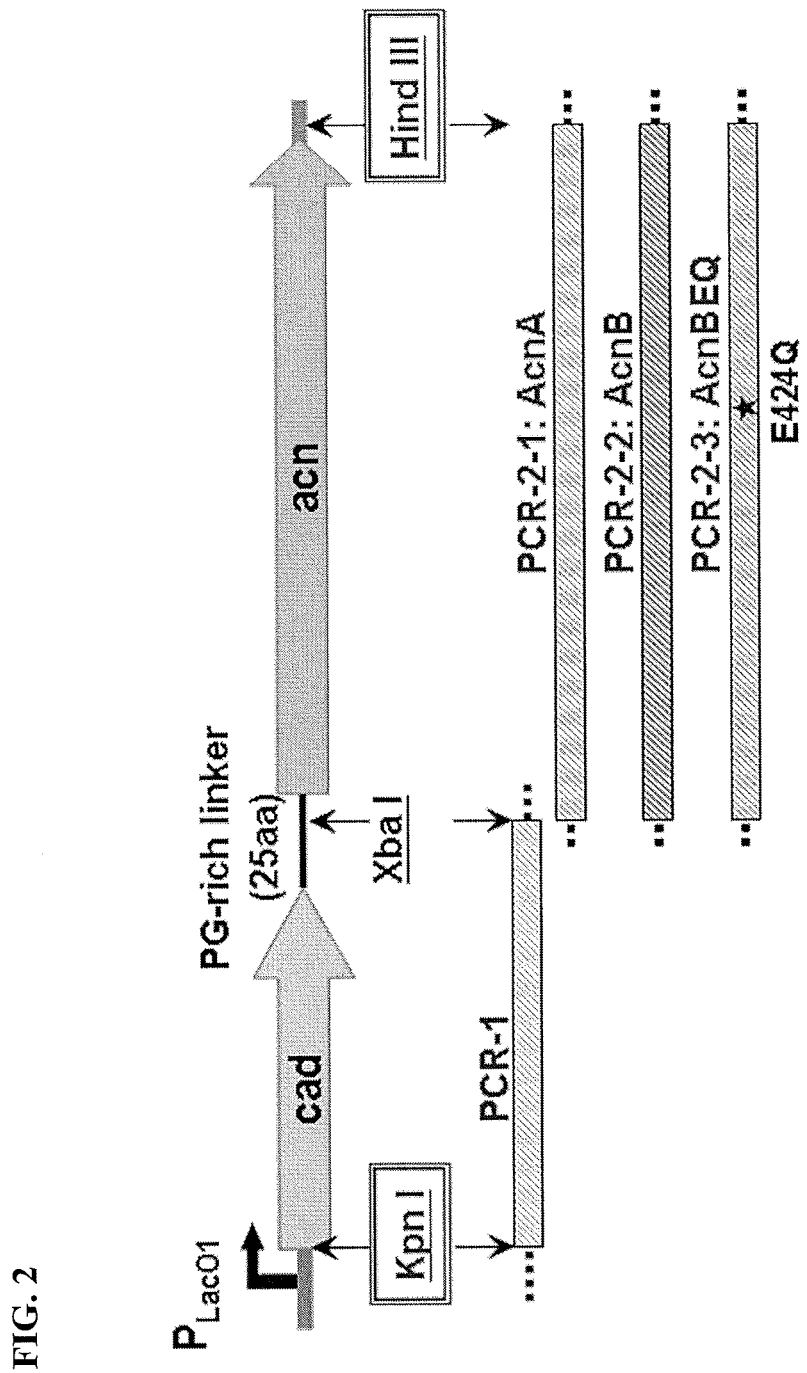
FIG. 2 is a schematic representation of a cad-aco fusion gene and the PCR strategies used for gene cloning. The internal XbaI site located on the linker region was used to join the two types of PCR-1 and PCR-2 fragments together. The KpnI and HindIII sites (boxed) were used to insert the fusion gene into pSA40a at the corresponding sites on the vector. All three fragments were joined together in a single ligation reaction.

To construct the fusion genes, primers and PCR were applied to amplify two DNA fragments independently: 1) Fragment PCR-1, which included the cad coding region and the linker, and was flanked with a KpnI site right upstream of the cad and a XbaI site located in the linker region; 2) Fragment PCR-2, which contained only part of the linker and an intact aconitase gene, and was flanked with the XbaI site in the linker and a HindIII site downstream of the aconitase gene. See FIG. 2. As there were three different aconitase genes to test, three different PCR-2 fragments were prepared. All of them shared the same features mentioned above and shown in FIG. 2. The primers used are listed in Table 2 below.

TABLE 2

Primers used for generating cad-acnA, cad-acnB, and cad-acnB [E424Q] fusion genes

| Names | Locations | Sequences |
|---|---|---|
| Lac-f | promoter: P$_L$lacO1 | F GTGAGCGGATAACAATTGACAT (SEQ ID NO: 22) |
| C13-0418-01 | cad (V490GI)-Linker | F TGTCCGGTTAAATCCCCACTGG GTATTGAATTTG (SEQ ID NO: 23) |
| C13-0410-01 | cad (V490GI)-Linker | F TGTCCGGTTAAATCCCCACTGG GTATTGAATTTGGTCCGGGTC (SEQ ID NO: 24) |
| C13-0410-02 | Linker | R AGAGGGCCAGGACCAGGACCTG GACCCGGACCAAATTCAATA (SEQ ID NO: 25) |
| C13-0410-03 | Linker (XbaI site) | F CCTGGTCCTGGCCCTCTAGAAG TGTTGTTCCAAGGTCC (SEQ ID NO: 26) |
| C13-0410-04 | Linker-AcnB (1st-2nd codons) | R TAGCACGAGTTTCGCACGACCA GGACCTTGGAACAACACTT (SEQ ID NO: 27) |
| C13-0410-05 | Linker-AcnB (1st-10th codons) | F CGTGCGAAACTCGTGCTAGAAG AATACCGTAAGCACGTAGC (SEQ ID NO: 28) |

TABLE 2-continued

Primers used for generating cad-acnA, cad-acnB, and cad-acnB [E424Q] fusion genes

| Names | Locations | Sequences |
|---|---|---|
| C13-0410-06 | AcnB (C-terminus) | R GCTTATCGATACCGTCGACTTA AACCGCAGTCTGGAAAATCA (SEQ ID NO: 29) |
| C13-0410-07 | HindIII-end | R GGAATTCGATATCAAGCTTATC GATACCGTCGACTTA (SEQ ID NO: 30) |
| C13-0412-01 | Linker-ATG (initiation) | R CATGAGTTTCGCACGACCAGGA CCTTGGAACAACACTT (SEQ ID NO: 31) |
| C13-0412-02 | Linker-AcnA (1st-9th codons) | F GGTCGTGCGAAACTCATGTCGT CAACCCTACGAGAAGCCA (SEQ ID NO: 32) |
| C13-0412-03 | AcnA (C-terminus) | R CTTATCGATACCGTCGACTTAC TTCAACATATTACGAATGACAT (SEQ ID NO: 33) |
| C13-0413-01 | AcnB/E424Q mutation | F ACACCACCGGCCCGATGACCCG TGATCAGCTGAAAGA (SEQ ID NO: 34) |
| C13-0413-02 | AcnB/E424Q mutation | R AGGCACGCCAGGTCTTTCAGC TGATCACGGGTCAT (SEQ ID NO: 35) |
| C13-0415-01 | 3 bp-upsteam of AcnB/E424Q | R ACGGGTCATCGGGCCGGTGGTG T (SEQ ID NO: 36) |
| C13-0415-02 | 3 bp-downsteam of AcnB/E424Q | F AAAGACCTGGCGTGCCTGGGCT T (SEQ ID NO: 37) |

The prepared PCR-1 and PCR-2 fragments were gel purified, and treated either with KpnI and XbaI (for PCR-1 type), or with XbaI and HindIII (for PCR-2 types), and ligated with pSA40a vector at KpnI/HindIII sites, via a three-fragments-ligation approach. The following three recombinant clones were then constructed: pTYL101, pTYL102 and pTYL103, which carried P$_L$lacO1::cad-linker-acnA ("cad-acnA"), P$_L$lacO1::cad-linker-acnB ("cad-acnB"), and P$_L$lacO1::cad-linker-acnB (E424Q) ("cad-acnBeq") on each plasmid, respectively. Table 3 below lists the expression plasmids described herein.

TABLE 3

Expression plasmids

| Names | Genotypes |
|---|---|
| pPC1 | ColE1 ori; Kan$^r$; P$_L$lacO1::cad$_{AT}$ (cad from *A. tserrues*; P$_L$lacO1, synthetic promoter induced by IPTG) |
| pPC2 | ColE1 ori; Amp$^r$; P$_L$lacO1::acnA$_{EC}$ (acnA from *E. coli*) |
| pPC3 | ColE1 ori; Amp$^r$; P$_L$lacO1::acnB$_{EC}$ (acnB from *E. coli*) |
| pPC6 | ColE1 ori; Spc$^r$; P$_L$lacO1::ppc$_{EC}$::gltA$_{EC}$ (transcriptional fusion; ppc from *E. coli*; gltA from *E. coli*) |
| pTYL101 | ColE1 ori; Amp$^r$; P$_L$lacO1::cad-linker-acnA$_{EC}$ (translational fusion) |
| pTYL102 | ColE1 ori; Amp$^r$; P$_L$lacO1::cad-linker-acnB$_{EC}$ (translational fusion) |
| pTYL103 | ColE1 ori; Amp$^r$; P$_L$lacO1::cad-linker-acnBeq (translational fusion; acnBeq, mutant acnB$_{EC}$ carrying missense mutation E424Q) |
| pTYL107 | ColE1 ori; Amp$^r$; P$_L$lacO1::cad-linker-Aco1$_{YL}$ (translational fusion; aco1 from *Yarrowia lipolytica*) |
| pTYL112 | ColE1 ori; Amp$^r$; P$_{CP25}$::cad-linker-acnA$_{EC}$ (derived from pTYL101) |

TABLE 3-continued

Expression plasmids

| Names | Genotypes |
|---|---|
| pSA40a | ColE1 ori; Amp$^r$; cloning vector |
| pP104A | ColE1 ori; Amp$^r$; P$_L$lacO1::cad::acnA$_{EC}$ (transcriptional fusion) |
| pP154K | ColE1 ori; Kan$^r$; P$_L$lacO1::cad::acnB$_{EC}$ (transcriptional fusion) |
| pP154A | ColE1 ori; Amp$^r$; P$_L$lacO1::cad::acnB$_{EC}$ (transcriptional fusion; derived from pP154K, by replacing Kan$^r$ gene with Amp$^r$ gene) |
| pP190A | ColE1 ori; Amp$^r$; P$_L$lacO1::acnA$_{AT}$ (acnA from A. terreus) |

Example 2

The CAD-Aco Fusion Proteins Exhibited Both CAD and Aco Activities

Plasmids pTYL101, pTYL102, and pTYL103 were respectively introduced into E. coli SY403K (genotype: BW25113 acnA- acnB- icd-kan$^r$), and expression of the cad-aco fusion genes on these plasmids were induced with 0.5 mM IPTG. Cell lysates prepared from IPTG-induced cultures were analyzed in an in vitro assay to test the activities of the CAD-Aco proteins. Positive and negative control lysates were prepared with similar procedures by introducing pP104A, which carried transcriptionally fused P$_L$lacO1::cad::acnA operon, and pSA40a, the vector, into E. coli SY403K cells, respectively. Table 4 below lists the bacterial strains disclosed herein.

TABLE 4

E. coli strains

| Names | Genotypes (plasmids included) |
|---|---|
| EPI300 ™ | F$^-$ mcrA Δ(mrr-hsdRMS-mcrBC) Φ80dlacZΔM15 ΔlacZX74 recA1 endA1 araD139 Δ(ara, leu) 7697 galU galK λ$^-$ rpsL nupG trfA dhfr (Epicentrae Biotechnologies, Medison, USA) |
| PC1400* | BW25113 icd$^-$ carrying uncharacterized mutation that improves cell growth in fermentation medium containing yeast extract, glycerol and 1xM9 salts |
| SY403K | BW25113 acnA$^-$ acnB$^-$ icd$^-$ Kan$^r$ |
| RT001 | SY403K (pTYL101) |
| RT002 | SY403K (pTYL102) |
| RT003 | SY403K (pTYL103) |
| RT007 | SY403K (pSA40a) |
| RT008 | SY403K (P104A) |
| RT010 | SY403K (pP154A) |
| RT014 | PCI400* (pPC6, pTYL101) |
| RT015 | PCI400* (pPC6, pTYL102) |
| RT017 | PCI400* (pPC6, pP104A) |
| RT018 | PCI400* (pPC6, pP154A) |
| RT021 | SY403K (pPC6, pTYL101) |
| RT022 | SY403K (pPC6, pTYL102) |
| RT023 | SY403K (pPC6, pTYL103) |
| RT024 | SY403K (pPC6, pTYL107) |
| RT027 | SY403K (pPC6, pP190A) |
| RT030 | SY403K (pPC6, pSA40a) |
| RT031 | SY403K (pPC6, pP104A) |
| RT032 | SY403K (pPC6, pP154A) |
| RT101 | PCI400* (pPC1, pPC6, pTYL101) |
| RT109 | PCI400* (pP154K, pPC6, pP104A) |
| RT113 | PCI400* (pPC1, pPC6, pTYL112) |
| RT114 | PCI400* (pPC1, pPC6, pSA40a) |
| RT125 | PCI400* (pSA40a, pPC6, pP104A) |
| RT127 | PCI400* (pPC1, pPC6, pP104A) |

0.2 mL cell lysates of tested samples were used in 1 mL reaction mixtures, which contained cis-aconitate (12.5 mM) in MES-NaOH (50 mM, pH 6.5) buffer, and were incubated at 37° C. for 25 min. To stop the reactions, 3-4 μL of a concentrated (18M) H$_2$SO$_4$ solution were added. The sample solutions were then filtered with a 0.2 μM filter and analyzed with HPLC to detect the presence of itaconate, citrate (isocitrate), and the amount of cis-aconitate left. The results are shown in Table 5 below.

TABLE 5

| | | | Chemicals (mg/L per mg of total proteins in the cell lysates)* | | |
|---|---|---|---|---|---|
| Strains | Plasmids | cad/aco genes | Itaconate, yielded | cis-Aconitate, left | Citrate#, yielded |
| RT001 | pTYL101 | cad-acnA | 1.88 ± 0.07 | 78.45 ± 8.65 | 1036.61 ± 73.67 |
| RT002 | pTYL102 | cad-acnB | 1.77 ± 0.29 | 114.38 ± 3.22 | 0 ± 0.00 |
| RT003 | pTYL103 | cad-acnB E424Q | 1.49 ± 0.10 | 163.26 ± 24.14 | 0 ± 0.00 |
| RT008 | pPC104A | cad, acnA | 0.67 | 60.73 | 1016.64 |
| RT007 | pSA40a | none | 0.10 | 190.56 | 0 |

*For pTYL101, pTYL102 and pTYL103, two randomly picked clones were used to prepare cell lysates and to perform in vitro analysis independently. The results listed here were means of data from the two samples.
The data included not only citrate but also isocitrate, as analyzed HPLC signals of these two compounds were mixed together.

Cell lysates from cells expressing CAD-Aco fusion proteins (either from pTYL101, pTYL102 or pTYL103) contained significant amounts of itaconate, as compared with positive and negative controls, indicating that all three types of CAD-Aco fusion proteins possessed CAD activity. In the case of CAD-AcnA (from pTYL101), formation of citrate/isocitrate, and also the consumption of cis-aconitate, were comparable to the positive control (expressed with AcnA from pP104A), supporting that at least CAD-AcnA possesses Aco activity. It was known that AcnB is unstable upon cell lysis, and without re-activation, e.g., supplemented with Fe2+/S2−, no activity can be detected. This is the very reason that no citrate/isocitrate was detected in samples lysates of cells expressing CAD-AcnB (pTYL102) or CAD-AcnB/E424Q (pTYL103). Their aconitase activities were shown by the in vivo cultivation assays described below.

Example 3

Cis-Aconitate Release was Increased in Cells Expressing Cad-Aco Fusion Genes A. E. coli SY403K, a Mutant with acnA- acnB- icd-Mutations
To compare the itaconate production efficiency between cad-aco fusion proteins and their individual counterparts, strains RT001, RT002, RT008 and RT010, all based on *E. coli* SY403K host cells, were tested for their capabilities to produce itaconate.

Overnight cultures of the tested strains were prepared with 2-3 mL of LB medium (supplemented with antibiotics), from which 0.2-0.4 mL cell suspensions were seeded, respectively, into 40 mL of fermentation medium (0.5% yeast extract, 0.05% peptone, 3% glycerol, 1×M9 salts, pH7.0) maintained in a 250 mL-flask. These culture flasks were, at first, incubated at either 30° C. or 37° C. with rotation (200×rpm), until cells OD600 nm reached to about 0.2-0.4. IPTG were then added to a concentration of 0.5 mM and the flasks were further incubated at 30° C. for about 64 hours. During the cultivations, a 1 mL sample was removed from each sample flasks at selected times, for analyzing the amount of itaconate and cis-aconitate accumulated in the medium.

Figure 3:
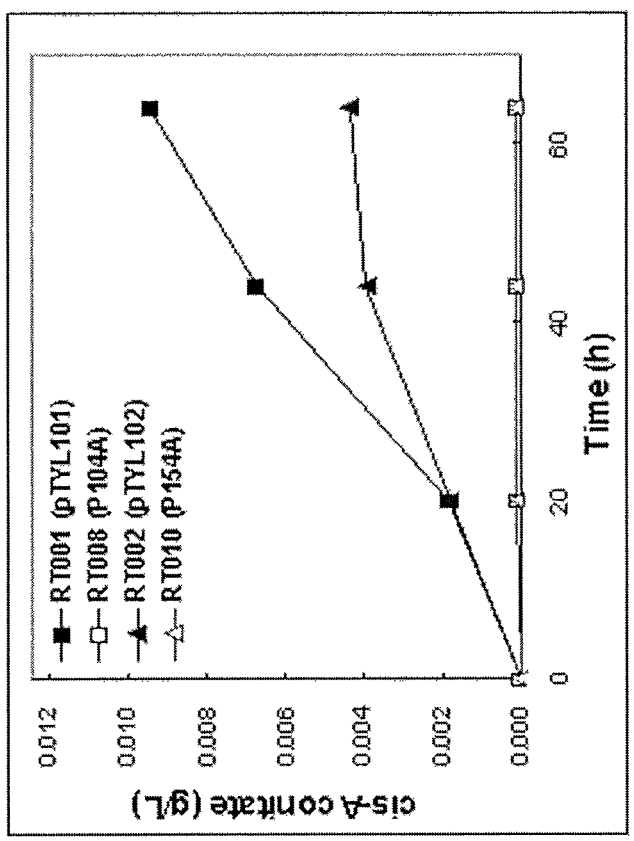
FIG. 3 is a set of graphs showing yields of itaconate (A) and cis-aconitate (B) among strains carrying different cad-aco fusions or cad and aco genes. These strains were all derived from the same host, *E. coli* SY403K. The plasmid carried by each strain is shown in parenthesis.
Figure 3:
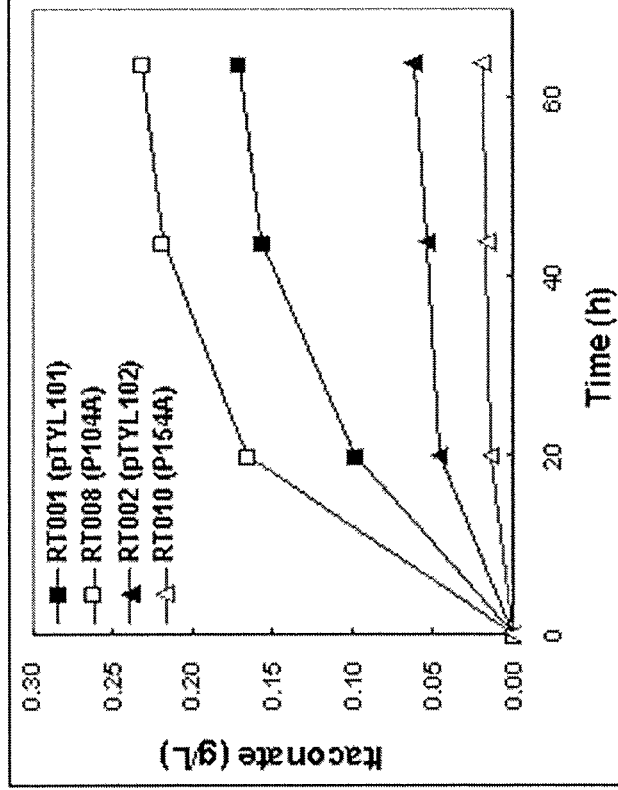

As shown in FIG. 3, significant amounts of itaconate were accumulated in cells carrying translationally fused cad-aco fusion genes, supporting that these genes did encode active bi-functional fusion proteins, providing not only CAD activities required for itaconate synthesis, but also the Aco activities required for the formation of cis-aconitate, the only substrate for CAD enzymes.

Among the samples, it was also noted that cells carrying acnA, fused with cad either translationally, as in RT001, or transcriptionally, as in RT008, accumulated more of itaconate than that of cells carrying acnB (i.e., RT002 and RT010). As the chromosomal acnA and acnB have been deleted in the host cells, Aco activities of RT008 and RT010 were mainly from AcnA and AcnB, respectively, each provided by the plasmids they carried.

Notably, itaconate yield of RT002 was even higher than that of RT010, suggesting that CAD-Aco fusion has beneficial impact on itaconate production, which probably resulted from efficient catch of cis-aconitate by CAD closely associated with AcnB. Besides, this beneficial effect was more prominent when supplement of cis-aconitate was limited, as in the cases of RT002 and RT010. In those cases, the AcnB activities were probably low due to the high Km of AcnB for citrate, either as an individual enzyme or functionally fused with CAD.

It is also noted that, regardless of their itaconate yields, releases of cis-aconitate were significantly increased only in RT001 and RT002, which carries cad-aco fusion genes on plasmids, and not in RT008 or RT010, which individually expressed with either AcnA or AcnB enzymes.

Strains RT021, RT022, and RT023 were generated by co-transformation of cad-aco fusion gene systems and plasmid pPC6, carrying $P_L$lacO1::ppc::gltA operon, into *E. coli* SY403K cells. Controls RT031 and RT032, carrying either plasmid pP104A or pP154A, were also generated in similar ways. Productions of itaconate during fermentation were compared among these strains, along with their releases of cis-aconitate.

Overnight cultures of the tested samples were prepared with 2-3 mL of LB medium (supplemented with antibiotics), from which 0.2-0.4 mL cell suspensions were seeded, respectively, into 30 mL of fermentation medium (0.4% yeast extract, 2% glycerol, 1×M9 salts, pH7.0) maintained in a 250 mL-flask. These culture flasks were, at first, incubated at either 30° C. or 37° C. with rotation (200×rpm), until cells OD600 nm reached to about 0.2-0.4. IPTG were then added to a concentration of 0.5 mM and the flasks were further incubated at 30° C. for about 64 hours. During cultivation, a 1 mL sample was removed from each sample flask at selected times for analyzing the amount of itaconate and cis-aconitate accumulated in the medium. The results are shown in FIG. 4.

Figure 4:
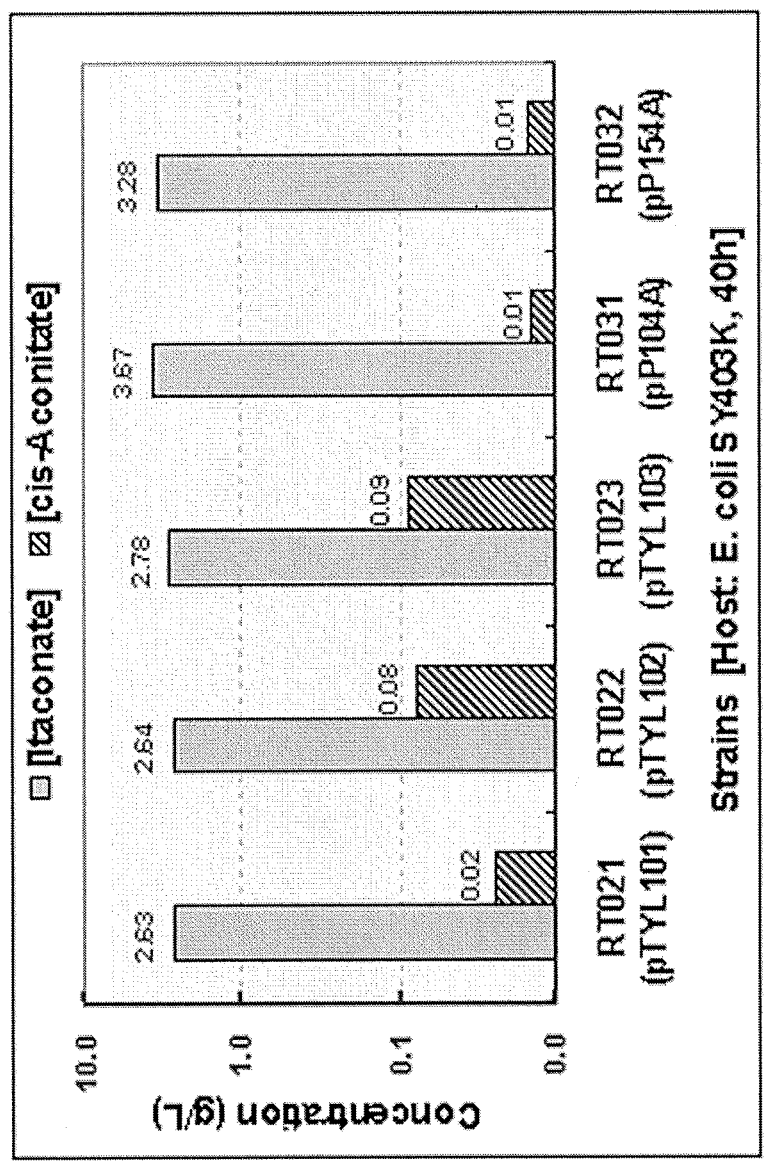
FIG. 4 is a graph showing itaconate and cis-aconitate productions among different strains supplied with an excess of citrate. These strains were all derived from the same host, *E. coli* SY403K. Each strain carried two plasmids, pPC6, for the excess supply of citrate, and a plasmid to test for function, which is listed in parenthesis.

As shown in FIG. 4, more than 10-folds of improvement in itaconate yields were observed in all samples tested, as compared with the yields obtained in the absence of pPC6 (see FIG. 3), especially for cells that expressed AcnB, either as an individual enzyme or in the form of CAD-AcnB fusions. The excess supply of citrate in these cells fully energized the AcnB enzymes, resulting in efficient production of cis-aconitate, which further activated the CAD enzymes in the same cells, leading to the increase of itaconate productions and also the release of cis-aconitate. Again, it is noted that release of cis-aconitate was significantly higher in cells carrying cad-aco fusion genes than that of cells carrying transcriptionally fused cad and aco genes.

B. *E. coli* PCI400*, a Mutant Carrying icd-Mutation

In *E. coli* SY403K cells, the chromosomal acnA and acnB genes have been deleted. To test the effects of these chromosome-encoded aco genes on the production of itaconate from cad-aco fusion genes, we then co-transformed the cad-aco expression systems and pPC6 plasmids into *E. coli* PCI400*, which carries an icd-deletion and a uncharacterized mutation that favors cell growth in the fermentation medium used. These strains, RT014, RT015, RT017 and RT018, were compared with each other regarding their production yields of itaconate and relative amounts of the cis-aconitate released.

Overnight cultures of the tested samples were prepared with 2-3 mL of LB medium (supplemented with antibiotics), from which 0.2-0.4 mL cell suspensions were seeded, respectively, into 40 mL of fermentation medium (0.5% yeast extract, 0.05% peptone, 3% glycerol, 1×M9 salts, pH7.0) maintained in a 250 mL-flask. These culture flasks were, at first, incubated at either 30° C. or 37° C. with rotation (200× rpm), until cells OD600 nm reached to about 0.2-0.4. IPTG were then added to a concentration of 0.5 mM and the flasks were further incubated at 30° C. for about 64 hours. During the cultivation, a 1 mL sample was removed from each sample flasks at selected times, for analyzing the amount of itaconate and cis-aconitate accumulated in the medium.

Figure 5:
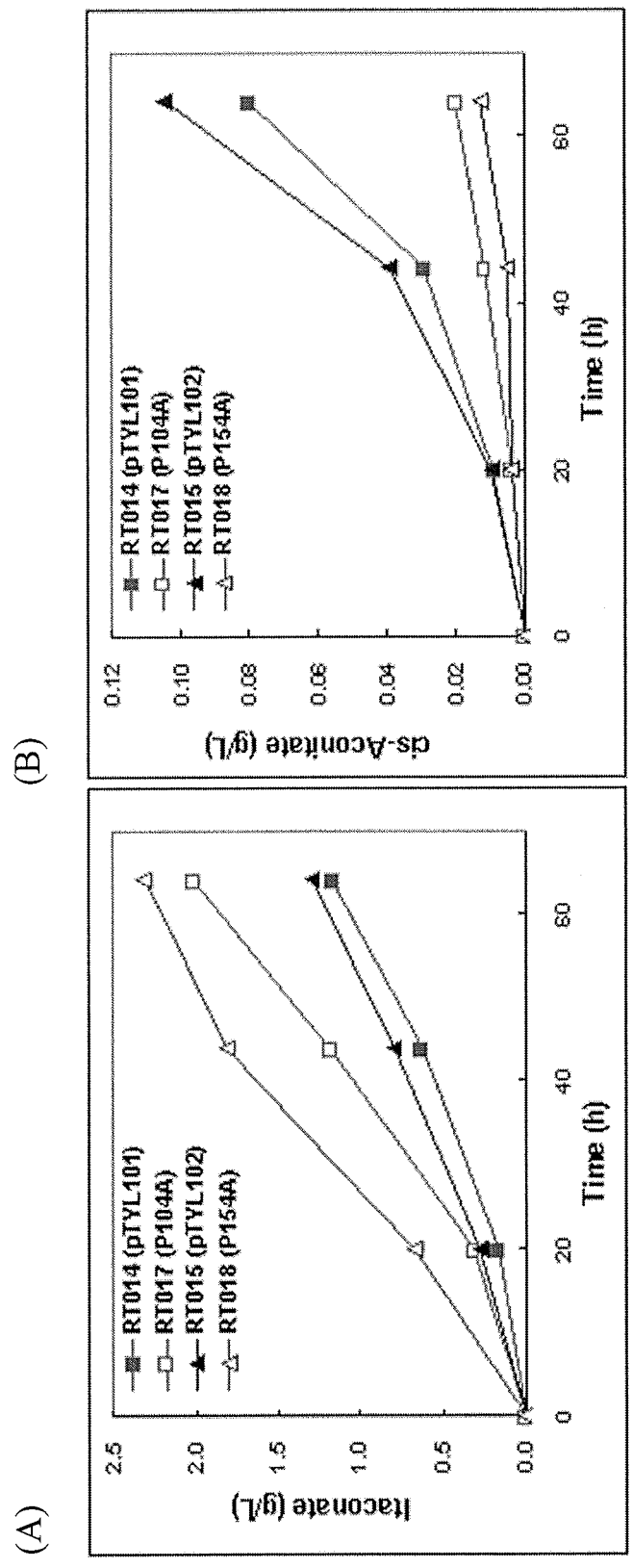
FIG. 5 is a set of graphs showing itaconate (A) and cis-aconitate (B) productions among different strains supplied with an excess of citrate. These strains were derived from the same host, *E. coli* PCI400\*, and each carried two plasmids, pPC6 and the plasmid (listed in parenthesis) to test for function.

As shown in FIG. 5, in these PCI400*-based strains, the relative amounts of itaconate produced and cis-aconitate released were similar with those observed in strains based on SY403K host (see FIGS. 3 and 4), though the yields of itaconate seemed to be less in PCI400*-based strains than in SY403K-based ones.

The above tests demonstrated that cells expressing cad-aco fusion genes released more of cis-aconitate than the cells that expressed similar, but individual, cad and aco genes, regardless of the presence or absence of the chromosome-encoded aco genes, and along with or without the co-overexpression of ppc and gltA genes that may supply citrate in excess in the cells. It was also demonstrated above that the close association of CAD and Aco enzymes on the fusion constructs did benefit the CAD part of the fusion enzyme to catch cis-aconitate released from the Aco part in the neighborhood, which is more prominent when the supply of cis-aconitate is limited (see FIG. 1).

Example 4

Co-Overexpression of Cad-Aco and Cad Genes Promoted Efficient Production of Itaconate Two approaches were tested to improve the conversion of cis-aconitate to itaconate. First, a strong constitutive promoter, $P_{CP}25$ (Jensen and Hammer, 1998, Biotechnol. Bioeng. 5:191-195) was selected to increase the expression level of cad-acnA gene; plasmid pTYL112, carrying $P_{CP}25$::cad-AcnA gene, was constructed for this purpose. Second, plasmid pPC1, which carried P$_L$lacO1::cad gene, was introduced into PCI400* cells, along with pPC6 and the cad-acnA expression plasmid, either pTYL101 or pTYL112. Production yields of itaconate were compared among these strains and the controls, a strain containing either pP104A, which carried transcriptionally fused cad and acnA genes, or pSA40a, the cloning vector.

Overnight cultures of the tested samples were prepared with 2-3 mL of LB medium (supplemented with antibiotics), from which 0.2-0.4 mL cell suspensions were seeded, respectively, into 40 mL of fermentation medium (0.4% yeast extract, 2% glycerol, 1×M9 salts, pH7.0) maintained in a 250 mL-flask. These culture flasks, at first, were incubated with rotation (200×rpm) at 30° C. for 4-5 hours. IPTG was then added to each sample and to a concentration of 0.5 mM, regardless of their OD600 nm, which were recorded to range from 0.06 to 0.23. The flasks were incubated further at 30° C. During the cultivation, a 1 mL sample was removed from each sample flasks at selected times, for analyzing the amount of itaconate and cis-aconitate accumulated in the medium. The results are shown in FIG. 6.

Figure 6:
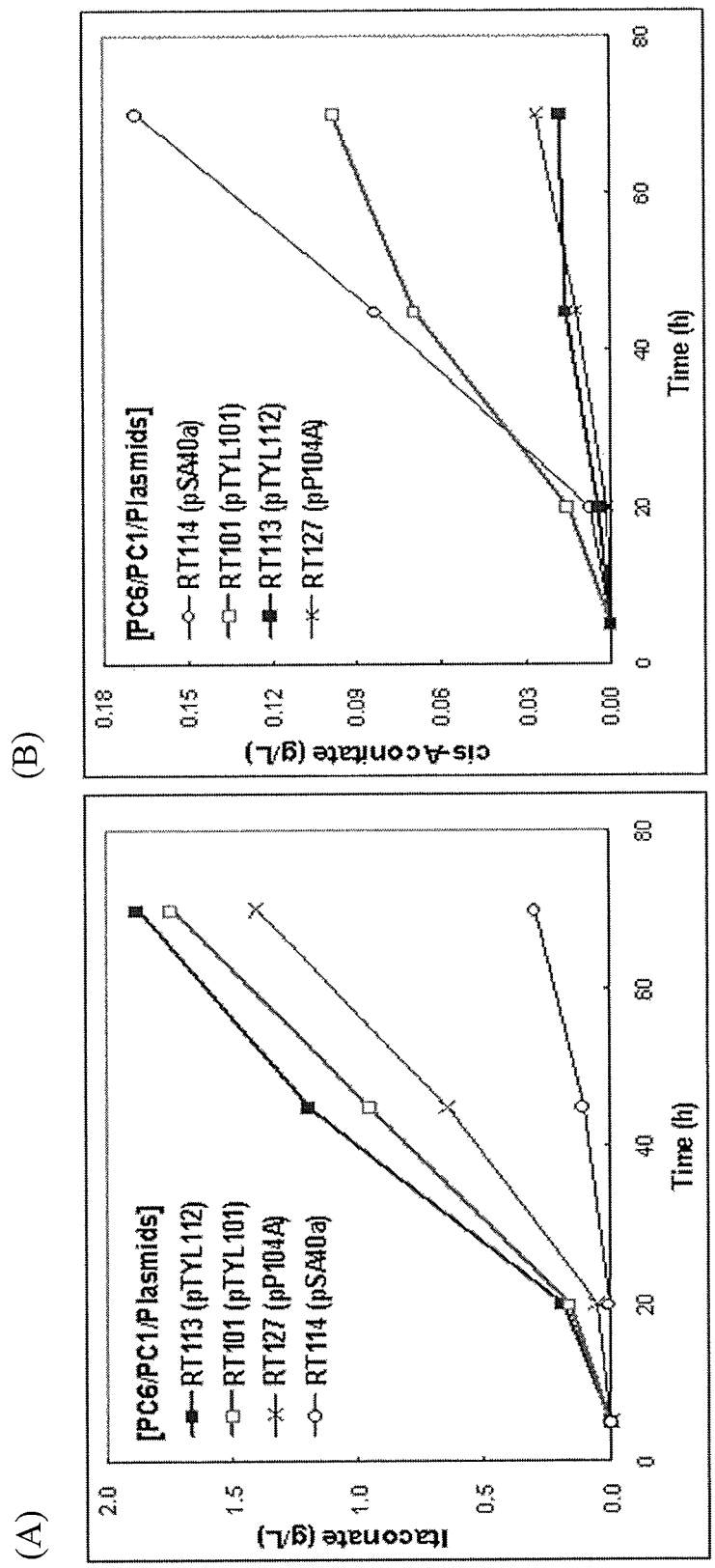
FIG. 6 is a set of graphs showing itaconate (A) and cis-aconitate (B) productions among different strains supplied with an excess of citrate and expressing individual CAD enzyme. These strains were based on the same host, *E. coli* PCI400\*, and each carried three plasmids, pPC1, pPC6 and the plasmid (listed in parenthesis) to test for function.

As shown in FIG. 6, relative yields of itaconate were higher in strains carrying cad-acnA fusion genes, RT113 and RT101, than in the controls, RT127 and RT114, carrying either transcriptionally fused cad and acnA genes or the blank vector. The higher yield of itaconate observed in RT113 as compared to RT101, was probably due to the increased expression of Pcp25::cad-acnA gene carried on pTYL112.

Comparing strains of RT101 and RT127, the translationally fused cad-acnA gene in RT101 and the transcriptionally fused cad::acnA genes in RT127 were regulated by the same IPTG-induced P$_L$lacO1 promoter. However, RT101 cells not only yielded more itaconate, but also released a higher amount of cis-aconitate into the medium. These results demonstrated that the bi-functional CAD-AcnA enzyme is more efficient for itaconate production than its individual counterparts.

The incorporation of pPC1 plasmid in these strains, though provided an extra cad gene, might have actually reduced the copy number of each of the three plasmids in the cells, as the same ColE1 origin was shared among them and the total plasmid number in each was controlled. In RT127 cells, this effect might have resulted in reduced-copy of pP104A and less expression from the P$_L$lacO1::cad::acnA gene on this plasmid, if compared with the same plasmid carried in RT017, in which only two plasmids, pPC6 and pP104A, existed. To replenish the reduced aconitase activity, plasmid pP154K, carrying transcriptionally fused P$_L$lacO1::cad:: acnB gene, was used to replace pPC1 in RT109. Itaconate production yields were then compared among RT109, RT101 and RT113.

Overnight cultures of the tested samples were prepared with 2-3 mL of LB medium (supplemented with antibiotics), from which 0.2-0.4 mL cell suspensions were seeded, respectively, into 30 mL of fermentation medium (0.4% yeast extract, 2% glycerol, 1×M9 salts, pH7.0) maintained in a 250 mL-flask. These culture flasks were, at first, incubated at either 30° C. or 37° C. with rotation (200×rpm), until cells OD600 nm reached to about 0.2-0.4. IPTG was then added to a concentration of 0.5 mM and the flasks were further incubated at 30° C. During the cultivation, a 1 mL sample was removed from each sample flasks at selected times for analyzing the amount of itaconate and cis-aconitate accumulated in the medium.

Figure 7:
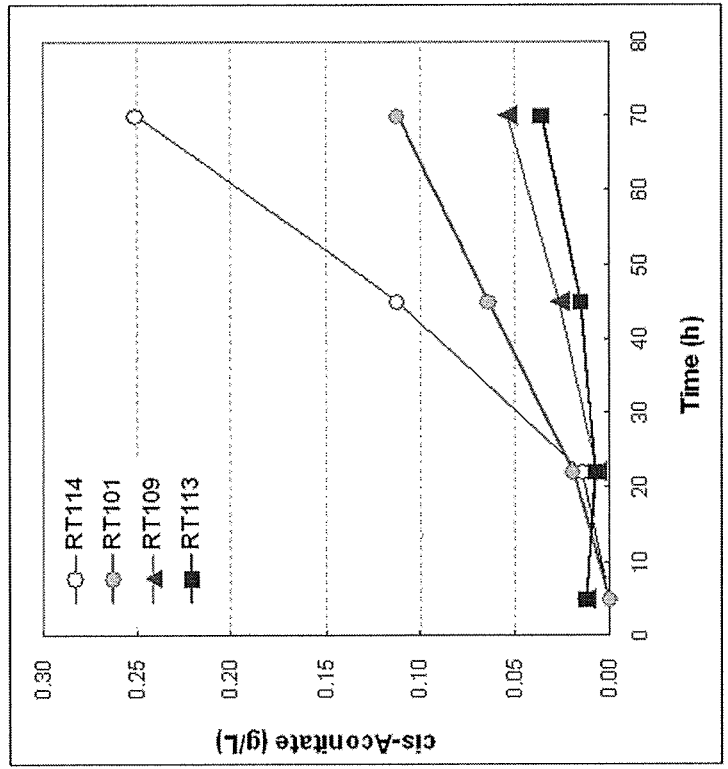
FIG. 7 is a set of graphs showing itaconate (A) and cis-aconitate (B) productions among different tested strains. These strains were based on the same host, *E. coli* PCI400\*.
Figure 7:
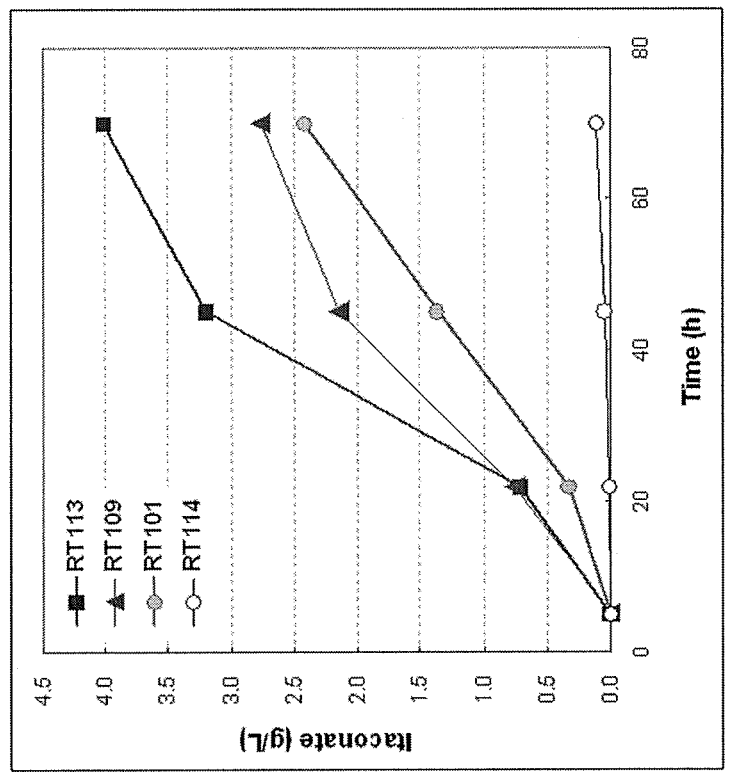

As shown in FIG. 7, itaconate production yield of RT109 was higher than that of RT101, unlike what was observed in RT127 mentioned above. These results indicated that, in RT109, the increased aconitase activity from P$_L$lacO1::cad:: acnB gene on pP154K plasmid did promote itaconate production. Under the shaking cultivation, itaconate yields of RT109 reached to about 2.1 g/L at 45 h and about 2.8 g/L at 70 h, without pH adjustment.

Notably, the highest yield of itaconate was observed in RT113, reaching to about 3.2 g/L at 45 h and about 4.0 g/L at 70 h without pH adjustment, and these yields were significantly higher than that observed in RT109. In RT113 cells, sufficient supply of citrate was provided by overexpression of ppc::gltA genes from pPC6 plasmid. High level aconitase and CAD activities were achieved by enhanced expression of Pcp25:: cad-acnA fusion gene on pTYL112 plasmid. Moreover, further increased CAD activity was supplied by individual cad gene carried on pPC1 plasmid.

Example 5

Construction of Bi-Functional CAD-Aco Fusion Enzyme Using Aconitase from *Y. lipolytica*

Aconitase is a key component of the tricarboxylic acid cycle found in cells of different organisms, and is highly conserved in structure and function. The success in building bi-functional CAD-Aco enzymes with *E. coli* aconitase, either the unique AcnB or the highly conserved AcnA, highlighted the possibility of functional fusion between CAD and Aco from eukaryotic sources.

As the above-described results demonstrated, cad-aco fusion genes can be applied to set up recombinant *E. coli* strains for itaconate production and with improved efficiency. Active CAD-Aco fusions based on eukaryotic aconitases have the potential to improve itaconate yield in eukaryotic hosts, such as native producers like *A. terreus*, or recombinant strains based on *A. niger* or *Y. lipolytica*.

For the construction of a CAD-Aco fusion based on an eukaryotic aconitase, we chose aco1 gene (YALI0D09361p; Yli_Aco1) from *Y. lipolytica* to fuse with the cad gene, using similar approaches described in Example 1 above. To test the functionality of the newly constructed CAD-Yaco1 fusion in a simple way that uses no eukaryotic host, the resulted fusion gene was designed to be expressed in *E. coli* SY403K, in which the chromosome-encoded acnA and acnB have been deleted. Thus, plasmid-encoded aconitase and cad activities can be easily detected from the presence of itaconate and/or cis-aconitate produced, by expressing the fusion gene in SY403K host.

DNA sequences of Yli_Aco1 were retrieved from Genbank maintained by the NCBI. Amino acid sequences of this gene are highly similar to sequences of aconitase from *A. terreus*, AcnA (accession number: AAC61778), with 81.4% similarity and 70.7% identity. There are two exons found in Yli_Aco1, of which exon1 is short and includes only 30 nt (encoding the first 10 amino acids).

PCR primers were used to: 1) amplify exon 2 of Yli_Aco1 gene from chromosome of *Y. lipolytica*; 2) regenerate exon 1 coding region; 3) regenerate linker region; and 4) create a DNA fragment containing linker-Yaco1 fusion with XbaI and HindIII at the ends. The primers used are listed in Table 6 below.

TABLE 6

Primers used for cloning of Yli_Aco1 and construction of P_LlacO1::cad-Yaco1 fusion gene

| Names | Use/locations | | Sequences |
|---|---|---|---|
| C13-0717-03 | amplification of exon 2 | F | GGTCCCAAAATTACCTCGACCAAC CACA (SEQ ID NO: 38) |
| C13-0717-04 | amplification of exon 2 | R | GTAAACATGACAAAACTGTCGATC ACAATCAA (SEQ ID NO: 39) |
| C13-0418-01 | cad (V490GI)-Linker | F | TGTCCGGTTAAATCCCCACTGGGT ATTGAATTTG (SEQ ID NO: 23) |
| C13-0410-01 | cad (V490GI)-Linker | F | TGTCCGGTTAAATCCCCACTGGGT ATTGAATTTGGTCCGGGTC (SEQ ID NO: 24) |
| C13-0410-02 | Linker | R | AGAGGGCCAGGACCAGGACCTGG ACCCGGACCAAATTCAATA (SEQ ID NO: 25) |
| C13-0410-03 | Linker (XbaI site) | F | CCTGGTCCTGGCCCTCTAGAAGTG TTGTTCCAAGGTCC (SEQ ID NO: 26) |
| C13-0412-01 | Linker-ATG (initiation) | R | CATGAGTTTCGCACGACCAGGACC TTGGAACAACACTT (SEQ ID NO: 31) |
| C13-0717-05 | Linker-Yli-Aco1 (1st-10th codons) | F | GGTCGTGCGAAACTCATGCTGGCT AGTCGTGTTTCAATCAAAG (SEQ ID NO: 40) |
| C13-0717-06 | Yli-Aco1 (4th - 17th codons) | R | AGGCTACGTGCAAGGCGTGGAGCT TTGATTGAAACACGACTA (SEQ ID NO: 41) |
| C13-0717-07 | Yli-Aco1 (11th-25th codons) | F | ACGCCTTGCACGTAGCCTTGCGAC TACCACTAATGCC TCCCTC (SEQ ID NO: 42) |
| C13-0717-08 | Yli-Aco1 (C-terminus)-HindIII | R | TGGGCGAAGCTTATACACAAAACA CTTATTTCTTGGAGGCAG (SEQ ID NO: 43) |

To construct pTYL107, the expression plasmid carrying P_LlacO1::cad-Yaco1 fusion gene, the PCR-amplified linker-Yaco1 fusion was restricted with XbaI and HindIII enzymes, and then used to replace the acnA coding region on pTYL101 plasmid, in between of the unique XbaI and HindIII sites.

To test the functional expression of pTYL107 in *E. coli* SY403K, fermentation yields of itaconate in RT024 were compared with strains carrying functional cad-aco genes, including RT021, RT022, and RT023. For the controls, strain RT027, which carried pP190A encoding acnA gene from *A. terreus*, and strain RT030, which carried the blank vector pSA40a, were used.

Figure 8:
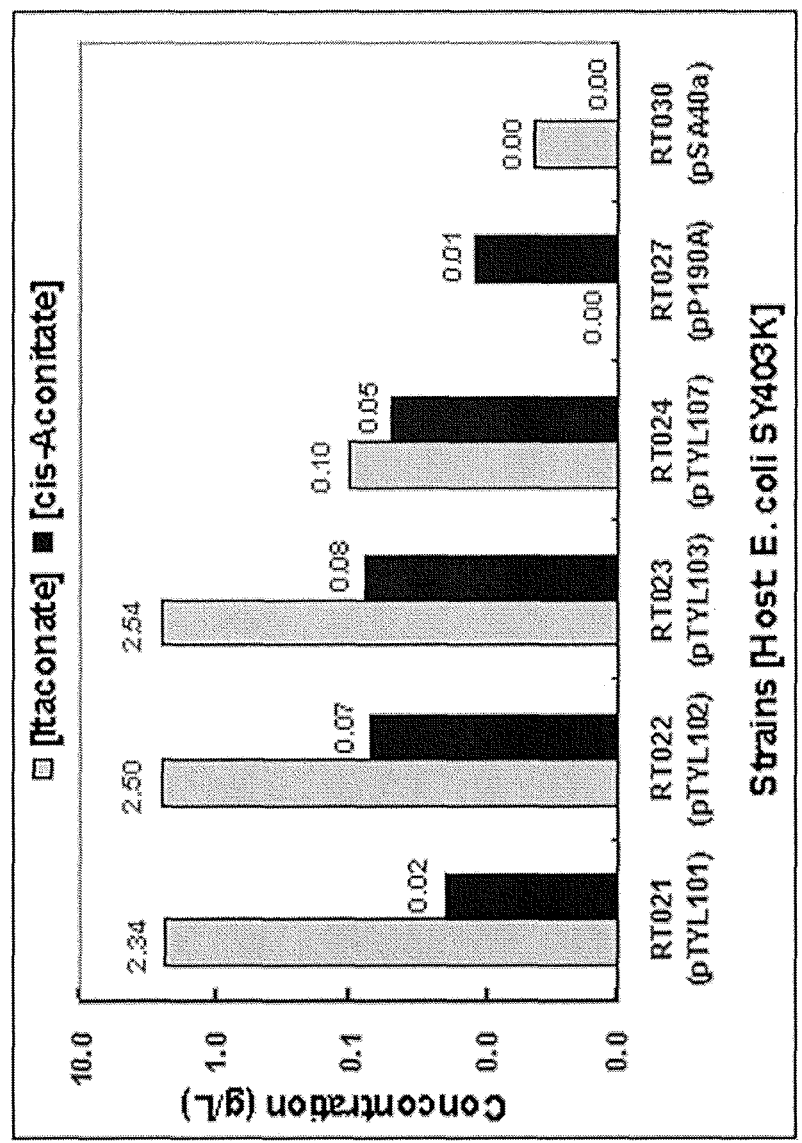
FIG. 8 is a graph showing a comparison of itaconate and cis-aconitate productions among different strains supplied with an excess of citrate. These strains were based on the same host, *E. coli* SY403K, and each carried two plasmids, pPC6 and the plasmid (listed in parenthesis) to test for function.

Overnight cultures of the tested samples were prepared with 2-3 mL of LB medium (supplemented with antibiotics), from which 0.2-0.4 mL cell suspensions were seeded, respectively, into 30 mL of fermentation medium (0.4% yeast extract, 2% glycerol, 1×M9 salts, pH7.0) maintained in a 250 mL-flask. These culture flasks were, at first, incubated at either 30° C. or 37° C. with rotation (200×rpm), until cells OD600 nm reached to about 0.2-0.4. IPTG was then added to a concentration of 0.5 mM and the flasks were further incubated at 30° C. During cultivation, 1 mL samples were removed from each sample flasks at selected times, for analyzing the amount of itaconate and cis-aconitate accumulated in the medium. Results are shown as in FIG. 8.

In the culture medium of RT024, significant amounts of itaconate and cis-aconitate were detected, similar to the positive controls (RT021, RT022 and RT023), though the yield of itaconate was less. See FIG. 8. These results strongly suggest that the CAD-Yaco1 expressed in RT024 were bi-functional, able to convert cellular citrate to cis-aconitate, and able to convert cis-aconitate to itaconate. The relatively low yield of itaconate found in RT024 was probably due to a low aconitase activity of Yli_Aco1 in the heterogeneous *E. coli* host. This view was supported by the low yield of cis-aconitate observed in strain RT027, which independently expressed an AcnA from heterogeneous *A. terreus*.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims. It will be apparent to those skilled in the art that various modifications and variations can be made to the disclosed embodiments. It is intended that the specification and examples be considered as exemplary only, with a true scope of the disclosure being indicated by the following claims and their equivalents.

The invention claimed is:

1. A fusion polypeptide, comprising an aconitase (Aco) and a cis-aconitate decarboxylase (CAD), wherein the polypeptide exhibits an Aco activity and a CAD activity.

2. The fusion polypeptide of claim 1, wherein the CAD is in the N-terminal portion of the polypeptide.

3. The fusion polypeptide of claim 2, further comprising a linker between the Aco and the CAD.

4. The fusion polypeptide of claim 3, wherein the Aco is an *E. coli* AcnA or *E. coli* AcnB.

5. The fusion polypeptide of claim 1, wherein the Aco is a eukaryotic Aco.

6. The fusion polypeptide of claim 4, wherein the AcnB is the AcnB E424Q mutant.

7. The fusion polypeptide of claim 1, wherein the CAD is the CAD V49001 mutant.

8. The fusion polypeptide of claim 1, wherein the fusion polypeptide has the amino acid sequence of SEQ ID NO: 9, 11, 13, or 15.

* * * * *